US 8,079,706 B2

(12) United States Patent
Silvestrini et al.

(10) Patent No.: US 8,079,706 B2
(45) Date of Patent: Dec. 20, 2011

(54) METHOD AND APPARATUS FOR ALIGNING A MASK WITH THE VISUAL AXIS OF AN EYE

(75) Inventors: Thomas A. Silvestrini, Alamo, CA (US); Bruce A. Christie, Upland, CA (US); Kevin F. Hahnen, Center Ossipee, NH (US); Carl F. Knopp, Livermore, CA (US)

(73) Assignee: AcuFocus, Inc., Irvine, CA (US)

( * ) Notice: Subject to any disclaimer, the term of this patent is extended or adjusted under 35 U.S.C. 154(b) by 1224 days.

(21) Appl. No.: 11/418,390

(22) Filed: May 3, 2006

(65) Prior Publication Data
US 2007/0225691 A1     Sep. 27, 2007

Related U.S. Application Data

(63) Continuation of application No. 10/854,032, filed on May 26, 2004, now abandoned.

(60) Provisional application No. 60/479,129, filed on Jun. 17, 2003.

(51) Int. Cl.
*A61B 3/00*     (2006.01)
*A61F 2/14*     (2006.01)

(52) U.S. Cl. ...... 351/200; 351/247; 623/5.11; 623/5.13; 623/5.16

(58) Field of Classification Search .................. 351/205, 351/208, 200; 623/4.1, 5.11–5.13, 5.16
See application file for complete search history.

(56) References Cited

U.S. PATENT DOCUMENTS

| 564,518 A | 7/1896 | Heilborn |
| 1,206,132 A | 11/1916 | Otte |
| 1,959,915 A | 5/1934 | Guthrie |
| 2,129,305 A | 9/1938 | Feinbloom |
| 2,714,721 A | 8/1955 | Stone, Jr. |
| 3,034,403 A | 5/1962 | Neefe |
| 3,270,099 A | 8/1966 | Camp |
| 3,339,997 A | 9/1967 | Wesley |
| 3,458,870 A | 8/1969 | Stone, Jr. |

(Continued)

FOREIGN PATENT DOCUMENTS

EP     0 457 553 A2     11/1991
(Continued)

OTHER PUBLICATIONS

Accommodation Responses and Ageing. Heron et al. IOVS, Nov. 1999, vol. 40, No. 12, pp. 2872-2883.

(Continued)

*Primary Examiner* — Darryl J Collins
*Assistant Examiner* — Zachary Wilkes
(74) *Attorney, Agent, or Firm* — Knobbe, Martens, Olson & Bear, LLP

(57) ABSTRACT

An apparatus is provided for aligning an implant with a visual axis of an eye of a patient. The apparatus has an instrument with an instrument axis and an aperture through which the patient may look along the instrument axis. The implant includes an aperture having an implant axis that can be positioned substantially collinear with the instrument axis. The implant further includes a substantially opaque annulus extending between the aperture and an outer periphery of the implant. The annulus has a nutrient transport structure for conveying nutrients between anterior and posterior surfaces of the implant.

18 Claims, 31 Drawing Sheets

U.S. PATENT DOCUMENTS

| | | |
|---|---|---|
| 3,507,566 A | 4/1970 | Knapp |
| 3,578,850 A | 5/1971 | Grant |
| 3,600,098 A | 8/1971 | Mohrman |
| 3,726,587 A | 4/1973 | Kendall |
| 3,794,414 A | 2/1974 | Wesley |
| 3,852,032 A | 12/1974 | Urbach |
| 3,982,541 A | 9/1976 | L'Esperance, Jr. |
| 4,010,496 A | 3/1977 | Neefe |
| 4,073,015 A | 2/1978 | Peyman |
| 4,099,529 A | 7/1978 | Peyman |
| 4,138,191 A | 2/1979 | Peyman |
| 4,191,195 A | 3/1980 | Miller |
| 4,272,191 A | 6/1981 | Bergkvist |
| 4,298,004 A | 11/1981 | Schachar et al. |
| 4,312,575 A | 1/1982 | Peyman et al. |
| 4,367,949 A | 1/1983 | Lavering |
| 4,402,681 A | 9/1983 | Haas et al. |
| 4,450,593 A | 5/1984 | Poler |
| 4,452,235 A | 6/1984 | Reynolds |
| 4,485,499 A | 12/1984 | Castleman |
| 4,528,311 A | 7/1985 | Beard et al. |
| 4,536,240 A | 8/1985 | Winn |
| 4,547,914 A | 10/1985 | Castleman |
| 4,547,915 A | 10/1985 | Castleman |
| 4,575,915 A | 3/1986 | Clark et al. |
| 4,576,453 A | 3/1986 | Borowsky |
| 4,607,617 A | 8/1986 | Choyce |
| 4,612,012 A | 9/1986 | White |
| 4,615,702 A | 10/1986 | Koziol et al. |
| 4,617,023 A | 10/1986 | Peyman |
| 4,624,669 A | 11/1986 | Grendahl |
| 4,633,866 A | 1/1987 | Peyman et al. |
| 4,636,049 A | 1/1987 | Blaker |
| 4,636,211 A | 1/1987 | Nielsen et al. |
| 4,636,212 A | 1/1987 | Posin et al. |
| 4,637,697 A | 1/1987 | Freeman |
| 4,639,105 A | 1/1987 | Neefe |
| 4,641,934 A | 2/1987 | Freeman |
| 4,642,112 A | 2/1987 | Freeman |
| 4,646,720 A | 3/1987 | Peyman et al. |
| 4,655,774 A | 4/1987 | Choyce |
| 4,662,370 A | 5/1987 | Hoffmann et al. |
| 4,665,913 A | 5/1987 | L'Esperance, Jr. |
| 4,666,446 A | 5/1987 | Koziol et al. |
| 4,669,466 A | 6/1987 | L'Esperance, Jr. |
| 4,674,503 A | 6/1987 | Peyman et al. |
| 4,676,790 A | 6/1987 | Kern |
| 4,676,791 A | 6/1987 | Le Master et al. |
| 4,685,922 A | 8/1987 | Peyman |
| 4,701,038 A | 10/1987 | Neefe |
| 4,702,865 A | 10/1987 | Koziol et al. |
| 4,704,016 A | 11/1987 | de Carle |
| 4,710,003 A | 12/1987 | Masuda et al. |
| 4,713,446 A | 12/1987 | DeVore et al. |
| 4,715,858 A | 12/1987 | Lindstrom |
| 4,718,418 A | 1/1988 | L'Esperance |
| 4,729,372 A | 3/1988 | L'Esperance, Jr. |
| 4,729,373 A | 3/1988 | Peyman |
| 4,744,360 A | 5/1988 | Bath |
| 4,753,654 A | 6/1988 | Posin et al. |
| 4,779,973 A | 10/1988 | Miller et al. |
| 4,785,796 A | 11/1988 | Mattson |
| 4,799,784 A | 1/1989 | Safir |
| 4,799,931 A | 1/1989 | Lindstrom |
| 4,807,623 A | 2/1989 | Lieberman |
| 4,808,181 A | 2/1989 | Kelman |
| 4,813,955 A | 3/1989 | Achatz et al. |
| 4,814,050 A | 3/1989 | McGraw et al. |
| 4,838,266 A | 6/1989 | Koziol et al. |
| 4,840,175 A | 6/1989 | Peyman |
| 4,842,599 A | 6/1989 | Bronstein |
| 4,865,601 A | 9/1989 | Caldwell et al. |
| 4,869,587 A | 9/1989 | Breger |
| 4,878,910 A | 11/1989 | Koziol et al. |
| 4,881,954 A | 11/1989 | Bikson et al. |
| 4,890,913 A | 1/1990 | De Carle |
| 4,891,043 A | 1/1990 | Zeimer et al. |
| 4,898,461 A | 2/1990 | Portney |
| 4,903,695 A | 2/1990 | Warner et al. |
| 4,923,297 A | 5/1990 | Arndt |
| 4,932,970 A | 6/1990 | Portney |
| 4,955,904 A | 9/1990 | Atebara et al. |
| 4,958,922 A | 9/1990 | Binh et al. |
| 4,961,744 A | 10/1990 | Kilmer et al. |
| 4,965,545 A | 10/1990 | Johnson |
| 4,971,432 A | 11/1990 | Koeniger |
| 4,976,732 A | 12/1990 | Vorosmarthy |
| 4,983,181 A | 1/1991 | Civerchia |
| 4,985,559 A | 1/1991 | Goldberg et al. |
| 4,990,165 A | 2/1991 | Bikson et al. |
| 4,994,058 A | 2/1991 | Raven et al. |
| 4,994,080 A | 2/1991 | Shepard |
| 4,997,268 A | 3/1991 | Dauvergne |
| 5,002,571 A | 3/1991 | O'Donnell, Jr. |
| 5,013,319 A | 5/1991 | Davis |
| 5,019,097 A | 5/1991 | Knight et al. |
| 5,026,393 A | 6/1991 | Mackool |
| 5,030,230 A | 7/1991 | White |
| 5,041,133 A | 8/1991 | Sayano et al. |
| 5,061,914 A | 10/1991 | Busch et al. |
| 5,063,942 A | 11/1991 | Kilmer et al. |
| 5,067,961 A | 11/1991 | Kelman et al. |
| 5,076,684 A | 12/1991 | Simpson et al. |
| 5,089,022 A | 2/1992 | Koester et al. |
| 5,089,024 A | 2/1992 | Christie et al. |
| 5,094,521 A * | 3/1992 | Jolson et al. ............... 351/210 |
| 5,098,443 A | 3/1992 | Parel et al. |
| 5,098,444 A | 3/1992 | Feaster |
| 5,104,957 A | 4/1992 | Kelman et al. |
| 5,108,169 A | 4/1992 | Mandell |
| 5,108,428 A | 4/1992 | Capecchi et al. |
| 5,112,350 A | 5/1992 | Civerchia et al. |
| 5,116,111 A | 5/1992 | Simpson et al. |
| 5,119,555 A | 6/1992 | Johnson |
| 5,123,921 A | 6/1992 | Werblin et al. |
| 5,133,745 A | 7/1992 | Falcetta et al. |
| 5,149,331 A | 9/1992 | Ferdman et al. |
| 5,152,789 A | 10/1992 | Willis |
| 5,160,463 A | 11/1992 | Evans et al. |
| 5,165,897 A | 11/1992 | Johnson |
| 5,166,712 A | 11/1992 | Portney |
| 5,171,318 A | 12/1992 | Gibson et al. |
| 5,185,152 A | 2/1993 | Peyman |
| 5,192,316 A | 3/1993 | Ting |
| 5,192,318 A | 3/1993 | Schneider et al. |
| 5,196,026 A | 3/1993 | Barrett et al. |
| 5,215,104 A | 6/1993 | Steinert |
| 5,219,844 A | 6/1993 | Peyman et al. |
| 5,225,858 A | 7/1993 | Portney |
| 5,239,066 A | 8/1993 | Falkow et al. |
| 5,245,367 A | 9/1993 | Miller et al. |
| 5,245,738 A | 9/1993 | Johnson |
| 5,258,412 A | 11/1993 | Peyman et al. |
| 5,260,727 A | 11/1993 | Oksman et al. |
| 5,261,997 A | 11/1993 | Inselmann |
| 5,269,812 A | 12/1993 | White |
| 5,270,744 A | 12/1993 | Portney |
| 5,274,404 A | 12/1993 | Michael |
| 5,292,514 A | 3/1994 | Capecchi et al. |
| 5,296,881 A | 3/1994 | Freeman |
| 5,300,116 A | 4/1994 | Chirila et al. |
| 5,300,118 A | 4/1994 | Silvestrini et al. |
| 5,302,978 A | 4/1994 | Evans et al. |
| 5,310,654 A | 5/1994 | Isberg et al. |
| 5,312,393 A | 5/1994 | Mastel |
| 5,314,439 A | 5/1994 | Sugita |
| 5,314,961 A | 5/1994 | Anton et al. |
| 5,315,344 A | 5/1994 | Clark et al. |
| 5,318,044 A | 6/1994 | Kilmer et al. |
| 5,318,047 A | 6/1994 | Davenport et al. |
| 5,323,788 A | 6/1994 | Silvestrini et al. |
| 5,325,880 A | 7/1994 | Johnson et al. |
| 5,336,261 A | 8/1994 | Barrett et al. |
| 5,346,689 A | 9/1994 | Peyman et al. |
| 5,354,331 A | 10/1994 | Schachar |
| 5,366,499 A | 11/1994 | Py |
| 5,368,604 A | 11/1994 | Kilmer et al. |

| | | | | | |
|---|---|---|---|---|---|
| 5,374,272 A | 12/1994 | Arpa et al. | 5,960,812 A | 10/1999 | Johnson |
| D354,566 S | 1/1995 | Donahoo | 5,964,748 A | 10/1999 | Peyman |
| 5,391,201 A | 2/1995 | Barrett et al. | 5,964,776 A | 10/1999 | Peyman |
| 5,401,508 A | 3/1995 | Manesis | 5,965,330 A | 10/1999 | Evans et al. |
| 5,403,335 A | 4/1995 | Loomas et al. | 5,980,040 A | 11/1999 | Xu et al. |
| 5,405,384 A | 4/1995 | Silvestrini | 5,997,559 A | 12/1999 | Ziemer |
| 5,422,424 A | 6/1995 | Selsted et al. | 6,010,901 A | 1/2000 | Miller, III et al. |
| 5,433,745 A | 7/1995 | Graham et al. | 6,024,447 A | 2/2000 | Portney |
| 5,434,630 A | 7/1995 | Bransome | 6,036,957 A | 3/2000 | Weiner et al. |
| 5,437,274 A | 8/1995 | Khoobehi et al. | 6,063,073 A | 5/2000 | Peyman |
| 5,458,819 A | 10/1995 | Chirila et al. | 6,083,236 A | 7/2000 | Feingold |
| 5,474,548 A | 12/1995 | Knopp et al. | 6,086,204 A | 7/2000 | Magnante |
| 5,476,515 A | 12/1995 | Kelman et al. | 6,090,141 A | 7/2000 | Lindstrom |
| 5,480,427 A | 1/1996 | Kelman et al. | 6,096,077 A | 8/2000 | Callahan et al. |
| 5,489,300 A | 2/1996 | Capecchi et al. | 6,102,946 A | 8/2000 | Nigam |
| 5,496,339 A | 3/1996 | Koepnick | 6,106,552 A | 8/2000 | Lacombe et al. |
| 5,505,723 A | 4/1996 | Muller | 6,126,286 A | 10/2000 | Portney |
| 5,507,740 A | 4/1996 | O'Donnell, Jr. | 6,161,544 A | 12/2000 | DeVore et al. |
| 5,516,522 A | 5/1996 | Peyman et al. | 6,164,282 A | 12/2000 | Gwon et al. |
| 5,522,888 A | 6/1996 | Civerchia | 6,165,189 A | 12/2000 | Ziemer |
| 5,526,178 A | 6/1996 | Goldstein et al. | 6,171,336 B1 | 1/2001 | Sawusch |
| 5,527,356 A | 6/1996 | Peyman et al. | 6,176,878 B1 | 1/2001 | Gwon et al. |
| 5,547,473 A | 8/1996 | Peyman | 6,183,498 B1 | 2/2001 | DeVore et al. |
| 5,567,365 A | 10/1996 | Weinschenk, III et al. | 6,197,019 B1 | 3/2001 | Peyman |
| 5,571,177 A | 11/1996 | Deacon et al. | 6,197,057 B1 | 3/2001 | Peyman et al. |
| 5,579,063 A | 11/1996 | Magnante et al. | 6,197,934 B1 | 3/2001 | DeVore et al. |
| RE35,421 E | 1/1997 | Ruiz et al. | 6,203,538 B1 | 3/2001 | Peyman |
| 5,599,537 A | 2/1997 | Miller, III et al. | 6,204,365 B1 | 3/2001 | DeVore et al. |
| 5,605,938 A | 2/1997 | Roufa et al. | 6,210,005 B1 | 4/2001 | Portney |
| 5,608,471 A | 3/1997 | Miller | 6,217,571 B1 | 4/2001 | Peyman |
| 5,610,719 A | 3/1997 | Allen et al. | 6,217,596 B1 | 4/2001 | Farah |
| 5,627,613 A * | 5/1997 | Kaneko .................. 351/221 | 6,221,067 B1 | 4/2001 | Peyman |
| 5,628,794 A | 5/1997 | Lindstrom | 6,221,105 B1 | 4/2001 | Portney |
| 5,628,795 A | 5/1997 | Langerman | 6,228,114 B1 | 5/2001 | Lee |
| 5,628,798 A | 5/1997 | Eggleston et al. | 6,251,118 B1 | 6/2001 | Proudfoot et al. |
| 5,631,243 A | 5/1997 | Kelman et al. | 6,277,146 B1 | 8/2001 | Peyman et al. |
| 5,632,773 A | 5/1997 | Graham et al. | 6,280,470 B1 | 8/2001 | Peyman |
| 5,662,706 A | 9/1997 | Legerton et al. | 6,280,471 B1 | 8/2001 | Peyman |
| 5,662,908 A | 9/1997 | Falkow et al. | 6,283,595 B1 | 9/2001 | Breger |
| 5,672,885 A | 9/1997 | Allen et al. | 6,335,006 B1 | 1/2002 | Miller |
| 5,674,724 A | 10/1997 | Miller, III et al. | 6,357,875 B1 | 3/2002 | Herrick |
| 5,674,736 A | 10/1997 | Miller, III et al. | 6,358,280 B1 | 3/2002 | Herrick |
| 5,693,092 A | 12/1997 | Silvestrini et al. | 6,361,560 B1 | 3/2002 | Nigam |
| 5,695,983 A | 12/1997 | Miller et al. | 6,387,379 B1 | 5/2002 | Goldberg et al. |
| 5,697,923 A | 12/1997 | Poler | 6,391,055 B1 | 5/2002 | Ikada et al. |
| 5,697,973 A | 12/1997 | Peyman et al. | 6,403,947 B1 | 6/2002 | Hoyt et al. |
| 5,702,440 A | 12/1997 | Portney | 6,406,494 B1 | 6/2002 | Laguette et al. |
| 5,713,844 A | 2/1998 | Peyman | 6,416,179 B1 | 7/2002 | Lieberman et al. |
| 5,713,957 A | 2/1998 | Steele et al. | 6,423,093 B1 | 7/2002 | Hicks et al. |
| 5,719,656 A | 2/1998 | Bowling | 6,436,092 B1 | 8/2002 | Peyman |
| 5,720,894 A | 2/1998 | Neev et al. | 6,457,826 B1 | 10/2002 | Lett |
| 5,722,971 A | 3/1998 | Peyman | 6,458,141 B1 | 10/2002 | Peyman |
| 5,731,196 A | 3/1998 | Miller, III et al. | 6,470,108 B1 | 10/2002 | Johnson |
| 5,731,862 A | 3/1998 | Winkler | 6,488,707 B1 | 12/2002 | Callahan et al. |
| 5,733,760 A | 3/1998 | Lu et al. | 6,494,910 B1 | 12/2002 | Ganem et al. |
| 5,752,967 A | 5/1998 | Kritzinger et al. | 6,497,700 B1 | 12/2002 | LaHaye |
| 5,757,458 A | 5/1998 | Miller et al. | 6,503,276 B2 | 1/2003 | Lang et al. |
| 5,771,088 A | 6/1998 | Perrott | 6,527,389 B2 | 3/2003 | Portney |
| 5,771,742 A | 6/1998 | Bokaie et al. | 6,533,905 B2 | 3/2003 | Johnson et al. |
| 5,774,202 A | 6/1998 | Abraham et al. | 6,536,899 B1 | 3/2003 | Fiala |
| 5,782,911 A | 7/1998 | Herrick | 6,551,307 B2 | 4/2003 | Peyman |
| 5,786,883 A | 7/1998 | Miller et al. | 6,554,424 B1 | 4/2003 | Miller et al. |
| 5,800,533 A | 9/1998 | Eggleston et al. | 6,555,103 B2 | 4/2003 | Leukel et al. |
| 5,806,530 A | 9/1998 | Herrick | 6,569,199 B1 | 5/2003 | Dotan et al. |
| 5,814,680 A | 9/1998 | Imafuku et al. | 6,581,993 B2 | 6/2003 | Nigam |
| 5,836,313 A | 11/1998 | Perez et al. | RE38,193 E | 7/2003 | Bowling |
| 5,840,848 A | 11/1998 | Sturrock et al. | 6,588,022 B1 | 7/2003 | Anders et al. |
| 5,855,605 A | 1/1999 | Herrick | 6,588,902 B2 | 7/2003 | Isogai |
| 5,858,980 A | 1/1999 | Weiner et al. | 6,589,280 B1 | 7/2003 | Koziol |
| 5,861,486 A | 1/1999 | DeVore et al. | 6,592,621 B1 | 7/2003 | Domino |
| 5,863,537 A | 1/1999 | Dalie et al. | 6,599,305 B1 | 7/2003 | Feingold |
| 5,864,128 A | 1/1999 | Plesko | 6,607,527 B1 | 8/2003 | Ruiz et al. |
| 5,864,378 A | 1/1999 | Portney | 6,607,556 B1 | 8/2003 | Nigam |
| 5,870,167 A * | 2/1999 | Knopp et al. ............ 351/212 | 6,613,088 B1 | 9/2003 | Babizhayev |
| 5,874,537 A | 2/1999 | Kelman et al. | 6,614,570 B2 | 9/2003 | Johnson et al. |
| 5,903,099 A | 5/1999 | Johnson et al. | 6,620,634 B2 | 9/2003 | Johnson et al. |
| 5,905,561 A | 5/1999 | Lee et al. | 6,623,497 B1 | 9/2003 | Feingold |
| 5,919,185 A | 7/1999 | Peyman | 6,623,522 B2 | 9/2003 | Nigam |
| 5,929,968 A | 7/1999 | Cotie et al. | 6,624,730 B2 | 9/2003 | Johnson et al. |

| | | |
|---|---|---|
| 6,626,941 B2 | 9/2003 | Nigam |
| 6,632,244 B1 | 10/2003 | Nigam |
| 6,663,668 B1 | 12/2003 | Chaouk et al. |
| 6,669,795 B2 | 12/2003 | Johnson et al. |
| 6,673,112 B2 | 1/2004 | Nigam |
| 6,729,599 B2 | 5/2004 | Johnson |
| 6,740,116 B2 | 5/2004 | Morcher |
| 6,742,761 B2 | 6/2004 | Johnson et al. |
| 6,746,890 B2 | 6/2004 | Gupta et al. |
| 6,755,858 B1 | 6/2004 | White |
| 6,786,926 B2 | 9/2004 | Peyman |
| 6,790,298 B2 | 9/2004 | Johnson et al. |
| 6,811,256 B1 | 11/2004 | Becherer et al. |
| 6,849,090 B2 | 2/2005 | Nigam |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,976,997 B2 | 12/2005 | Noolandi et al. |
| 7,207,998 B2 | 4/2007 | Feingold |
| 7,364,674 B1 | 4/2008 | Hoover |
| 7,404,637 B2 | 7/2008 | Miller et al. |
| 7,404,638 B2 | 7/2008 | Miller et al. |
| 7,491,350 B2 | 2/2009 | Silvestrini |
| 7,628,810 B2 | 12/2009 | Christie et al. |
| 7,645,291 B2 | 1/2010 | Ross et al. |
| 7,828,844 B2 | 11/2010 | Marmo et al. |
| 2001/0004702 A1 | 6/2001 | Peyman |
| 2001/0027314 A1 | 10/2001 | Peyman |
| 2001/0034516 A1 | 10/2001 | Peyman |
| 2001/0047203 A1 | 11/2001 | Dalton et al. |
| 2001/0050750 A1 | 12/2001 | Breger |
| 2002/0010510 A1 | 1/2002 | Silvestrini |
| 2002/0028330 A1 | 3/2002 | Patel et al. |
| 2002/0055753 A1 | 5/2002 | Silvestrini |
| 2002/0057148 A1 | 5/2002 | Johnson et al. |
| 2002/0075447 A1 | 6/2002 | Andino et al. |
| 2002/0107337 A1 | 8/2002 | Rosenzweig et al. |
| 2002/0107566 A1 | 8/2002 | Nigam |
| 2002/0111677 A1 | 8/2002 | Nigam |
| 2002/0128710 A1 | 9/2002 | Eggleston |
| 2002/0169491 A1 | 11/2002 | Foster et al. |
| 2002/0188351 A1 | 12/2002 | Laguette |
| 2002/0196409 A1 | 12/2002 | Jani |
| 2003/0002994 A1 | 1/2003 | Johnson et al. |
| 2003/0007122 A1 | 1/2003 | Streibig |
| 2003/0014042 A1 | 1/2003 | Juhasz et al. |
| 2003/0014107 A1 | 1/2003 | Reynard |
| 2003/0033013 A1 | 2/2003 | Callahan et al. |
| 2003/0045930 A1 | 3/2003 | Nguyen |
| 2003/0055497 A1 | 3/2003 | Hicks et al. |
| 2003/0071893 A1 | 4/2003 | Miller et al. |
| 2003/0078655 A1 | 4/2003 | Callahan et al. |
| 2003/0088313 A1 | 5/2003 | Nigam |
| 2003/0127318 A1 | 7/2003 | Johnson et al. |
| 2003/0216763 A1 | 11/2003 | Patel |
| 2003/0220653 A1 | 11/2003 | Perez |
| 2004/0014253 A1 | 1/2004 | Gupta et al. |
| 2004/0019379 A1 | 1/2004 | Glick et al. |
| 2004/0047014 A1 | 3/2004 | Parker et al. |
| 2004/0068317 A1 | 4/2004 | Knight |
| 2004/0078075 A1 | 4/2004 | Koziol |
| 2004/0080239 A1 | 4/2004 | Gupta et al. |
| 2004/0106929 A1 | 6/2004 | Masket |
| 2005/0031697 A1 | 2/2005 | Vehige et al. |
| 2005/0046794 A1 | 3/2005 | Silvestrini et al. |
| 2005/0049621 A1 | 3/2005 | Feingold et al. |
| 2005/0080485 A1 | 4/2005 | Nigam |
| 2005/0119738 A1 | 6/2005 | Nigam |
| 2005/0124983 A1 | 6/2005 | Fret et al. |
| 2005/0182488 A1 | 8/2005 | Peyman |
| 2006/0079959 A1 | 4/2006 | Christie et al. |
| 2006/0079960 A1 | 4/2006 | Christie et al. |
| 2006/0113054 A1 | 6/2006 | Silvestrini |
| 2006/0184243 A1 | 8/2006 | Yilmaz |
| 2006/0235514 A1 | 10/2006 | Silvestrini |
| 2006/0241751 A1 | 10/2006 | Marmo et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271027 A1 | 11/2006 | Silvestrini et al. |
| 2006/0271176 A1 | 11/2006 | Christie et al. |
| 2006/0271177 A1 | 11/2006 | Christie et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0016234 A1 | 1/2007 | Daxer |
| 2007/0219542 A1 | 9/2007 | Yahagi |
| 2008/0033546 A1 | 2/2008 | Liang |
| 2009/0012505 A1 | 1/2009 | Chernyak |
| 2009/0021692 A1 | 1/2009 | Miller et al. |
| 2009/0059168 A1 | 3/2009 | Miller et al. |
| 2009/0069817 A1 | 3/2009 | Peyman |
| 2009/0222086 A1 | 9/2009 | Lui et al. |

FOREIGN PATENT DOCUMENTS

| | | |
|---|---|---|
| FR | 369 993 | 1/1907 |
| FR | 2599156 | 5/1986 |
| FR | 2649605 | 1/1991 |
| GB | 1 026 839 | 4/1966 |
| GB | 1276003 | 6/1972 |
| JP | 62167343 A | 7/1987 |
| JP | 03-001857 | 1/1991 |
| JP | 04-158859 | 6/1992 |
| JP | 07-178125 | 7/1995 |
| JP | 07-265340 | 10/1995 |
| RU | 2138837 C1 | 9/1999 |
| SU | 1380743 A1 | 3/1998 |
| WO | WO 94/05232 | 3/1994 |
| WO | WO 94/23327 | 10/1994 |
| WO | WO 95/02356 | 1/1995 |
| WO | WO 95/03747 | 2/1995 |
| WO | WO 95/08135 | 3/1995 |
| WO | WO 97/48004 | 12/1997 |
| WO | WO 97/48005 | 12/1997 |
| WO | WO 99/07309 | 2/1999 |
| WO | WO 00/52516 A2 | 9/2000 |
| WO | WO 00/52516 A3 | 9/2000 |
| WO | WO 01/19364 | 3/2001 |
| WO | WO 02/027388 | 4/2002 |
| WO | WO 02/102241 A2 | 12/2002 |
| WO | WO 03/030763 A1 | 4/2003 |
| WO | WO 2004/050132 | 6/2004 |
| WO | WO 2004/105588 A2 | 12/2004 |

OTHER PUBLICATIONS

Accommodation responses to flickering stimuli. Chauhan et al. Ophthal. Physiol. Opt. vol. 16, No. 5, pp. 391-408, 1996.

Accommodation to perceived depth in stereotests. Koh et al. Ophthal. Physiol. Opt. vol. 18, No. 3, pp. 279-284, 1998.

Accommodative responses to anisoaccommodative targets. Koh et al. Ophthal. Physiol. Opt. vol. 18, No. 3, pp. 254-262, 1998.

Age Changes in the Interactions between the Accommodation and Vergence Systems. Heron et al. Optometry and Vision Science, vol. 78, No. 10, Oct. 2001.

Can Accommodation be Surgically Restored in Human Presbyopia? Glasser, Adrian. Optometry and Vision Science, vol. 76, No. 9, Sep. 1999.

Changes in the static accommodation response with age. Kalsi et al. Ophthal. Physiol. Opt. vol. 21, No. 1, pp. 77-84, 2001.

Dynamics of the accommodation response to abrupt changes in target vergence as a function of age. Heron et al. Vision Research 41 (2001) 507-519.

Eight Years Experience with Permalens Intracorneal Lenses in Non-human Primates. Werblin et al. Refractive & Corneal Surgery, vol. 8, Jan./Feb. 1992, pp. 12-21.
Errors in determining the direction of the visual axis in the presence of defocus. Atchison et al. Ophthal. Physiol. Opt., vol. 18, No. 5, pp. 463-467, 1998.
Holes in Clear Lenses Demonstrate a Pinhole Effect. Zacharia et al. Arch Ophthalmol, vol. 106, Apr. 1988, pp. 511-513.
International Search Report and Written Opinion of application No. PCT/US2005/038428, mailed Apr. 6, 2006.
Intra-Ocular Lenses and Implants. Choyce, Peter. Chpts. 4 & 17, 1964.
Near vision, lags of accommodation and myopia. Charman, W. N. Ophthal. Physiol. Opt., vol. 19, No. 2, pp. 126-133, 1999.
New Aspects in the Fitting of the Multi-Range Bifocal Contact Lens. Groppi, John J. Contacto 15, 1971, pp. 22-29.
On the linearity of accommodation dynamics. Charman, W. N. Vision Research 40 (2000) 2057-2066.
Perspectives in Refraction: Quantification of the Pinhole Effect. Miller et al. Survey of Ophthalmology, vol. 21, No. 4, Jan./Feb. 1997, pp. 347-350.
Retinal Image Quality in the Human Eye as a Function of the Accommodation. Lópex-Gil et al. Vision Research, vol. 38, No. 19, Jul. 3, 1998, pp. 1-11.
The controlled-pupil contact lens in low vision problems. Rosenbloom, Jr., Alfred A. Journal of the American Optometric Association, vol. 40, No. 8, Aug. 1969 pp. 836-840.
Use and Interpretation of the Pinhole Test. Takahashi, O.D., Ellen. The Optometric Weekly, 56(18); May 6, 1965 pp. 83-86.
Accommodation and acuity under night-driving illumination levels. Arumi et al. Opthal. Physiol. Opt. vol. 17, No. 4, pp. 291-299,1997.
Accommodation dynamics as a function of age. Heron et al. Opthal. Physiol. Opt. 2002 22:389-396.
Anterior Ciliary Sclerotomy for Treatment of Presbyopia: A Prospective Controlled Study. Hamilton et al. Ophthalmology, vol. 109, No. 11: Nov. 2002: pp. 1970-1977.
Binder et al., "Hydrogel keratophakia in non-human primates", Current Eye Research, vol. 1, No. 9, 1981/1982, pp. 535-542.
Cao et al., "Comparative study of the use of poly(glycolic acid), calcium alginate and pluronics in the engineering of autologous porcine cartilage", Polymers for Tissue Engineering, pp. 315-327, VSP 1998.
Choice of Spatial Frequency for Contrast Sensitivity Evaluation After Corneal Refractive Surgery. Montes-Mico et al. Journal of Refractive Surgery, vol. 17: Nov./Dec. 2001: pp. 646-651.
Choyce, P. "Implants with Coloured and Opaque Portions: Implants with Built-In Stenopeic Aperture," pp. 21-26 "Uniocular Aphakia Corrected by Anterior Chamber Implants with Built-In Stenipeic Aperture," pp. 132-136, 1964.
Clinical Characteristics of Lamellar Channel Deposits After Implementation of Intacs. Ruckhofer et al. J Cataract Refract Surg, vol. 26, Oct. 2000: pp. 1473-1479.
Corneal Topography: The State of the Art, Alignment of Videokeratographs. Mandell et al. Chpt. 2, pp. 17-23, Jan. 1995.
"Corneal Surgery" by L. Girard, The C.V. Mosby Publishing Company, London 1981 pp. 107-141.
Dynamic retinoscopy and accommodation. Whitefoot et al. Ophthal. Physiol. Opt. vol. 12, Jan. 1992, pp. 8-17.
Eduard Jaeger's Test-Types (Schrift-Scalen) and Historical Development of Vision Tests. Runge, Paul E. Tr. Am. Ophth. Soc. vol. 98, 2000: 375.
"Epikeratophakia: Techniques, Compositions, and Clinical Results" by Werblin, Opthalmology, 1983, pp. 45-58.
Evaluate surgical routine to determine DLK cause, surgeon advises. Piechocki, Michael. Ocular Surgery News: Refractive Surgery, Jan. 1, 2003: p. 14.
Explanation for the observation of isogyres in crystalline lenses viewed between crossed polarizers. Opthal. Physiol. Opt., vol. 13, Apr. 1993, pp. 209-211.
Flap Measurements With the Hansatome Microkeratome. Spadea et al. Journal of Refractive Surgery, vol. 18, Mar./Apr. 2002: pp. 149-154.

Focused and divided attention in stereoscopic deth. Wickens et al. SPIE, vol. 1256 Stereoscopic Displays and Applications (1990); pp. 28-34.
Griffith et al.; "Functional Human Corneal Equivalents Constructed from Cell Lines", Science, vol. 286, Dec. 10, 1999 pp. 2169-2172.
Human Visual System-Image Formation, Encyclopedia of Imaging Science and Technology, Roorda, A., 2002, pp. 539-557.
Hybrid diffractive-refractive achromatic spectacle lenses. Charman, W. N. Opthal. Physiol. Opt., vol. 14, Oct. 1994: pp. 389-392.
Iijima et al. "Formation of a spherical multicellular aggregate (spheroid) of animal cells in the pores of polyurethane foam as a cell culture substratum and its application to a hybrid artificial liver", Polymers for Tissue Engineering , pp. 273-286, VSP 1998.
Imaging in the 21st century. Charman, W. N. Ophthal. Physiol. Opt., vol. 18, No. 2, pp. 210-223,1998.
Intraocular pressure after excimer laser myopic refractive surgery. Montes-Mico et al. Ophthal. Physiol. Opt., vol. 21, No. 3, pp. 228-235, 2001.
Intrastromal Crystalline Deposits Following Hydrogel Keratophakia in Monkeys. Parks et al. Cornea12(1): 29-34,1993.
"Keratomileusis and Keratophakia in the Surgical Correction of Aphakia" by Barraquer, Cataract Surgery and Special Techniques, prior to 1996 pp. 270-289.
"Lamellar Corneal Stromectomy for the Operative Treatment of Myopia" by Tadeusz Krwawicz, Notes, Cases, Instruments—1964, pp. 828-833.
Lipid Deposits Posterior to Impermeable Intracornel Lenses in Rhesus Monkeys: Clinical, Histochemical, and Ultrastructural Studies. Rodrigues et al. Refractive & Corneal Surgery, vol. 6, Jan./Feb. 1990: DO. 32-37.
Mastel Precision: Fiber Optic Ring Illuminator (Product Nos. 3776 & 4050) US Patent No. 5312393 User Manual. Rev: A02: Jan. 11, 1995, pp. 1-25.
Mastel Precision: The Ring Light. http://www.mastel.com/ring_light.html. Jul. 28, 2003.
Measurement of the wave-front aberration of the eye by a fast psychophysical procedure. He et al. J. Opt. Soc. Am. A, vol. 15, No. 9: Sep. 1998, pp. 2449-2455.
Microstructural Changes in Polyester Biotextiles During Implantation in Humans. King et al. NC State University: JTATM, vol. 1, Issue 3, Spring 2001, pp. 1-8.
New Visual Acuity Charts for Clinical Research. Ferris et al. American Journal of Ophthalmology, 94: 91-96, 1982.
Night myopia and driving. Charman, W. N. Ophthal. Physiol. Opt., vol. 16, No. 6, p. 474-485, 1996.
Notch in contrast sensitivity function of optical origin: diffraction effects of acrylic filters. Irving et al. Ophthal. Physiol. Opt., vol. 13, Apr. 1993: pp. 179-182.
On modeling the causes of presbyopia. Glasser, A. Vision Research 41(2001) 3083-3087.
Optical Aspects of Tolerances to Uncorrected Ocular Astigmatism. Charman et al. Optometry and Vision Science, vol. 70, No. 2: pp. 111-117, 1993.
Optical Modeling of Contact Lens Performance Final Report Covering Period Jul. 15,1994-Mar. 31, 1995. Grivenkamp et al. for Pilkington Barnes Hind, Issued Apr. 5, 1995.
Optometric Clinical Practice Guideline Care of the Patient With Presbyopia: Reference Guide for Clinicians. Mancil et al. Mar. 20, 1998.
PCT/US04/16914 International Search Report and Written Opinion, dated Apr. 13, 2005, 9 pp.
PCT/US04/16914 Preliminary Report on Patentability, dated Dec. 15, 2005, 6 pp.
PermaVision intracorneallens shows promise for hyperopia. Kronemyer, Bob. Ocular Surgery News: Jan. 1, 2003; p. 8.
Perspectives in Refraction: Quantification of the Pinhole Effect. Miller et al. Survey of Ophthalmology, vol. 21, No. 4, Jan./Feb. 1977, pp. 347-350.
Sally Pobojewski, "New U-developed laser performs high-precision corneal surgery", News and Information Services, The University Record, Jul. 16, 1997.

Poly(methyl methacrylate) model study of optical surface quality after excimer laser photo refractive keratectomy. Hauge et al. J Cataract Refract Surg., vol. 27, Dec. 2001, pp. 2026-2035.

Procyon: Marketing Information for Distributors: Pupil Measurement and Refractive Surgery (Samples from Academic Papers 1994 and 2002). pp. 1-17.

"Refractive Keratoplasty: Acute Morphologic Features," by Baumgarter et al, The CLAO Journal-Apr. 1985, vol. II, No. 2, pp. 163-169.

Refractive keratoplasty with intrastromal hydrogel lenticular implants. McCarey et al. Invest. Ophthalmol. Vis. ScL, Jul. 1981, pp. 107-115.

Simple parametric model of the human ocular modulation transfer function, A. Deeley et al. Ophthal. Physiol. Opt., vol. 11, Jan. 1991, pp. 91-93.

Karin R. Slettin, Md et al., "An In Vivo Model of Femtosecond Laser Intrastromal Refractive Surgery", Experimental Science, Opthalmic Surgery and Lasers, Nov./Dec. 1999, vol. 30, No. 9, pp. 742-749.

Subjective Depth-of-Focus of the Eye. Atchison et al. Optometry and Vision Science, vol. 74, No. 7, Jul. 1997, pp. 511-520.

Subjective Sensitivity to Small Changes in the Contrast of a Suprathreshold Grating, The. Walsh et al. Vision Res., vol. 30, No. 1, pp. 163-193, 1990.

Surface Modification Properties of Parylene for Medical Applications, The. Wolgemuth, Lonny.Business Briefing: Medical Device Manufacturing & Technology 2002, pp. 1-4.

Surface tension control of collagen biomaterials by the selective hydrolysis of internal carboxyamides of the protein matrix. Revista Brasileira de Engenharia Biomedica, v. 15, n. 12, p. 55-61, jan/ago 1999.

Surgeon: Severe corneal lesions after LASIK are not stage 4 DLK. Piechocki, Michael. Ocular SurgeryNews; Jan. 1, 2003, pp. 16-17.

Swinger et al., "Keratophakia and Keratomileusis-Clinical Results", American Academy of Opthalmology, Aug. 1981, vol. 88, No. 8, pp. 709-715.

Theoretical and practical performance of a concentric bifocal intraocular implant lens. Charman, W.N. Vision Research 38 (1998) 2841-2853.

Use of a digital infrared pupillometer to assess patient suitability for refractive surgery. Rosen et al. J Cataract Refract Surg., vol. 28: Aug. 2002. pp. 1433-1438.

Vision and driving—a literature review and commentary. Charman, W.N. Ophthal. Physiol. Opt., vol. 17, No. 5, pp. 371-391, 1997.

Yamauchi et al., "Cultivation of fibroblast cells on keratin coated substrata", Polymers for Tissue Engineering, pp. 329-340, VS 1998.

* cited by examiner

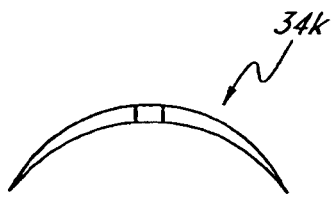
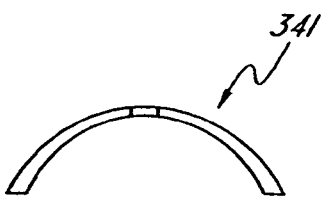
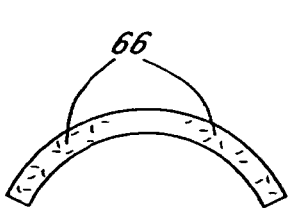
FIG. 17    FIG. 18    FIG. 19
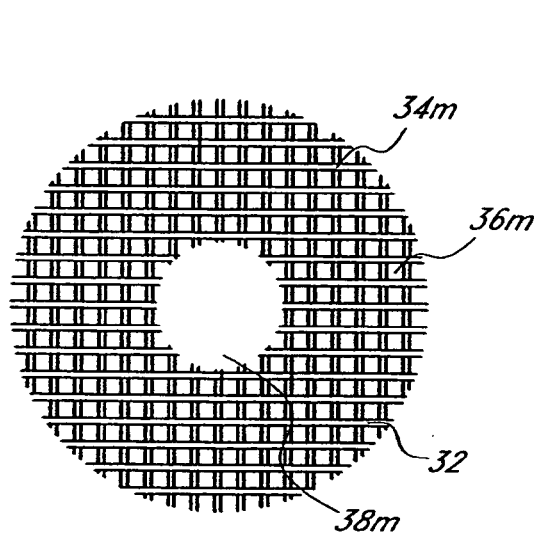
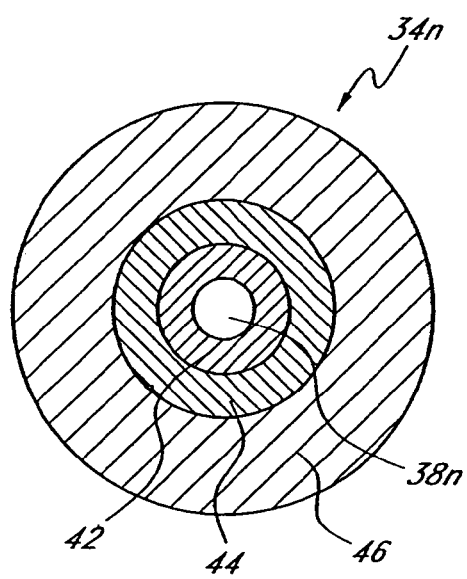
FIG. 20    FIG. 22
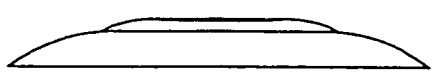
FIG. 21    FIG. 23

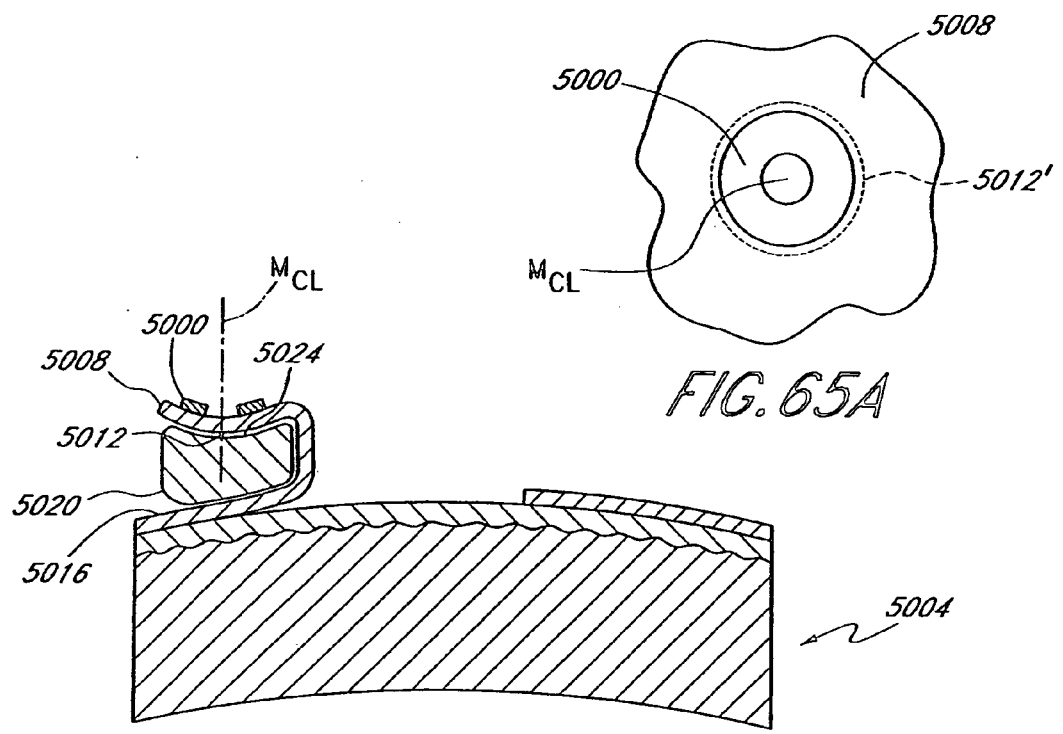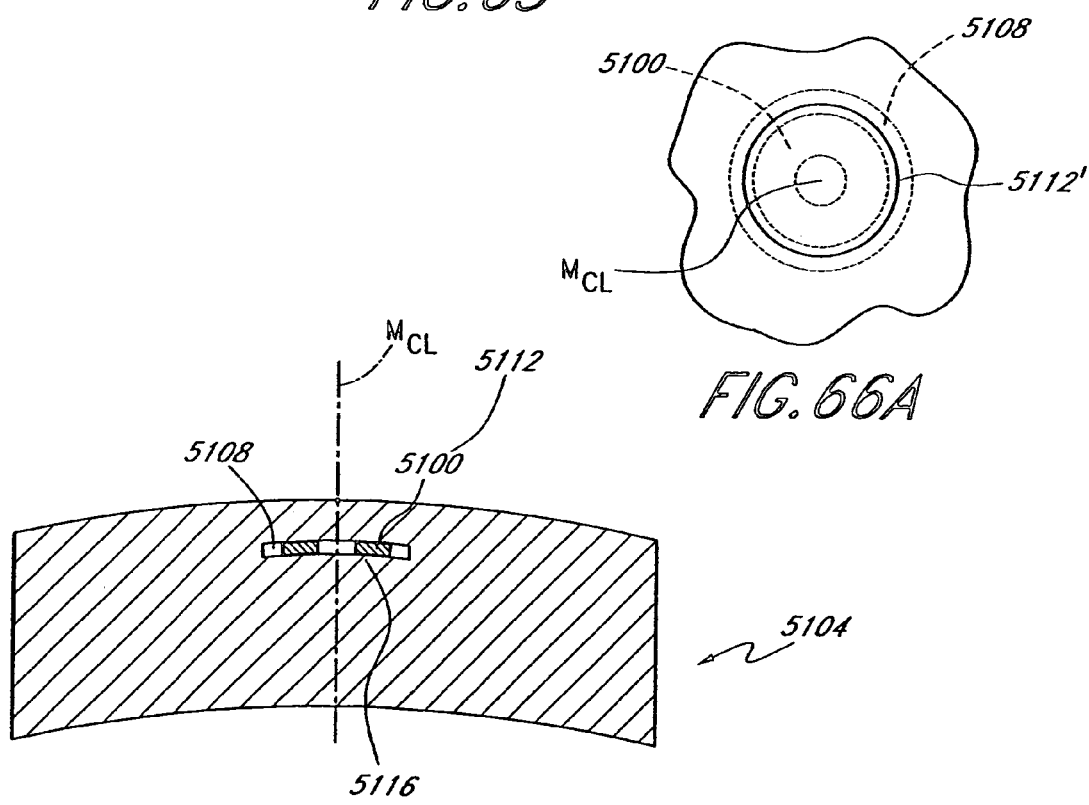

METHOD AND APPARATUS FOR ALIGNING A MASK WITH THE VISUAL AXIS OF AN EYE

RELATED APPLICATIONS

This application is a continuation of U.S. application Ser. No. 10/854,032, filed May 26, 2004 now abandoned, which claims priority under 35 U.S.C. §119(e) to U.S. Provisional Application No. 60/479,129, filed on Jun. 17, 2003, the entirety of which is hereby incorporated by reference.

BACKGROUND OF THE INVENTION

1. Field of the Invention

This application is directed to masks for improving the depth of focus of an eye of a human patient and methods and apparatuses for applying such masks. More particularly, this application is directed to apparatuses and methods for aligning a mask with the line of sight of an eye and applying the mask to the eye.

2. Description of the Related Art

Presbyopia, or the inability to clearly see objects up close is a common condition that afflicts many adults over the age of 40. Presbyopia diminishes the ability to see or read up close. Near objects appear blurry and out of focus. Presbyopia may be caused by defects in the focusing elements of the eye or the inability (due to aging) of the ciliary muscles to contract and relax and thereby control the shape of the lens in the eye.

The human eye functions by receiving light rays from an object and bending, refracting, and focusing those rays. The primary focusing elements of the human eye are the lens (also referred to as the intraocular lens) and the cornea. Light rays from an object are bent by the cornea, which is located in the anterior part of the eye. The light rays subsequently pass through the intraocular lens and are focused thereby onto the retina, which is the primary light receiving element of the eye. From the retina, the light rays are converted to electrical impulses, which are then transmitted by the optic nerves to the brain.

Ideally, the cornea and lens bend and focus the light rays in such a way that they converge at a single point on the retina. Convergence of the light rays on the retina produces a focused image. However, if the cornea or the lens are not functioning properly, or are irregularly shaped, the images may not converge at a single point on the retina. Similarly, the image may not converge at a single point on the retina if the muscles in the eye can no longer adequately control the lens. This condition is sometimes described as loss of accommodation. In presbyopic patients, for example, the light rays often converge at a point behind the retina. To the patient, the resulting image is out of focus and appears blurry.

Traditionally, vision improvement has been achieved by prescribing eye glasses or contact lenses to the patient. Eye glasses and contact lenses are shaped and curved to help bend light rays and improve focusing of the light rays onto the retina of the patient. However, some vision deficiencies, such as presbyopia, are not adequately addressed by these approaches.

SUMMARY OF THE INVENTION

In one embodiment, a method is provided for increasing the depth of focus of an eye of a patient. The eye has a visual axis. The visual axis of the eye is aligned with an instrument axis of an ophthalmic instrument. The ophthalmic instrument has an aperture through which the patient may look along the instrument axis. A first reference target is imaged on the instrument axis at a first distance with respect to the eye. A second reference target is imaged on the instrument axis at a second distance with respect to the eye. The second distance is greater than the first distance. Movement is provided such that the patient's eye is in a position where the images of the first and second reference targets appear to the patient's eye to be aligned. A mask comprising a pin-hole aperture having a mask axis is aligned with the instrument axis such that the mask axis and the instrument axis are substantially collinear. The mask is applied to the eye of the patient while the alignment of the mask and the instrument axis is maintained.

In another embodiment, a method for increasing the depth of focus of an eye of a patient is provided. The eye includes a visual axis and a cornea that has an epithelial sheet, a Bowman's membrane, and a stroma. The visual axis of the eye is located using more than one reference target. A mask that includes a pin-hole aperture having a mask axis is aligned with the visual axis of the eye. The mask is applied to the eye while maintaining the alignment of the mask axis and the visual axis.

In another embodiment, a method for correcting vision is provided. A LASIK procedure is performed. The eye is moved until at least two reference targets are aligned. A mask is applied to the eye.

In another embodiment, an apparatus for aligning a mask with a visual axis of an eye of a patient includes an optics housing, a first target, a second target, a lens, and a light source. The optics housing defines an aperture at a first location into which the eye may be directed and an instrument axis. The first target is coupled with the optics housing and is positioned on the instrument axis at a first distance relative to the first location. The second target is coupled with the optics housing and is positioned on the instrument axis at a second distance relative to the first location. The lens is coupled with the optics housing. The second distance is equal to the focal length of the lens. The light source is off-set from the instrument axis and is configured to indicate the location of the visual axis of the eye.

In another embodiment, an apparatus for aligning a mask with a visual axis of an eye of a patient includes a fixture for locating the eye at a first location. The apparatus for aligning also includes a first target, a second target, and a marker. The first target is positioned on an instrument axis at a first distance relative to the first location. The second target is positioned on the instrument axis at a second distance relative to the first location. The marker is configured to indicate the location of the instrument axis.

In another embodiment, a method of treating a patient is provided. A reference point on a cornea is identified. The reference point is marked. A corneal flap is lifted to expose an intracorneal surface. An implant is positioned on the intracorneal surface. The flap is closed to cover at least a portion of the implant.

In another embodiment, a method of treating a patient is provided. A reference point on a cornea is identified. The reference point is marked. A corneal pocket is created to expose an intracorneal surface. An implant is positioned on the intracorneal surface.

In another embodiment, a method of treating a patient is provided. A reference point on a cornea is identified. The reference point is marked. A stromal surface is exposed. An implant is positioned on the stromal surface. At least a portion of the implant is covered.

In one embodiment, a mask configured to be implanted in a cornea of a patient to increase the depth of focus of the patient includes an anterior surface, a posterior surface, and a plurality of holes. The anterior surface is configured to reside adjacent a first corneal layer. The posterior surface is configured to reside adjacent a second corneal layer. The plurality of holes extends at least partially between the anterior surface and the posterior surface. The plurality of holes is configured to substantially eliminate visible diffraction patterns.

In another embodiment, a mask configured to be implanted in a cornea of a patient to increase the depth of focus of the patient is provided. The mask includes a body that has an anterior surface configured to reside adjacent a first corneal layer and a posterior surface configured to reside adjacent a second corneal layer. The body is formed of a substantially opaque material that has a relatively high water content. The body is capable of substantially maintaining natural nutrient flow from the first corneal layer to the second corneal layer. The body being is configured to substantially eliminate diffraction patterns that are visible to the patient.

In another embodiment, a method of making a mask is provided. A body is configured to have an anterior surface capable of residing adjacent a first layer of a cornea of a patient and a posterior surface capable of residing adjacent a second layer of the cornea. A peripheral portion of the body is configured to be substantially opaque to incident light. A central portion of the body is configured to be transparent along an optic axis to substantially all of the incident light. The body is configured with a transport structure capable of substantially maintaining natural nutrient flow from the first layer to the second layer without producing visible diffraction patterns.

In another embodiment, a method of making a mask is provided. A body that has an anterior surface, a posterior surface, an outer periphery, and an inner periphery is provided. The anterior surface is configured to reside adjacent a first layer of a cornea of a patient. The posterior surface is configured to reside adjacent a second layer of the cornea. A plurality of non-uniform locations for forming a plurality of holes between the anterior surface and the posterior surface is generated. A subset of locations among the plurality of locations is modified to maintain a performance characteristic of the mask. A hole is formed in the body at locations corresponding to the subset of locations. The holes are configured to substantially maintain natural nutrient flow from the first layer to the second layer without producing visible diffraction patterns.

BRIEF DESCRIPTION OF THE DRAWINGS

FIG. 17 is a side view of an embodiment of a convex mask.
FIG. 18 is a side view of an embodiment of a concave mask.
FIG. 19 is a side view of an embodiment of a mask with a gel to provide opacity to the lens.
FIG. 20 is frontal plan view of an embodiment of a mask with a weave of polymeric fibers.
FIG. 21 is a side view of the mask of FIG. 20.
FIG. 22 is a front plan view of an embodiment of a mask having regions of varying opacity.
FIG. 23 is a side view of the mask of FIG. 22.

FIG. 55B is a top view of the fixation target of FIG. 55A showing the

FIG. 55C is a top view of the fixation target of FIG. 55A showing the

FIG. 65 is a cross-sectional view of an eye illustrating a treatment of a patient wherein a flap is opened to place an implant and a location is marked for placement of the implant.

FIG. 65A is a partial plan view of the eye of FIG. 65 wherein an implant has been applied to a corneal flap and positioned with respect to a ring.

FIG. 66 is a cross-sectional view of an eye illustrating a treatment of a patient wherein a pocket is created to place an implant and a location is marked for placement of the implant.

FIG. 66A is a partial plan view of the eye of FIG. 66 wherein an implant has been positioned in a pocket and positioned with respect to a ring.

DETAILED DESCRIPTION OF THE PREFERRED EMBODIMENT

This application is directed to masks for improving the depth of focus of an eye of a patient and methods and apparatuses for applying such masks. The masks generally employ pin-hole vision correction and have nutrient transport structures. The masks may be applied to the eye in any manner and in any location, e.g., as an implant in the cornea (sometimes referred to as a "corneal inlay"). The masks can also be embodied in or combined with lenses and applied in other regions of the eye, e.g., as or in combination with a contact lenses or an intraocular lenses. Apparatuses and methods for applying the masks to the patient generally use the patient's vision to locate the patient's line of sight while the mask is being applied to the eye so that the mask may be properly aligned with the line of sight.

I. Overview of Pin-Hole Vision Correction

A mask that has a pinhole aperture may be used to improve the depth of focus of a human eye. As discussed above, presbyopia is a problem of the human eye that commonly occurs in older human adults wherein the ability to focus becomes limited to inadequate range. FIGS. 1-6 illustrate how presbyopia interferes with the normal function of the eye and how a mask with a pinhole aperture mitigates the problem.

Figure 1:
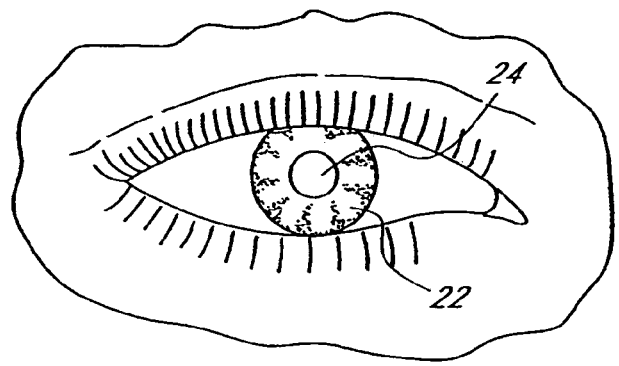
FIG. 1 is a plan view of the human eye.
Figure 2:
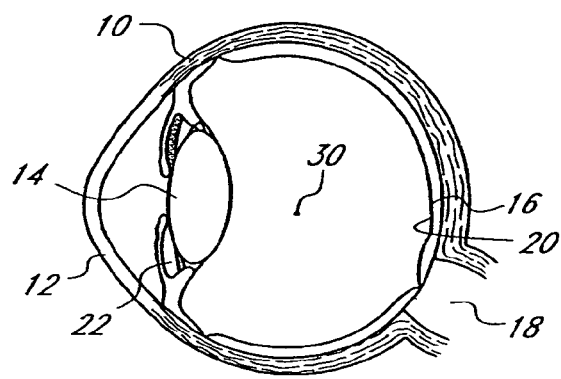
FIG. 2 is a cross-sectional side view of the human eye.

FIG. 1 shows the human eye, and FIG. 2 is a side view of the eye 10. The eye 10 includes a cornea 12 and an intraocular lens 14 posterior to the cornea 12. The cornea 12 is a first focusing element of the eye 10. The intraocular lens 14 is a second focusing element of the eye 10. The eye 10 also includes a retina 16, which lines the interior of the rear surface of the eye 10. The retina 16 includes the receptor cells which are primarily responsible for the sense of vision. The retina 16 includes a highly sensitive region, known as the macula, where signals are received and transmitted to the visual centers of the brain via the optic nerve 18. The retina 16 also includes a point with particularly high sensitivity 20, known as the fovea. As discussed in more detail in connection with FIG. 8, the fovea 20 is slightly offset from the axis of symmetry of the eye 10.

Figures 7, 8, 9:
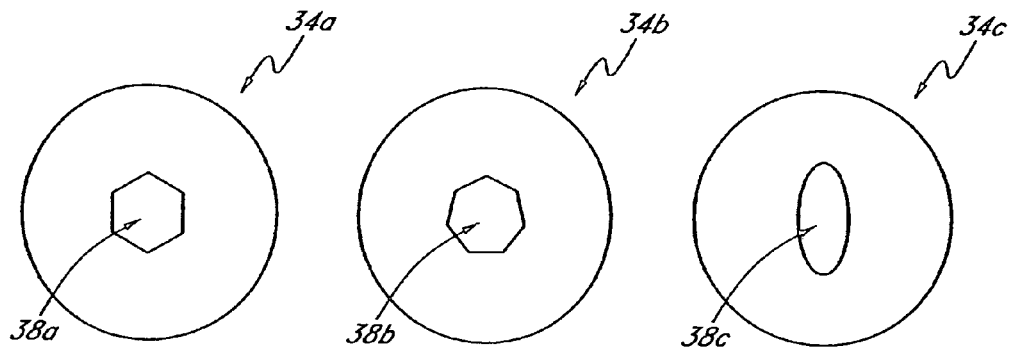
FIG. 7 is a plan frontal view of an embodiment of a mask with a hexagon-shaped pinhole like aperture.
FIG. 8 is a plan frontal view of an embodiment of a mask with an octagon-shaped pinhole like aperture.
FIG. 9 is a frontal plan view of an embodiment of a mask with an oval-shaped pinhole like aperture.

The eye 10 also includes a ring of pigmented tissue known as the iris 22. The iris 22 includes smooth muscle for controlling and regulating the size of an opening 24 in the iris 22, which is known as the pupil. An entrance pupil 26 is seen as the image of the iris 22 viewed through the cornea 12 (See FIG. 7). A central point of the entrance pupil 28 is illustrated in FIG. 7 and will be discussed further below.

The eye 10 resides in an eye-socket in the skull and is able to rotate therein about a center of rotation 30.

Figure 3:
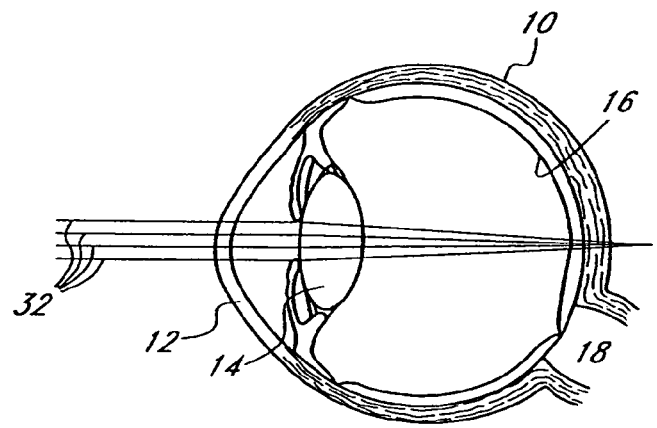
FIG. 3 is a cross-sectional side view of the human eye of a presbyopic patient wherein the light rays converge at a point behind the retina of the eye.

FIG. 3 shows the transmission of light through the eye 10 of a presbyotic patient. Due to either an aberration in the cornea 12 or the intraocular lens 14, or loss of muscle control, light rays 32 entering the eye 10 and passing through the cornea 12 and the intraocular lens 14 are refracted in such a way that the light rays 32 do not converge at a single focal point on the retina 16. FIG. 3 illustrates that in a presbyotic patient, the light rays 32 often converge at a point behind the retina 16. As a result, the patient experiences blurred vision.

Figure 4:
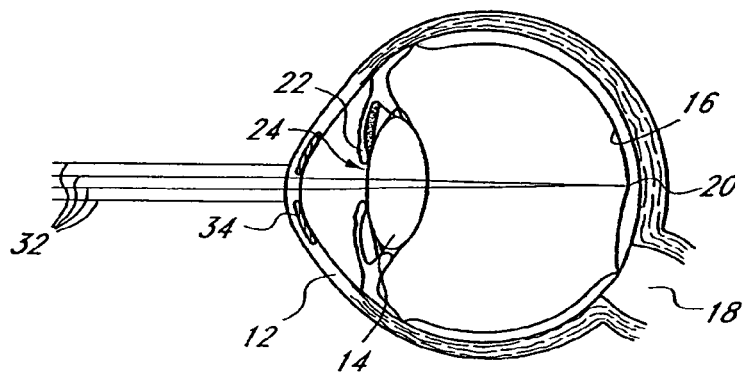
FIG. 4 is a cross-sectional side view of a presbyopic eye implanted with one embodiment of a mask wherein the light rays converge at a point on the retina.
Figure 5:
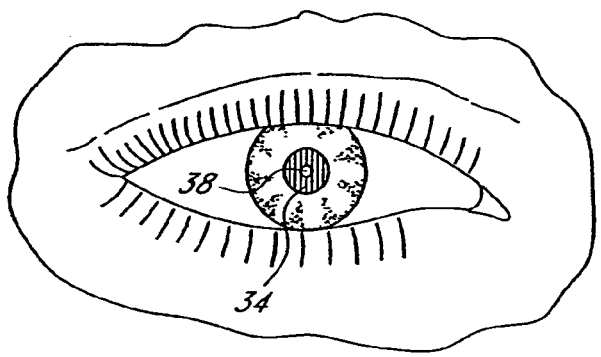
FIG. 5 is a plan view of the human eye with a mask applied thereto.

Turning now to FIG. 4, there is shown the light transmission through the eye 10 to which a mask 34 has been applied. The mask 34 is shown implanted in the cornea 12 in FIG. 4. However, as discussed below, it will be understood that the mask 34 can be, in various modes of application, implanted in the cornea 12 (as shown), used as a contact lens placed over the cornea 12, incorporated in the intraocular lens 14 (including the patient's original lens or an implanted lens), or otherwise positioned on or in the eye 10. In the illustrated embodiment, the light rays 32 that pass through the mask 34, the cornea 12, and the lens 14 converge at a single focal point on the retina 16. The light rays 32 that would not converge at the single point on retina 16 are blocked by the mask 34. As discussed below, it is desirable to position the mask 34 on the eye 10 so that the light rays 32 that pass through the mask 34 converge at the fovea 20.

Figure 6:
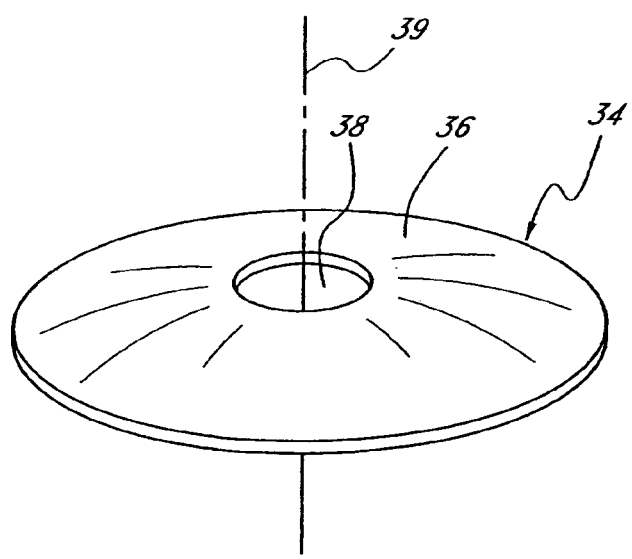
FIG. 6 is a perspective view of one embodiment of a mask.

Turning now to FIG. 6, there is shown one embodiment of the mask 34. As seen, the mask 34 preferably includes an annular region 36 surrounding a pinhole opening or aperture 38 substantially centrally located on the mask 34. The pinhole aperture 38 is generally located around a central axis 39, referred to herein as the optical axis of the mask 34. The pinhole aperture 38 preferably is in the shape of a circle. It has been reported that a circular aperture, such as the aperture 38 may, in some patients, produce a so-called "halo effect" where the patient perceives a shimmering image around the object being viewed. Accordingly, it may be desirable to provide an aperture 38 in a shape that diminishes, reduces, or completely eliminates the so-called "halo effect."

II. Masks Employing Pin-Hole Correction

Figures 10, 11, 12:
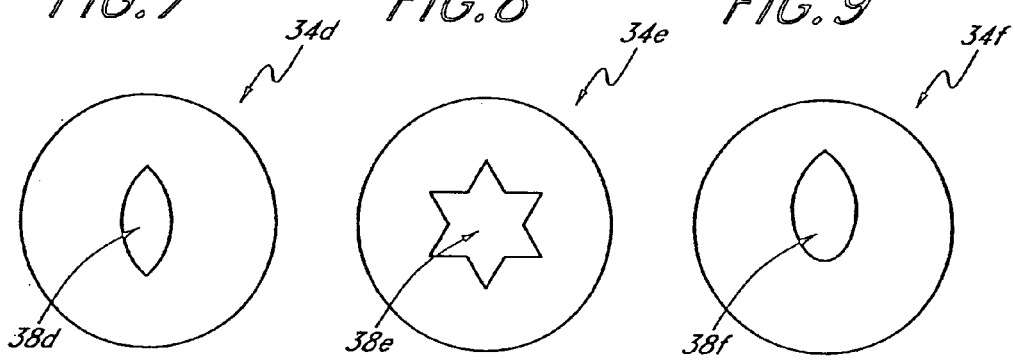
FIG. 10 is a frontal plan view of an embodiment of a mask with a pointed oval-shaped pinhole like aperture.
FIG. 11 is a frontal plan view of an embodiment of a mask with a star-shaped pinhole like aperture.
FIG. 12 is a frontal plan view of an embodiment of a mask with a teardrop-shaped pinhole like aperture spaced above the true center of the mask.

FIGS. 7-42 illustrate a variety of embodiments of masks that can improve the vision of a patient with presbyopia. The masks described in connection with FIG. 7-42 are similar to the mask 34, except as set forth below. Accordingly, the masks described in connection with FIGS. 7-42 can be used and applied to the eye 10 of a patient in a similar fashion to the mask 34. For example, FIG. 7 shows an embodiment of a mask 34a that includes an aperture 38a formed in the shape of a hexagon. FIG. 8 shows another embodiment of a mask 34b that includes an aperture 38b formed in the shape of an octagon. FIG. 9 shows another embodiment of a mask 34c that includes an aperture 38c formed in the shape of an oval, while FIG. 10 shows another embodiment of a mask 34d that includes an aperture 38d formed in the shape of a pointed oval. FIG. 11 shows another embodiment of a mask 34e wherein the aperture 38e is formed in the shape of a star or starburst.

Figures 13, 14, 15:
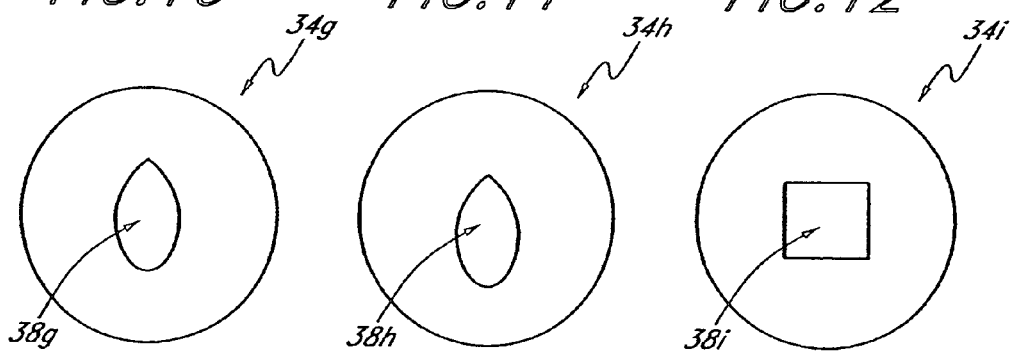
FIG. 13 is a frontal plan view of an embodiment of a mask with a teardrop-shaped pinhole like aperture centered within the mask.
FIG. 14 is a frontal plan view of an embodiment of a mask with a teardrop-shaped pinhole like aperture spaced below the true center of the mask.
FIG. 15 is a frontal plan view of an embodiment of a mask embodying with a square-shaped pinhole like aperture.

FIGS. 12-14 illustrate further embodiments that have tear-drop shaped apertures. FIG. 12 shows a mask 34f that has a tear-drop shaped aperture 38f that is located above the true center of the mask 34f. FIG. 13 shows a mask 34g that has a tear-drop shaped aperture 38g that is substantially centered in the mask 34g. FIG. 14 shows a mask 34h that has a tear-drop shaped aperture 38h that is below the true center of the mask 34h. FIG. 12-14 illustrate that the position of aperture can be tailored, e.g., centered or off-center to provide different effects. For example, an aperture that is located below the true center of a mask generally will allow more light to enter the eye because the upper portion of the aperture 34 will not be covered by the eyelid of the patient. Conversely, where the aperture is located above the true center of the mask, the aperture may be partially covered by the eyelid. Thus, the above-center aperture may permit less light to enter the eye.

Figure 16:
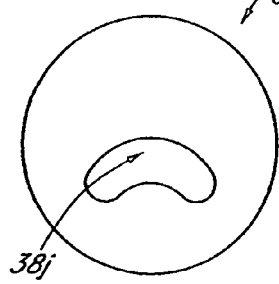
FIG. 16 is a frontal plan view of an embodiment of a mask with a kidney-shaped oval pinhole like aperture.

FIG. 15 shows an embodiment of a mask 34i that includes an aperture 38i formed in the shape of a square. FIG. 16 shows an embodiment of a mask 34j that has a kidney-shaped aperture 38j. It will be appreciated that the apertures shown in FIGS. 7-16 are merely exemplary of non-circular apertures. Other shapes and arrangements may also be provided and are within the scope of the present invention.

The mask 34 preferably has a constant thickness, as discussed below. However, in some embodiments, the thickness of the mask may vary between the inner periphery (near the aperture 38) and the outer periphery. FIG. 17 shows a mask 34k that has a convex profile, i.e., that has a gradually decreasing thickness from the inner periphery to the outer periphery. FIG. 18 shows a mask 34l that has a concave profile, i.e., that has a gradually increasing thickness from the inner periphery to the outer periphery. Other cross-sectional profiles are also possible.

The annular region 36 is at least partially and preferably completely opaque. The opacity of the annular region 36 prevents light from being transmitted through the mask 32 (as generally shown in FIG. 4). Opacity of the annular region 36 may be achieved in any of several different ways.

For example, in one embodiment, the material used to make mask 34 may be naturally opaque. Alternatively, the material used to make the mask 34 may be substantially clear, but treated with a dye or other pigmentation agent to render region 36 substantially or completely opaque. In still another example, the surface of the mask 34 may be treated physically or chemically (such as by etching) to alter the refractive and transmissive properties of the mask 34 and make it less transmissive to light.

In still another alternative, the surface of the mask 34 may be treated with a particulate deposited thereon. For example, the surface of the mask 34 may be deposited with particulate of titanium, gold or carbon to provide opacity to the surface of the mask 34. In another alternative, the particulate may be encapsulated within the interior of the mask 34, as generally shown in FIG. 19. Finally, the mask 34 may be patterned to provide areas of varying light transmissivity, as generally shown in FIGS. 24-33, which are discussed in detail below.

Turning to FIG. 20, there is shown a mask 34m formed or made of a woven fabric, such as a mesh of polyester fibers. The mesh may be a cross-hatched mesh of fibers. The mask 34m includes an annular region 36m surrounding an aperture 38m. The annular region 36m comprises a plurality of generally regularly positioned apertures 36m in the woven fabric allow some light to pass through the mask 34m. The amount of light transmitted can be varied and controlled by, for example, moving the fibers closer together or farther apart, as desired. Fibers more densely distributed allow less light to pass through the annular region 36m. Alternatively, the thickness of fibers can be varied to allow more or less light through the openings of the mesh. Making the fiber strands larger results in the openings being smaller.

FIG. 22 shows an embodiment of a mask 34n that includes an annular region 36n that has sub-regions with different opacities. The opacity of the annular region 36n may gradually and progressively increase or decrease, as desired. FIG. 22 shows one embodiment where a first area 42 closest to an aperture 38n has an opacity of approximately 60%. In this embodiment, a second area 44, which is outlying with respect to the first area 42, has a greater opacity, such as 70%. In this embodiment, a third area 46, which is outlying with respect to the second area 42, has an opacity of between 85 to 100%. The graduated opacity of the type described above and shown in FIG. 22 is achieved in one embodiment by, for example, providing different degrees of pigmentation to the areas 42, 44 and 46 of the mask 34n. In another embodiment, light blocking materials of the type described above in variable degrees may be selectively deposited on the surface of a mask to achieve a graduated opacity.

In another embodiment, the mask may be formed from co-extruded rods made of material having different light transmissive properties. The co-extruded rod may then be sliced to provide disks for a plurality of masks, such as those described herein.

Figure 24:
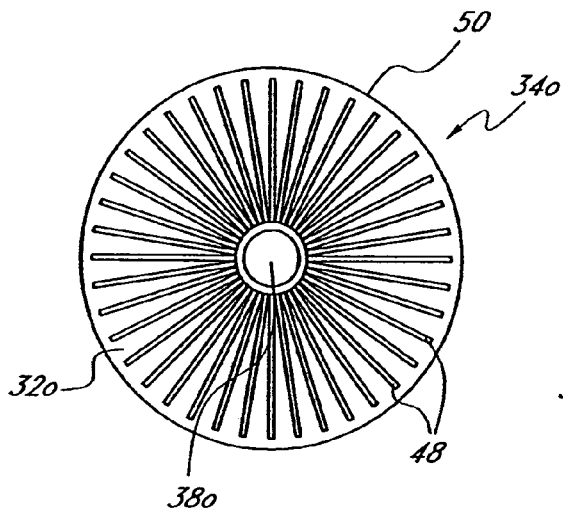
FIG. 24 is a frontal plan view of an embodiment of a mask that includes a centrally located pinhole like aperture and radially extending slots emanating from the center to the periphery of the mask.

FIGS. 24-33 shows examples of masks that have been modified to provide regions of differing opacity. For example, FIG. 24 shows a mask 34o that includes an aperture 38o and a plurality of cutouts 48 in the pattern of radial spokes extending from near the aperture 38o to an outer periphery 50 of the mask 34o. FIG. 24 shows that the cutouts 48 are much more densely distributed about a circumference of the mask near aperture 38o than are the cutouts 48 about a circumference of the mask near the outer periphery 50. Accordingly, more light passes through the mask 34o nearer aperture 38o than near the periphery 50. The change in light transmission through the mask 34o is gradual.

Figure 26:
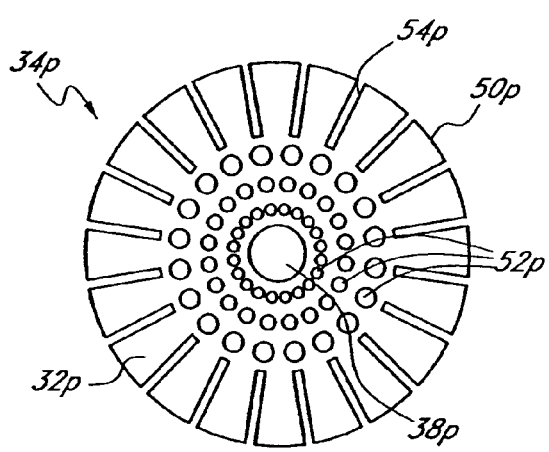
FIG. 26 is a frontal plan view of an embodiment of a mask that includes a central pinhole like aperture, surrounded by a plurality of holes radially spaced from the pinhole like aperture and slots extending radially spaced from the holes and extending to the periphery of the mask.
Figure 27:
FIG. 27 is a side view of the mask of FIG. 26.

FIGS. 26-27 show another embodiment of a mask 34p. The mask 34p includes an aperture 38p and a plurality of circular cutouts 52p, and a plurality of cutouts 54p. The circular cutouts 52p are located proximate the aperture 38p. The cutouts 54p are located between the circular cutouts 52p and the periphery 50p. The density of the circular cutouts 52p generally decreases from the near the aperture 38p toward the periphery 50p. The periphery 50p of the mask 34p is scalloped by the presence of the cutouts 54, which extend inward from the periphery 50p, to allow some light to pass through the mask at the periphery 50p.

Figure 28:
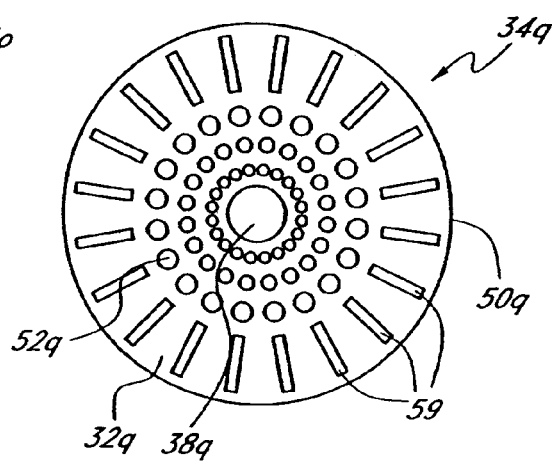
FIG. 28 is a frontal plan view of an embodiment of a mask that includes a central pinhole like aperture, a region that includes a plurality of holes radially spaced from the aperture, and a region that includes rectangular slots spaced radially from the holes.
Figure 25:
FIG. 25 is a side view of the mask of FIG. 24.
Figure 29:
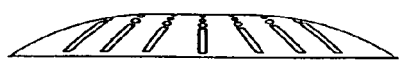
FIG. 29 is a side view of the mask of FIG. 28.

FIGS. 28-29 shows another embodiment similar to that of FIGS. 26-27 wherein a mask 34q includes a plurality of circular cutouts 52q and a plurality of cutouts 54q. The cutouts 54q are disposed along the outside periphery 50q of the mask 34q, but not so as to provide a scalloped periphery.

Figure 30:
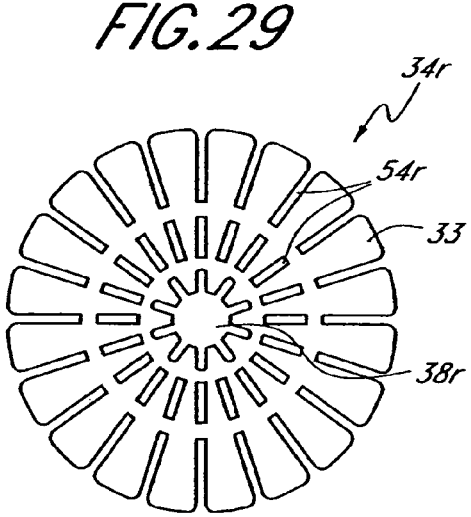
FIG. 30 is a frontal plan view of an embodiment of a mask that includes a non-circular pinhole like aperture, a first set of slots radially spaced from the aperture, and a region that includes a second set of slots extending to the periphery of the mask and radially spaced from the first set of slots.
Figure 31:
FIG. 31 is a side view of the mask of FIG. 30.

FIGS. 30 and 31 illustrate an embodiment of a mask 34r that includes an annular region 36r that is patterned and an aperture 38r that is non-circular. As shown in FIG. 30, the aperture 38r is in the shape of a starburst. Surrounding the aperture 38r is a series of cutouts 54r that are more densely spaced toward the aperture 38r. The mask 34r includes an outer periphery 50r that is scalloped to provide additional light transmission at the outer periphery 50r.

Figure 32:
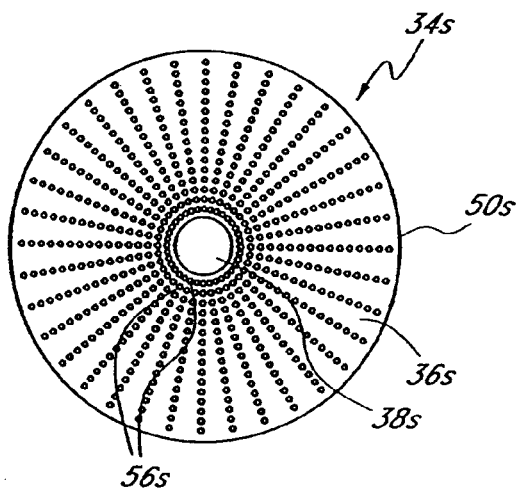
FIG. 32 is a frontal plan view of an embodiment of a mask that includes a central pinhole like aperture and a plurality of holes radially spaced from the aperture.
Figure 33:
FIG. 33 is a side view of the mask of FIG. 32.

FIGS. 32 and 33 show another embodiment of a mask 34s that includes an annular region 36s and an aperture 38s. The annular region 36s is located between an outer periphery 50s of the mask 34s and the aperture 38s. The annular region 36s is patterned. In particular, a plurality of circular openings 56s is distributed over the annular region 36s of the mask 34s. It will be appreciated that the density of the openings 56s is greater near the aperture 38s than near the periphery 50s of the mask 34s. As with the examples described above, this results in a gradual increase in the opacity of the mask 34s from aperture 38s to periphery 50s.

Figure 34:
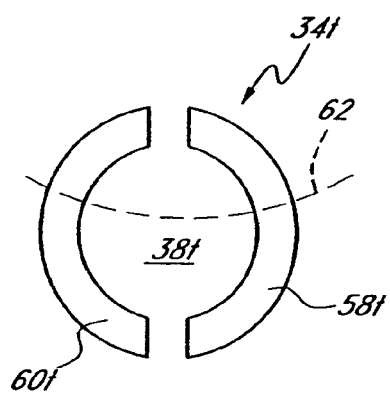
FIG. 34 is an embodiment of a mask that includes two semi-circular mask portions.
Figure 35:
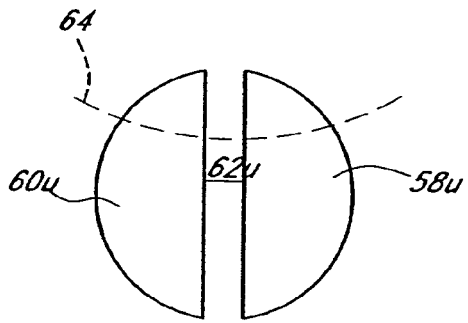
FIG. 35 is an embodiment of a mask that includes a half-moon shaped region and a centrally-located pinhole like aperture.
Figure 36:
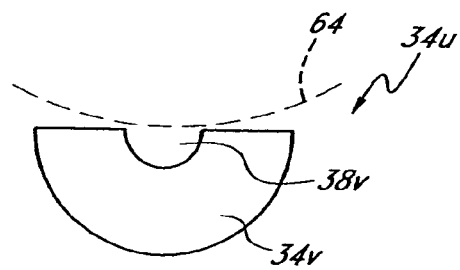
FIG. 36 is an embodiment of a mask including two half-moon shaped portions.
Figure 40:
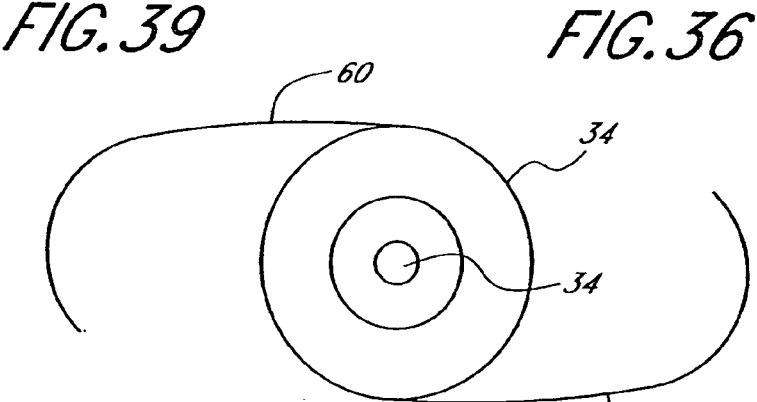
FIG. 40 is another an embodiment of a mask that includes connectors for securing the mask within the eye.

FIGS. 34-36 show further embodiments. In particular, FIG. 34 shows a mask 34t that includes a first mask portion 58t and a second mask portion 60t. The mask portions 58t, 60t are generally "C-shaped." As shown in FIG. 34, the mask portions 58t, 60t are implanted or inserted such that the mask portions 58t, 60t define a pinhole or aperture 38t.

FIG. 35 shows another embodiment wherein a mask 34u includes two mask portions 58u, 60u. Each mask portion 58u, 60u is in the shape of a half-moon and is configured to be implanted or inserted in such a way that the two halves define a central gap or opening 62u, which permits light to pass therethrough. Although opening 62u is not a circular pinhole, the mask portions 58u, 60u in combination with the eyelid (shown as dashed line 64) of the patient provide a comparable pinhole effect.

FIG. 36 shows another embodiment of a mask 34v that includes an aperture 38v and that is in the shape of a half-moon. As discussed in more detail below, the mask 34v may be implanted or inserted into a lower portion of the cornea 12 where, as described above, the combination of the mask 34v and the eyelid 62 provides the pinhole effect.

Other embodiments employ different ways of controlling the light transmissivity through a mask. For example, the mask may be a gel-filled disk, as shown in FIG. 19. The gel may be a hydrogel or collagen, or other suitable material that is biocompatible with the mask material and can be introduced into the interior of the mask. The gel within the mask may include particulate 66 suspended within the gel. Examples of suitable particulate are gold, titanium, and carbon particulate, which, as discussed above, may alternatively be deposited on the surface of the mask.

The material of the mask 34 may be any biocompatible polymeric material. Where a gel is used, the material is suitable for holding a gel. Examples of suitable materials for the mask 34 include the preferred polymethylmethacrylate or other suitable polymers, such as polycarbonates and the like. Of course, as indicated above, for non-gel-filled materials, a preferred material may be a fibrous material, such as a Dacron mesh.

The mask 34 may also be made to include a medicinal fluid, such as an antibiotic that can be selectively released after application, insertion, or implantation of the mask 34 into the eye of the patient. Release of an antibiotic after application, insertion, or implantation provides faster healing of the incision. The mask 34 may also be coated with other desired drugs or antibiotics. For example, it is known that cholesterol deposits can build up on the eye. Accordingly, the mask 34 may be provided with a releasable cholesterol deterring drug. The drug may be coated on the surface of the mask 34 or, in an alternative embodiment, incorporated into the polymeric material (such as PMMA) from which the mask 34 is formed.

Figure 37:
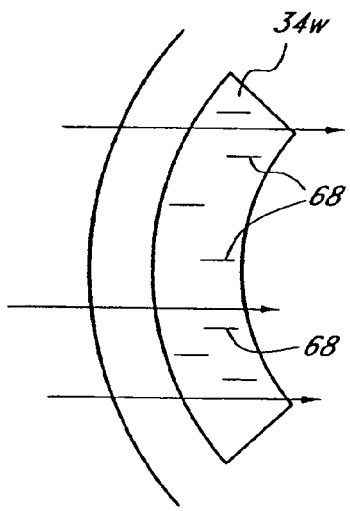
FIG. 37 is a enlarged, diagrammatic view of an embodiment of a mask that includes particulate structure adapted for selectively controlling light transmission through the mask in a high light environment.
Figure 38:
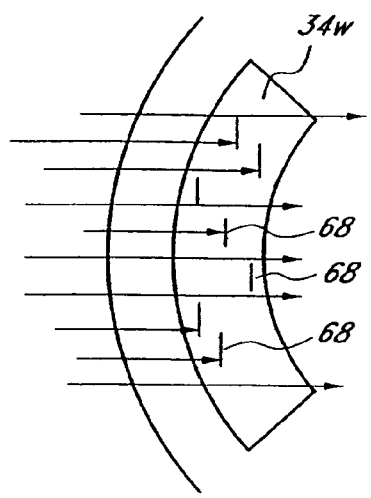
FIG. 38 is a view of the mask of FIG. 37 in a low light environment.

FIGS. 37 and 38 illustrate one embodiment where a mask 34w comprises a plurality of nanites 68. "Nanites" are small particulate structures that have been adapted to selectively transmit or block light entering the eye of the patient. The particles may be of a very small size typical of the particles used in nanotechnology applications. The nanites 68 are suspended in the gel or otherwise inserted into the interior of the mask 34w, as generally shown in FIGS. 37 and 38. The nanites 68 can be preprogrammed to respond to different light environments.

Thus, as shown in FIG. 37, in a high light environment, the nanites 68 turn and position themselves to substantially and selectively block some of the light from entering the eye. However, in a low light environment where it is desirable for more light to enter the eye, nanites may respond by turning or be otherwise positioned to allow more light to enter the eye, as shown in FIG. 38.

Nano-devices or nanites are crystalline structures grown in laboratories. The nanites may be treated such that they are receptive to different stimuli such as light. In accordance with one aspect of the present invention, the nanites can be imparted with energy where, in response to a low light and high light environments, they rotate in the manner described above and generally shown in FIG. 38.

Nanoscale devices and systems and their fabrication are described in Smith et al., "Nanofabrication," Physics Today, February 1990, pp. 24-30 and in Craighead, "Nanoelectromechanical Systems," Science, Nov. 24, 2000, Vol. 290, pp. 1532-1535, both of which are incorporated by reference herein in their entirety. Tailoring the properties of small-sized particles for optical applications is disclosed in Chen et al. "Diffractive Phase Elements Based on Two-Dimensional Artificial Dielectrics," Optics Letters, Jan. 15, 1995, Vol. 20, No.2, pp.121-123, also incorporated by reference herein in its entirety.

Figure 39:
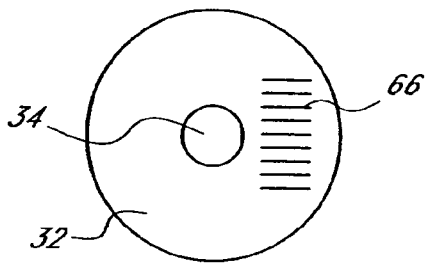
FIG. 39 is an embodiment of a mask that includes a barcode formed on the annular region of the mask.

Masks 34 made in accordance with the present invention may be further modified to include other properties. FIG. 39 shows one embodiment of a mask 34x that includes a bar code 70 or other printed indicia.

The masks described herein may be incorporated into the eye of a patient in different ways. For example, as discussed in more detail below in connection with FIG. 52, the mask 34 may be provided as a contact lens placed on the surface of the eyeball 10. Alternatively, the mask 34 may be incorporated in an artificial intraocular lens designed to replace the original lens 14 of the patient. Preferably, however, the mask 34 is provided as a corneal implant or inlay, where it is physically inserted between the layers of the cornea 12.

When used as a corneal implant, layers of the cornea 12 are peeled away to allow insertion of the mask 34. Typically, the optical surgeon (using a laser) cuts away and peels away a flap of the overlying corneal epithelium. The mask 34 is then inserted and the flap is placed back in its original position where, over time, it grows back and seals the eyeball. In some embodiments, the mask 34 is attached or fixed to the eye 10 by support strands 72 and 74 shown in FIG. 40 and generally described in U.S. Pat. No. 4,976,732, incorporated by reference herein in its entirety.

In certain circumstances, to accommodate the mask 34, the surgeon may be required to remove additional corneal tissue. Thus, in one embodiment, the surgeon may use a laser to peel away additional layers of the cornea 12 to provide a pocket that will accommodate the mask 34. Application of the mask 34 to the cornea 12 of the eye 10 of a patient is described in greater detail in connection with FIGS. 53A-54C.

Removal of the mask 34 may be achieved by simply making an additional incision in the cornea 12, lifting the flap and removing the mask 34. Alternatively, ablation techniques may be used to completely remove the mask 34.

Figure 41:
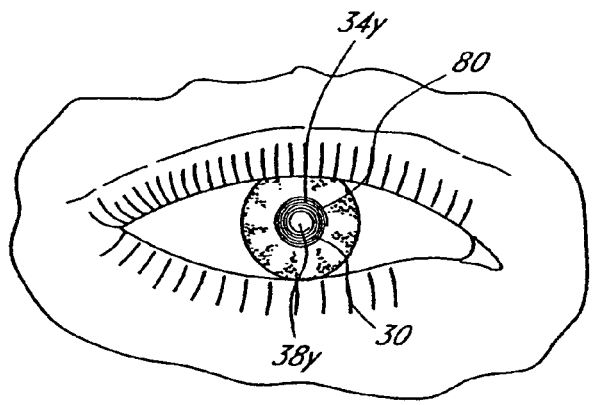
FIG. 41 is a plan view of an embodiment of a mask made of a spiraled fibrous strand.
Figure 42:
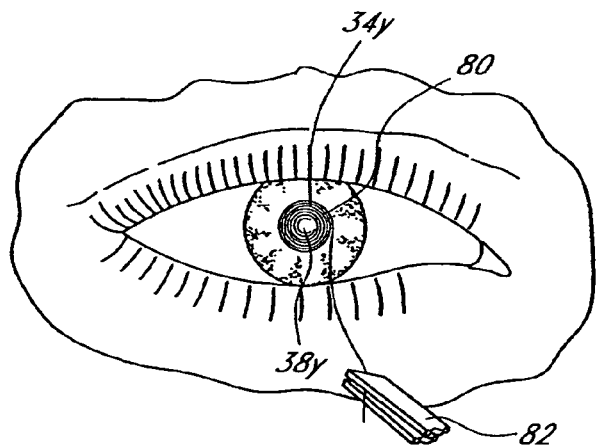
FIG. 42 is a plan view of the mask of FIG. 41 being removed from the eye.

FIGS. 41 and 42 illustrate another embodiment, of a mask 34y that includes a coiled strand 80 of a fibrous or other material. Strand 80 is coiled over itself to form the mask 34y, which may therefore be described as a spiral-like mask. This arrangement provides a pinhole or aperture 38y substantially in the center of the mask 34y. The mask 34y can be removed by a technician or surgeon who grasps the strand 80 with tweezers 82 through an opening made in a flap of the corneal 12. FIG. 42 shows this removal technique.

Further mask details are disclosed in U.S. Pat. No. 4,976,732, issued Dec. 11, 1990 and in U.S. Provisional Application Ser. No. 60/473,824, filed May 28, 2003, both of which are incorporated by reference herein in their entirety.

III. Methods of Applying Pinhole Aperture Devices

The various masks discussed herein can be used to improve the vision of a presbyopic patient as well as patient's with other vision problems. The masks discussed herein can be deployed in combination with a LASIK procedure, to eliminate the effects of abrasions, aberrations, and divots in the cornea. It is also believed that the masks disclosed herein can be used to treat patients suffering from macular degeneration, e.g., by directing light rays to unaffected portions of retina, thereby improving the vision of the patient. Whatever treatment is contemplated, more precise the alignment of the central region of a mask with a pin-hole aperture with the visual axis of the patient is believed to provide greater clinical effect to the patient.

A. Alignment of the Pinhole Aperture with the Patient's Visual Axis

Alignment of the central region of the pinhole aperture 38, in particular, the optical axis 39, of the mask 34 with the visual axis of the eye 10 may be achieved in a variety of ways. As discussed more fully below, such alignment may be achieved by imaging two reference targets at different distances and effecting movement of the patient's eye to a position where the images of the first and second reference targets appear aligned as viewed by the patient's eye. When the patient views the targets as being aligned, the patient's visual axis is located.

Figure 43:
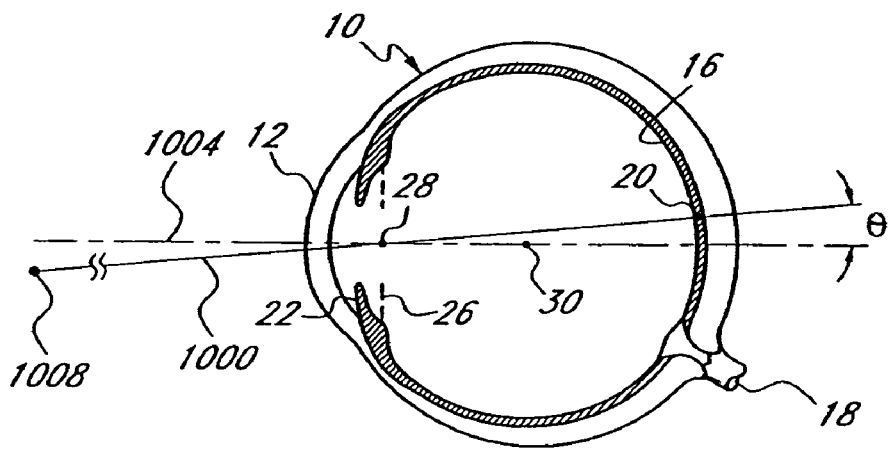
FIG. 43 is a cross-sectional view similar to that of FIG. 1, but showing certain axes of the eye.

FIG. 43 is a cross-sectional view of the eye 10, similar to that shown in FIG. 1, indicating a first axis 1000 and a second axis 1004. The first axis 1000 represents the visual axis, or line of sight, of the patient and the second axis 1004 indicates the axis of symmetry of the eye 10. The visual axis 1000 is an axis that connects the fovea 20 and a target 1008. The visual axis 1000 also extends through the central point 28 of the entrance pupil 26. The target 1008 is sometimes referred to herein as a "fixation point." The visual axis 1000 also corresponds to the chief ray of the bundle of rays emanating from the target 1008 that passes through the pupil 22 and reaches the fovea 20. The axis of symmetry 1004 is an axis passing through the central point 28 of the entrance pupil 26 and the center of rotation 30 of the eye 10. As described above, the cornea 12 is located at the front of the eye 10 and, along with the iris 22, admits light into the eye 10. Light entering the eye 10 is focused by the combined imaging properties of the cornea 12 and the intraocular lens 14 (see FIGS. 2-3).

In a normal eye, the image of the target 1008 is formed at the retina 16. The fovea 20 (the region of the retina 16 with particularly high resolution) is slightly off-set from the axis of symmetry 1004 of the eye 10. This visual axis 1000 is typically inclined at an angle θ of about six (6) degrees to the axis of symmetry 1004 of the eye 10 for an eye with a centered iris.

Figure 44A:
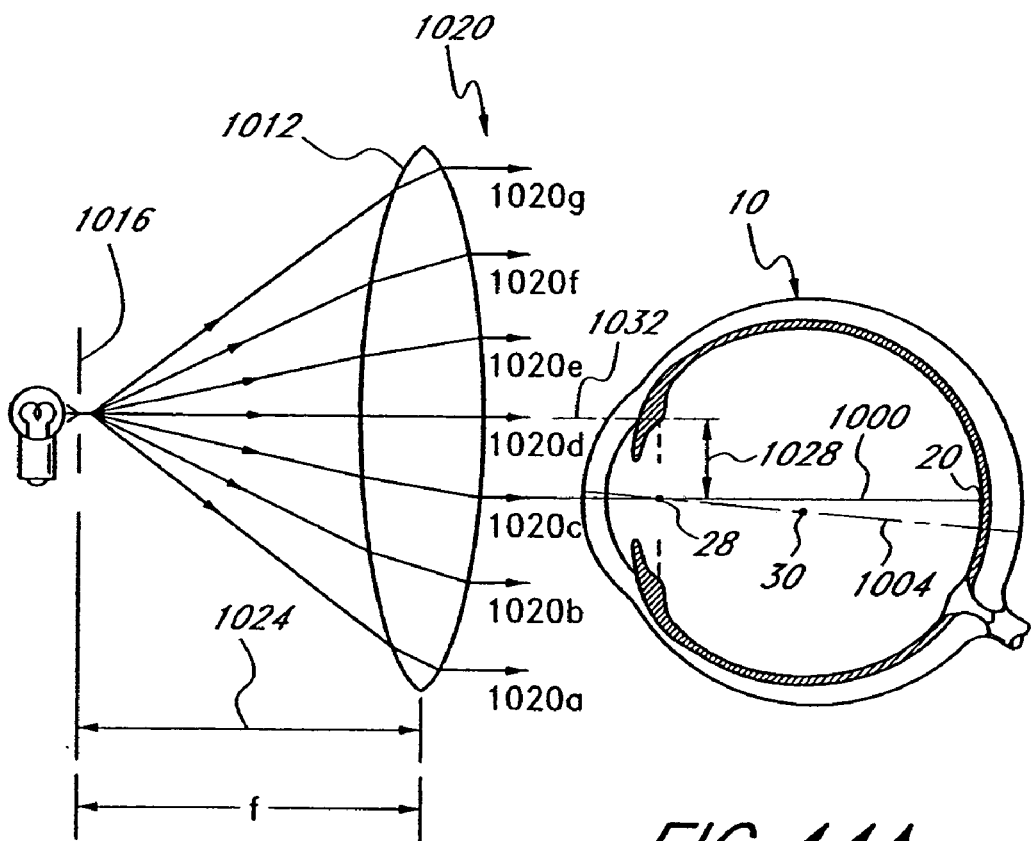
FIG. 44A illustrates a single-target fixation method for aligning an eye with the optical axis of an ophthalmic instrument.
Figure 44B:
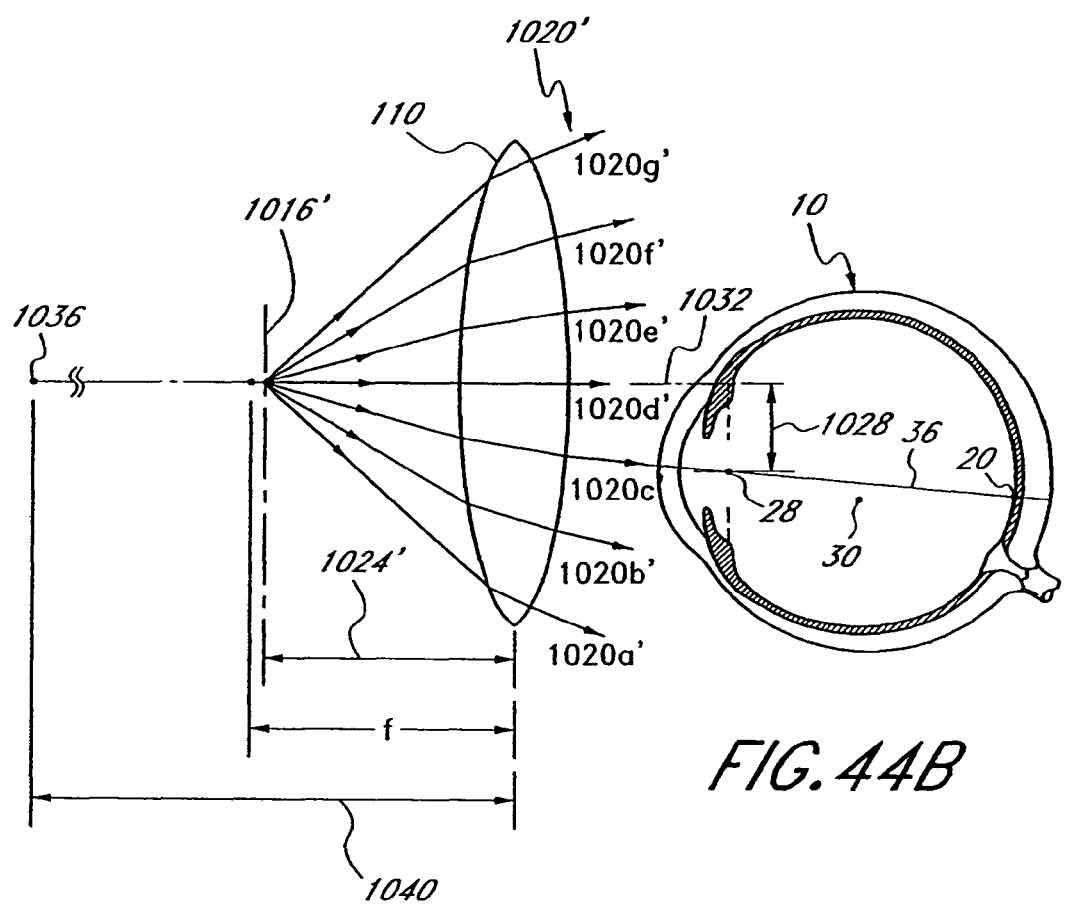
FIG. 44B illustrates another single-target fixation method for aligning an eye with the optical axis of an ophthalmic instrument.

FIGS. 44A and 44B illustrate single-target fixation methods for aligning an eye with an optical axis of an instrument also referred to herein as an "instrument axis." In FIG. 44A, the eye 10 is shown looking into an aperture of a projection lens 1012. The lens aperture is shown as the entire lens 1012. The projection lens 1012 reimages a reference target 1016 at an infinite distance, producing a collimated beam 1020.

The reference target 1016 in FIG. 44A is shown reimaged at an infinite distance, which is achieved by positioning the target object at a distance 1024 equal to the focal length f of the lens 1012, i.e. the reference target 1016 is at the lens focal point. To first-order approximation, the relationship between the object and the image distances for a lens of focal length f follows the Gaussian equation $(1/A)=(1/f)+(1/B)$ where B and A are respectively the object and image distances measured from the lens center. Because the illuminated target appears at an infinite distance as viewed by the eye 10, individual light rays $1020a$ to $1020g$ are parallel to each other.

FIG. 44A shows the eye 10 fixated on the reference target 1016 along a ray $1020c$, which appears to come from the reference target 1016 as imaged by the projection lens 1012. The eye 10 is here decentered a distance 1028 from an optical axis 1032 of the instrument, i.e., the instrument axis, which may be the central axis of the lens 1012. This decentration of the eye 10 with respect to the optical axis 1032 of the instrument does not affect fixation to an infinitely distant image because all rays projected by the lens 1012 are parallel. As such, in an instrument that relies on fixation to a single target imaged at infinity, an eye can be fixated on the target but still be off-center of the optical axis of the instrument.

FIG. 44B is similar to FIG. 44A, except that a reference target 1016' is located somewhat closer to the projection lens 1012 that is the reference target 1016 so that an image 1036 of the reference target 1016' appears at a large but finite distance 1040 behind the lens 1012. As was the case in FIG. 44A, the eye 10 in FIG. 44B is fixated on the reference target 1016' along a ray $1020c'$, which is decentered a distance 1028 from an optical axis 1032 of the instrument. However, the rays $1020a'$ to $1020g'$ projected by the lens 1012 shown in FIG. 44B are seen to diverge as if they originated at the image 1036 of the reference target 1016', which is located on the optical axis 1032 of the lens 1012 at a finite distance 1040 from the lens 1012. If the decentration of the eye 10 (corresponding to the distance 1028) changes, the eye 10 must rotate somewhat about its center of rotation 30 in order to fixate on the image 1036. The eye 10 in FIG. 44B is shown rotated by some angle so as to align its visual axis 1000 with the direction of propagation of ray $1020c'$. Thus, in general, a decentered eye fixated on a finite-distance target is not merely off-center but is also angularly offset from the optical axis 1032 of the instrument.

Figure 45A:
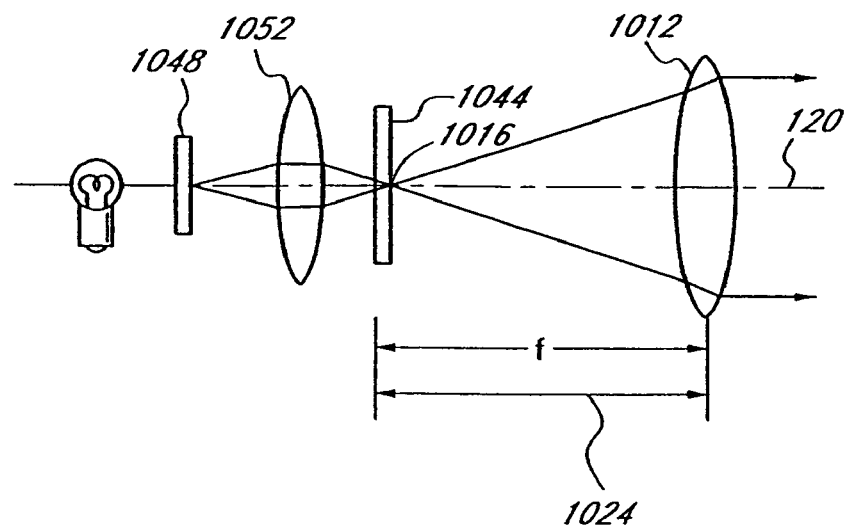
FIG. 45A shows an apparatus for projecting a target onto an optical axis at an infinite distance.

FIG. 45A shows one embodiment of a projection lens 1012 used to create an optical image at infinite distance, as was schematically shown in FIG. 44A. The reference target 1016 typically is a back-illuminated pattern on a transparent glass reticle 1044. The reference target 1016 is located at a distance 1024 on the lens' optical axis 1032 at the lens' focal point, i.e. the reference target 1016 is located such that the distance 1024 is equal to the distance f A diffusing plate 1048 and a condensing lens 1052 are used to ensure full illumination of the reference target 1016 throughout the aperture of the projection lens 1012. Light rays projected by the projection lens 1012 are substantially parallel depending upon the degree of imaging perfection achieved in the optical system. Assuming a well-corrected lens with small aberrations, the image as observed through the aperture of the projection lens 1012 will appear to be at infinity.

Figure 45B:
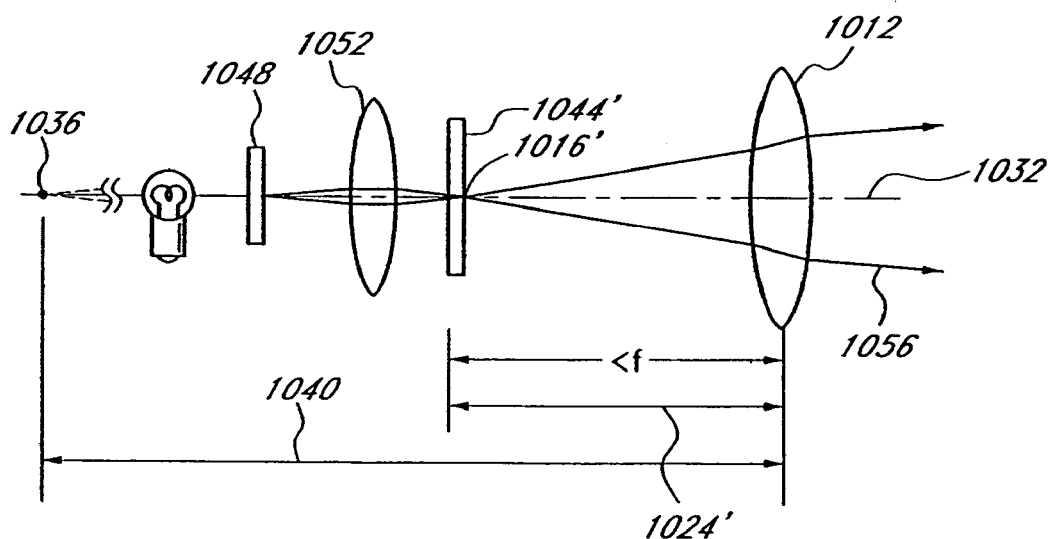
FIG. 45B shows an apparatus for projecting a target onto an optical axis at a finite distance.

FIG. 45B shows a somewhat different optical system in which a target 1016' is projected so that an image 1036 appears at a large but finite distance 1040 behind the lens 1012, as was shown schematically in FIG. 44B. The diffusing plate 1048 and the condensing lens 1052 again are used to ensure that full illumination of the target reference 112' is achieved throughout the aperture of the projection lens 1012. In the system of FIG. 45B the reference target 1016' is located at an object distance 1024', which is inside the focal point in accordance with the aforementioned Gaussian equation. Thus, the object distance 1024' is a distance that is less than the focal length f of the lens 1012'. The path of a typical light ray 1056 from the center of the reference target 1016' is shown. If the eye 10 is aligned with this ray 1056, the reference target 1016 is observed as if it were located at the location of the image 1036, i.e. at a finite distance. The ray 1056 would then be similar to ray $1020c'$ of FIG. 44B, and fixation of the eye 10 could be established as appropriate for the given degree of decentration from the optical axis 1032.

Figure 46:
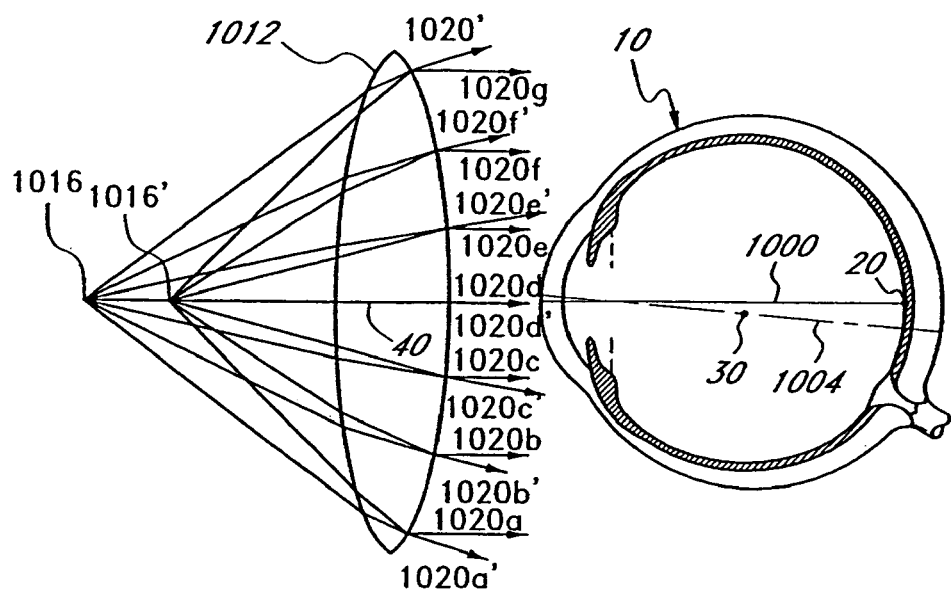
FIG. 46 illustrates a dual-target fixation method.

FIG. 46 illustrates a fixation method whereby the single-target fixation methods shown in FIGS. 44A and 44B are both used simultaneously in a dual-target fixation system. With two fixation targets 1016 and 1016' at different distances, the eye 10 will see angular disparity (parallax) between the target images (i.e., they will not appear to be superimposed) if the eye is decentered. The rays $1020a$ to $1020g$ of the infinite-distance target 1016 are parallel to one another, while the rays $1020a'$ to $1020g'$ of the finite distance target 1016' diverge. The only rays of the targets that coincide are rays $1020d$ and $10204d'$, which are collinear along the optical axis 1032 of the instrument. Thus, the eye 10 can be simultaneously fixated on both targets if the visual axis, represented by the first axis 1000 of the eye 10, is centered on the optical axis of the instrument, i.e. along the ray $1020d$ (which is the same as $1020d'$). Thus, when the visual axis of the eye 10 lies on the optical axis 1032 of the apparatus, both images are fixated.

Figure 47:
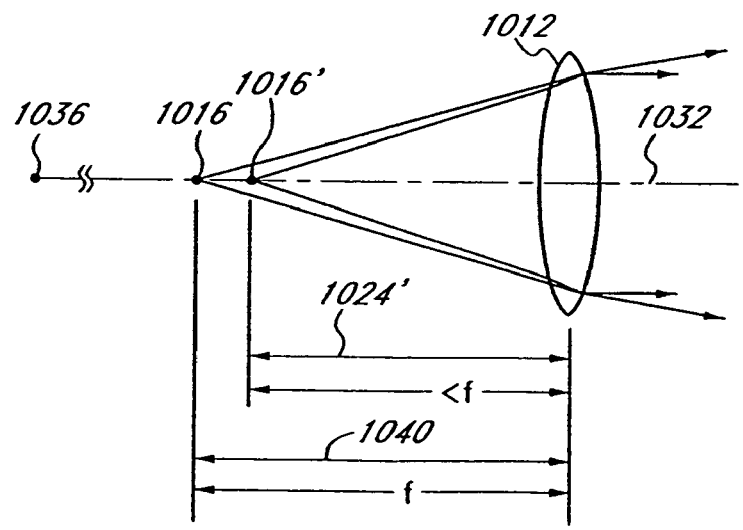
FIG. 47 shows an apparatus with which two targets can be projected simultaneously by the same projection lens to provide fixation targets at a large distance (such as infinity) and a shorter (finite) distance.

FIG. 47 shows schematically an apparatus with which two reticle patterns could be projected simultaneously by the same projection lens to provide fixation targets 1016 and 1016' at a large distance 1024 (such as infinity) and a shorter (finite) distance 1024'. It is preferable that both fixation targets are at relatively large distances so that only slight focus accommodation of the eye 10 is required to compensate for these different distances. By instructing the patient to move his or her eye transversely with respect to the instrument axis until a visual event occurs, e.g., angular displacement (parallax) between the images is minimized, alignment of the eye 10 with the optical axis 1032 of the apparatus is facilitated. Providing two fixation targets at different apparent distances will simplify accurate alignment of the sighted eye with an ophthalmic apparatus in the surgical procedures disclosed herein and in other similar surgical procedures.

Figure 48:
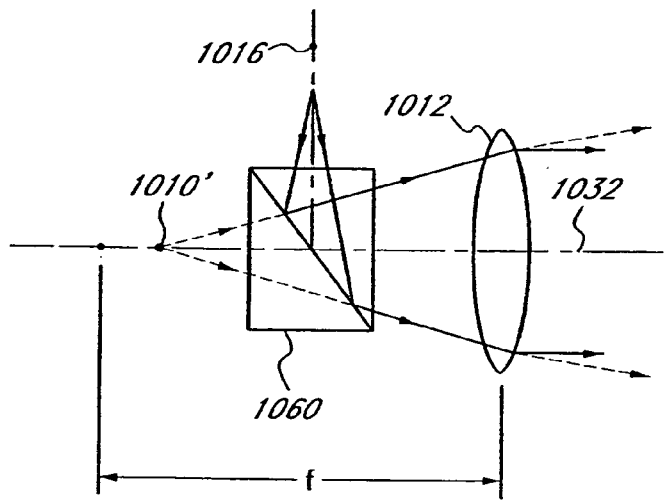
FIG. 48 shows another embodiment of an apparatus for combining two targets to project them simultaneously at different axial distances.

FIG. 48 shows another embodiment of an apparatus for combining two fixation targets 1016 and 1016' to project them simultaneously at different axial distances. A beamsplitter plate or cube 1060 is inserted between the patterns and the projection lens 1012 so each pattern can be illuminated independently. In the embodiments of FIGS. 46 and 47, the targets 1016, 1016' can be opaque lines seen against a light background, bright lines seen against a dark background, or a combination of these forms.

Figure 49A:
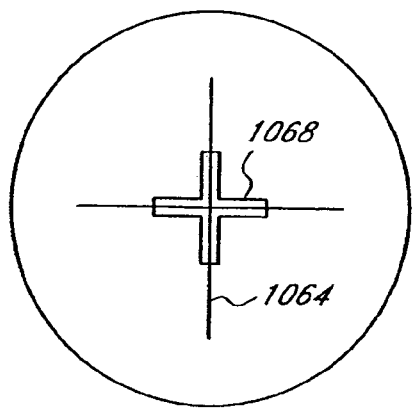
FIG. 49A shows an example of a dual target pattern as viewed by the patient when the target patterns are aligned.
Figure 49B:
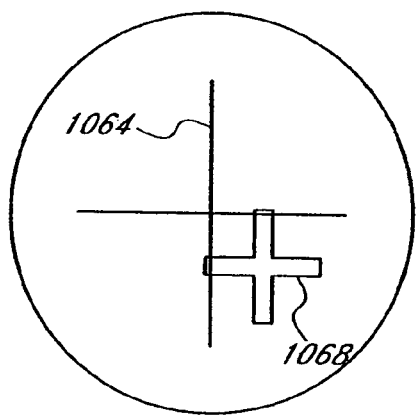
FIG. 49B shows the dual target pattern of FIG. 49A when the patterns are offset.

FIG. 49A shows an example of a typical dual pattern as viewed by the patient when the patterns are aligned, i.e. when the patient's eye is aligned with the optical axis of the apparatus. The dual pattern set in this embodiment comprises an opaque fine-line cross 1064 seen against a broader bright cross 1068. FIG. 49B shows the same dual pattern set as shown in FIG. 49A, except the patterns are offset, indicating that the eye 10 is decentered with respect to the optical axis of the associated optical instrument.

Figure 50A:
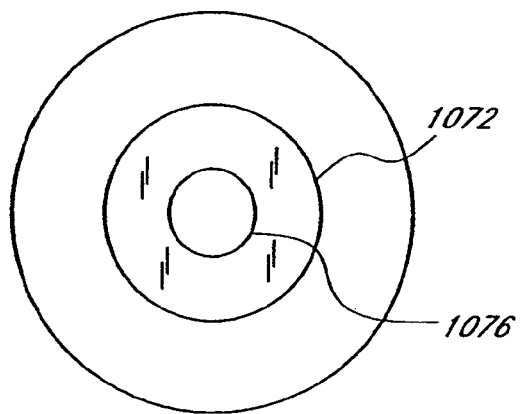
FIG. 50A shows an example of another dual target pattern as viewed by the patient when the target patterns are aligned.
Figure 50B:
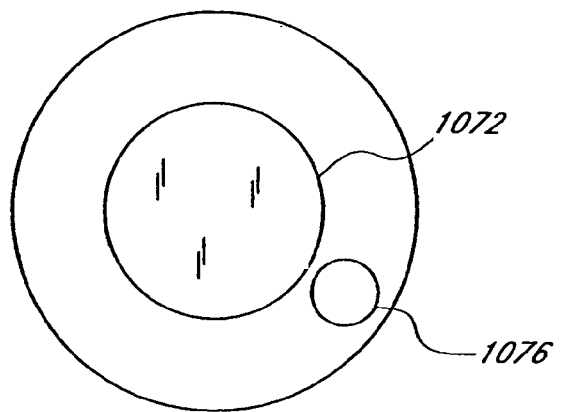
FIG. 50B shows the dual target pattern of FIG. 50A when the target patterns are offset.

FIG. 50A shows an example of another dual pattern as viewed by the patient when the patterns are aligned, i.e. when the patient's eye is aligned with the optical axis of the ophthalmic instrument. The dual pattern set in this embodiment comprises an opaque circle 1072 seen against a bright circle 1076. The circle 1072 has a diameter that is greater than the diameter of the circle 1076. FIG. 50B shows the same dual pattern set as shown in FIG. 50A, except the patterns are offset, indicating that the eye 10 is decentered with respect the optical axis of the associated optical instrument. It is not necessary that the targets appear as crosses or circles; patterns such as dots, squares, and other shapes and patterns also can suffice.

In another embodiment, color is used to indicate when the patient's eye is aligned with the optical axis of the apparatus. For example, a dual color set can be provided. The dual color set may comprise a first region of a first color and a second region of a second color. As discussed above in connection with the dual pattern sets, the patient visual axis is located when the first color and the second color are in a particular position relative to each other. This may cause a desired visual effect to the patient's eye, e.g., when the first region of the first color is aligned with the second region of the second color, the patient may observe a region of a third color. For example, if the first region is colored blue and the second region is colored yellow, the patient will see a region of green. Additional details concerning locating a patient's visual axis or line of sight are contained in U.S. Pat. No. 5,474,548, issued Dec. 12, 1995, incorporated by reference herein in its entirety.

Figure 51:
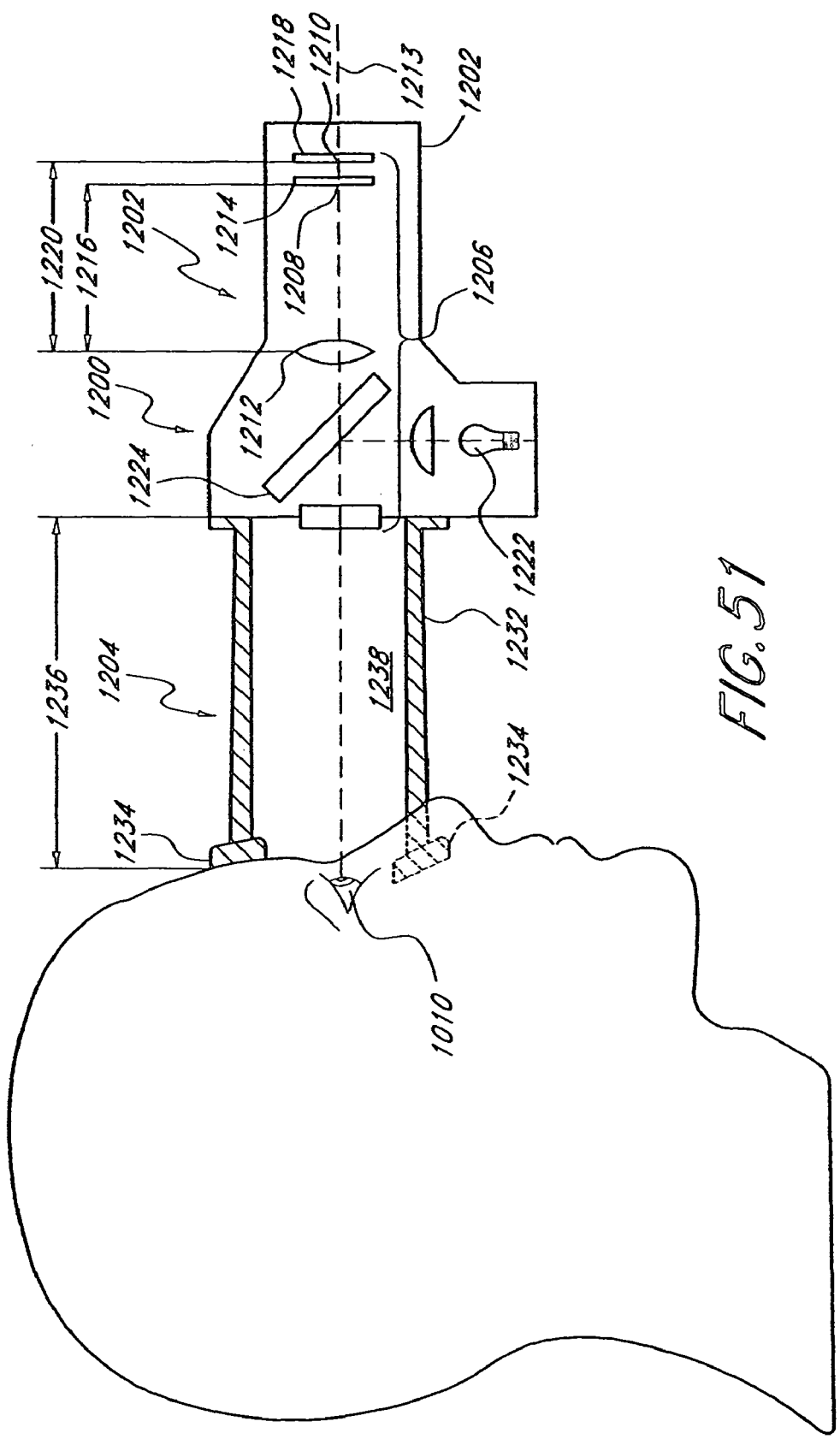
FIG. 51 shows one embodiment of an apparatus configured to locate the visual axis of an eye of a patient by aligning the axis with an axis of the apparatus.

FIG. 51 shows one embodiment of an ophthalmic instrument 1200 that can be used in connection with various methods described herein to locate the visual axis of a patient. The instrument 1200 includes an optics housing 1202 and a patient locating fixture 1204 that is coupled with the optics housing 1202. The optics housing 1202 includes an optical system 1206 that is configured to project two reticle patterns simultaneously to provide fixation targets at a large distance, e.g., infinity, and a shorter, finite distance.

In the illustrated embodiment, the optical system 1206 of the instrument includes a first reference target 1208, a second reference target 1210, and a projection lens 1212. The first and second reference targets 1208, 1210 are imaged by the projection lens 1212 along an instrument axis 1213 of the ophthalmic instrument 1200. In one embodiment, the first reference target 1208 is formed on a first glass reticle 1214 located a first distance 1216 from the lens 1212 and the second target 1210 is formed on a second glass reticle 1218 located a second distance 1220 from the lens 1212. Preferably, the second distance 1220 is equal to the focal length f of the lens 1212, as was discussed in connection with FIG. 44A. As discussed above, positioning the second target 1210 at the focal length f of the lens 1212 causes the second target 1210 to be imaged at an infinite distance from the lens 1212. The first distance 1216 preferably is less than the second distance 1220. As discussed above, the first reference target 1208 is thereby imaged at a large but finite distance from the lens 1212. By positioning the first and second reference targets 1208, 1210 in this manner, the method set forth above for aligning the eye 10 of the patient may be implemented with the ophthalmic instrument 1200.

The optical system 1206 preferably also includes a light source 1222 that marks the visual axis of the patient after the visual axis has been located in the manner described above. In the illustrated embodiment, the light source 1222 is positioned separately from the first and second reference targets 1208, 1210. In one embodiment, the light source 1222 is positioned at a ninety degree angle to the instrument axis 1213 and is configured to direct light toward the axis 1213. In the illustrated embodiment, a beamsplitter plate or cube 1224 is provided between the first and second reference targets 1208, 1210 and the patient to route light rays emitted by the light source 1222 to the eye of the patient. The beamsplitter 1224 is an optical component that reflects light rays from the direction of the light source 1222, but permits the light rays to pass through the beamsplitter along the instrument axis 1213. Thus, light rays form the first and second reference targets 1208, 1210 and from the light source 1222 may be propagated toward the eye of the patient. Other embodiments are also possible. For example, the beamsplitter 1224 could be replaced with a mirror that is movable into and out of the instrument axis 1213 to alternately reflect light from the light source 1222 to the eye or to permit light from the first and second reference targets 1208, 1210 to reach the eye.

The patient locating fixture 1204 includes an elongate spacer 1232 and a contoured locating pad 1234. The contoured locating pad 1234 defines an aperture through which the patient may look along the instrument axis 213. The spacer 1232 is coupled with the optics housing 1202 and extends a distance 1236 between the housing 1202 and the contoured locating pad 1234. In one embodiment, the spacer 1232 defines a lumen 1238 that extends between the contoured locating pads 1234 and the optics housing 1202. In some embodiments, the magnitude of the distance 1236 may be selected to increase the certainty of the location of the patient's visual axis. In some embodiments, it is sufficient that the distance 1236 be a relatively fixed distance.

When the alignment apparatus 1200 is used, the patient's head is brought into contact with the contoured locating pad 1234, which locates the patients eye 10 in the aperture at a fixed distance from the first and second reference targets 1208, 1210. Once the patient's head is positioned in the contoured locating pad 1234, the patient may move the eye 10 as discussed above, to locate the visual axis. After locating the visual axis, the light source 1222 is engaged to emit light toward the eye 10, e.g., as reflected by the beamsplitter 1224.

In the illustrated embodiment, at least some of the light emitted by the light source 1222 is reflected by the beamsplitter 1224 along the instrument axis 1213 toward the patient's eye 10. Because the visual axis of the eye 10 was previously aligned with the instrument axis 1213, the light from the light source 1222 reflected by the beamsplitter 1224 is also aligned with the visual axis of the eye 10.

The reflected light provides a visual marker of the location of the patient's visual axis. The marking function of the light source 1222 is particularly useful in connection with the methods, described below, of applying a mask. Additional embodiments of ophthalmic instruments embodying this technique are described below in connection with FIGS. 55-59.

B. Methods of Applying a Mask

Having described a method for properly locating the visual axis of the eye 10 a patient and for visually marking the visual axis, various methods for applying a mask to the eye will be discussed.

Figure 52:
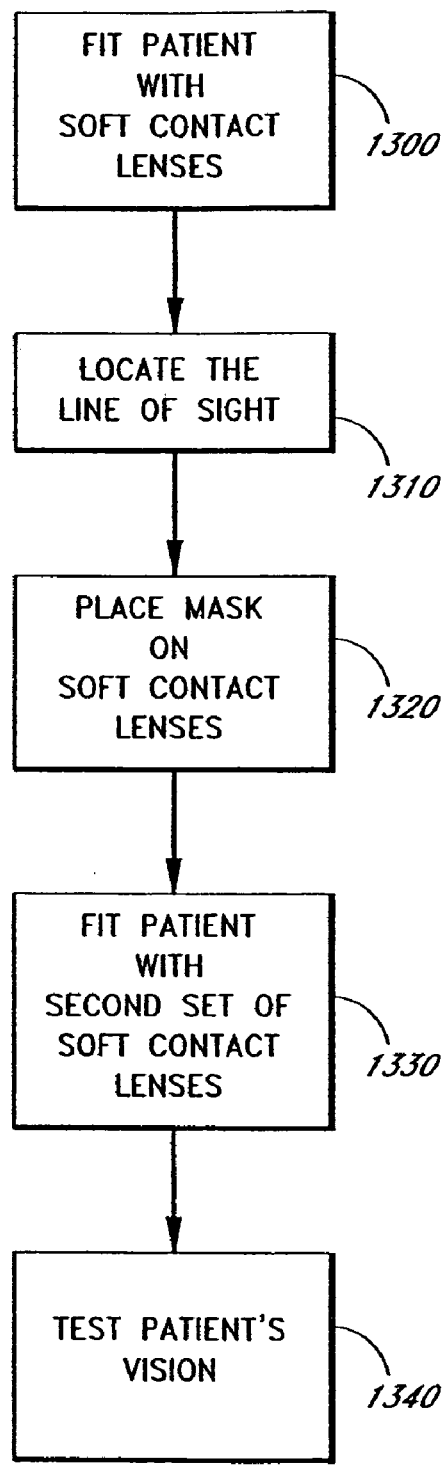
FIG. 52 is a flow chart illustrating one method of screening a patient for the use of a mask.

FIG. 52 shows an exemplary process for screening a patient interested in increasing his or her depth of focus. The process begins at step 1300, in which the patient is fitted with soft contact lenses, i.e., a soft contact lens in placed in each of the patient's eyes. If needed, the soft contact lenses may include vision correction. Next, at step 1310, the visual axis of each of the patient's eyes is located as described above. At a step 1320, a mask, such as any of those described above, is placed on the soft contact lenses such that the optical axis of the aperture of the mask is aligned with the visual axis of the eye.

In this position, the mask will be located generally concentric with the patient's pupil. In addition, the curvature of the mask should parallel the curvature of the patient's cornea. The process continues at a step 1330, in which the patient is fitted with a second set of soft contact lenses, i.e., a second soft contact lens is placed over the mask in each of the patient's eyes. The second contact lens holds the mask in a substantially constant position. Last, at step 1340, the patient's vision is tested. During testing, it is advisable to check the positioning of the mask to ensure that the optical axis of the aperture of the mask is substantially collinear with the visual axis of the eye. Further details of testing are set forth in U.S. Pat. No. 6,554,424, issued Apr. 29, 2003, incorporated by reference herein in its entirety.

In accordance with a still further embodiment of the invention, a mask is surgically implanted into the eye of a patient interested in increasing his or her depth of focus. For example, a patient may suffer from presbyopia, as discussed above. The mask may be a mask as described herein, similar to those described in the prior art, or a mask combining one or more of these properties. Further, the mask may be configured to correct visual aberrations. To aid the surgeon surgically implanting a mask into a patient's eye, the mask may be pre-rolled or folded for ease of implantation.

The mask may be implanted in several locations. For example, the mask may be implanted underneath the cornea's epithelium sheet, beneath the cornea's Bowman membrane, in the top layer of the cornea's stroma, or in the cornea's stroma. When the mask is placed underneath the cornea's epithelium sheet, removal of the mask requires little more than removal of the cornea's epithelium sheet.

Figure 53A:
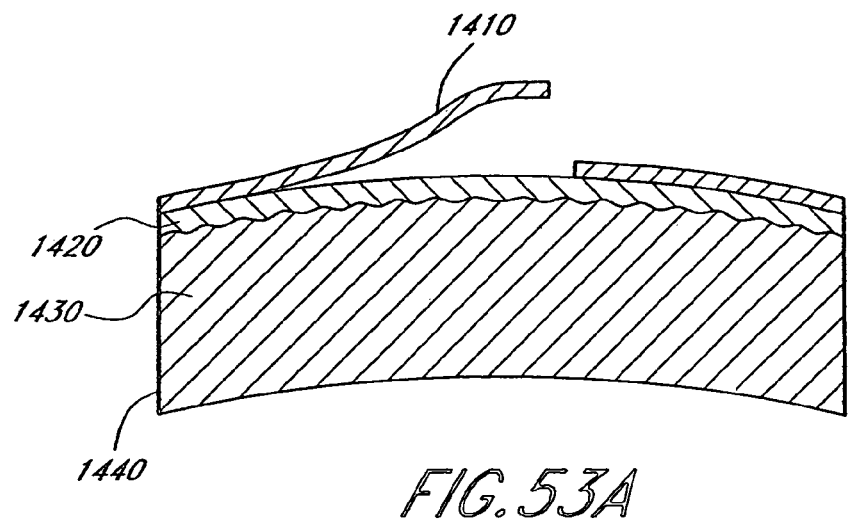
FIG. 53A-53C show a mask, similar to those described herein, inserted beneath an epithelium sheet of a cornea.
Figure 53B:
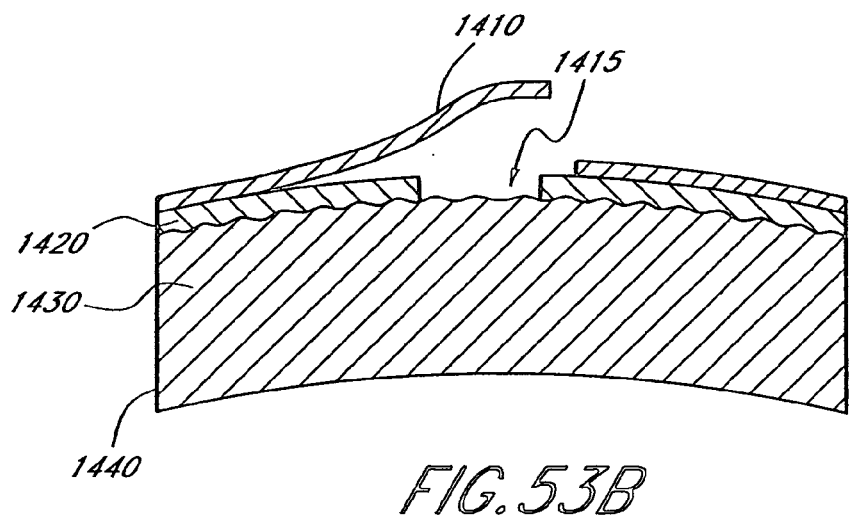
Figure 53C:
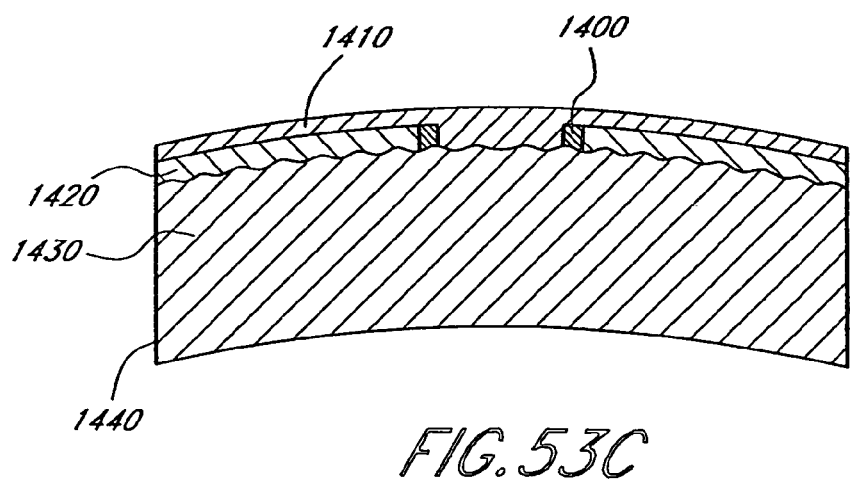

FIGS. 53a through 53c show a mask 1400 inserted underneath an epithelium sheet 1410. In this embodiment, the surgeon first removes the epithelium sheet 1410. For example, as shown in FIG. 53a, the epithelium sheet 1410 may be rolled back. Then, as shown in FIG. 53b, the surgeon creates a depression 1415 in a Bowman's membrane 420 corresponding to the visual axis of the eye. The visual axis of the eye may be located as described above and may be marked by use of the alignment apparatus 1200 or other similar apparatus. The depression 1415 should be of sufficient depth and width to both expose the top layer 1430 of the stroma 1440 and to accommodate the mask 1400. The mask 1400 is then placed in the depression 1415. Because the depression 1415 is located in a position to correspond to the visual axis of the patient's eye, the central axis of the pinhole aperture of the mask 1400 will be substantially collinear with the visual axis of the eye. This will provide the greatest improvement in vision possible with the mask 1400. Last, the epithelium sheet 1410 is placed over the mask 1400. Over time, as shown in FIG. 53c, the epithelium sheet 1410 will grow and adhere to the top layer 1430 of the stroma 1440, as well as the mask 1400 depending, of course, on the composition of the mask 1400. As needed, a contact lens may be placed over the incised cornea to protect the mask.

Figure 54A:
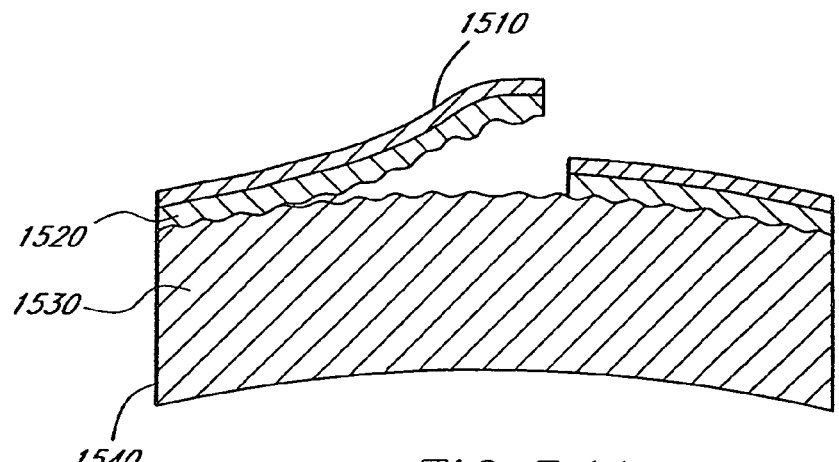
FIG. 54A-54C show a mask, similar to those described herein, inserted beneath an Bowman's membrane of a cornea.
Figure 54B:
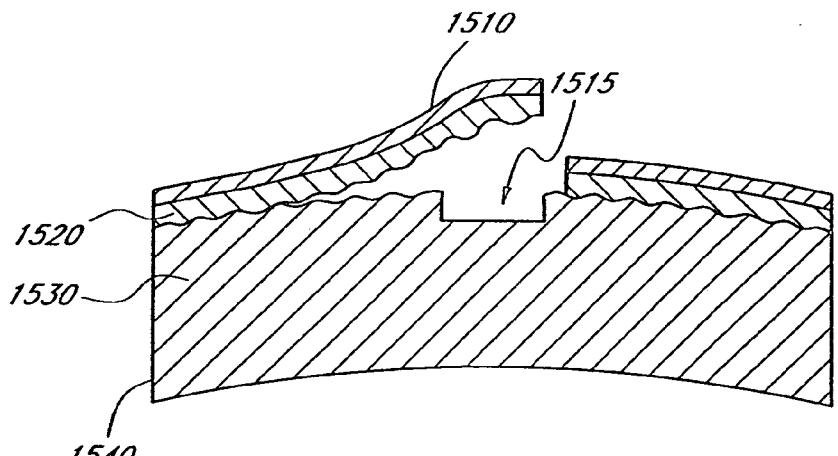
Figure 54C:
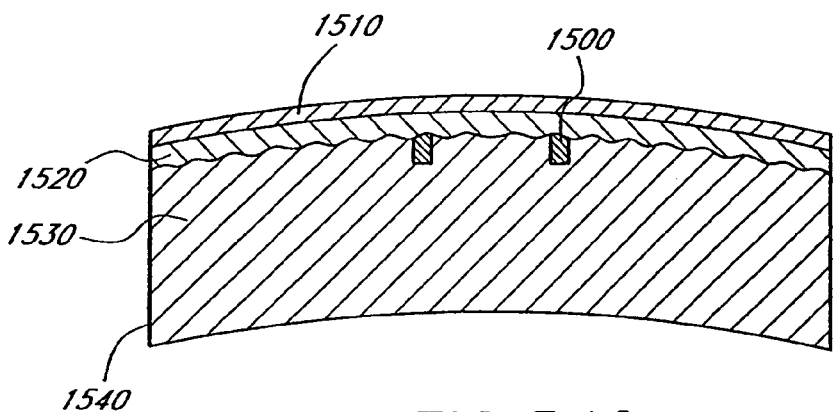

FIGS. 54a through 54c show a mask 1500 inserted beneath a Bowman's membrane 1520 of an eye. In this embodiment, as shown in FIG. 54a, the surgeon first hinges open the Bowman's membrane 1520. Then, as shown in FIG. 54b, the surgeon creates a depression 1515 in a top layer 1530 of a stroma 1540 corresponding to the visual axis of the eye. The visual axis of the eye may be located as described above and may be marked by using the alignment apparatus 1200 or other similar apparatus. The depression 1515 should be of sufficient depth and width to accommodate the mask 1500. Then, the mask 1500 is placed in the depression 1515. Because the depression 1515 is located in a position to correspond to the visual axis of the patient's eye, the central axis of the pinhole aperture of the mask 1500 will be substantially collinear with the visual axis of the eye. This will provide the greatest improvement in vision possible with the mask 1500. Last, the Bowman's membrane 1520 is placed over the mask 1500. Over time, as shown in FIG. 54c, the epithelium sheet 1510 will grow over the incised area of the Bowman's membrane 1520. As needed, a contact lens may be placed over the incised cornea to protect the mask.

In another embodiment, a mask of sufficient thinness, i.e., less than substantially 20 microns, may be placed underneath epithelium sheet 1410. In another embodiment, an optic mark having a thickness less than about 20 microns may be placed beneath Bowman's membrane 1520 without creating a depression in the top layer of the stroma.

In an alternate method for surgically implanting a mask in the eye of a patient, the mask may be threaded into a channel created in the top layer of the stroma. In this method, a curved channeling tool creates a channel in the top layer of the stroma, the channel being in a plane parallel to the surface of the cornea. The channel is formed in a position corresponding to the visual axis of the eye. The channeling tool either pierces the surface of the cornea or, in the alternative, is inserted via a small superficial radial incision. In the alternative, a laser focusing an ablative beam may create the channel in the top layer of the stroma. In this embodiment, the mask may be a single segment with a break, or it may be two or more segments. In any event, the mask in this embodiment is positioned in the channel and is thereby located so that the central axis of the pinhole aperture formed by the mask is substantially collinear with the patient's visual axis to provide the greatest improvement in the patient's depth of focus.

In another alternate method for surgically implanting a mask in the eye of a patient, the mask may be injected into the top layer of the stroma. In this embodiment, an injection tool with a stop penetrates the surface of the cornea to the specified depth. For example, the injection tool may be a ring of needles capable of producing a mask with a single injection. In the alternative, a channel may first be created in the top layer of the stroma in a position corresponding to the visual axis of the patient. Then, the injector tool may inject the mask into the channel. In this embodiment, the mask may be a pigment, or it may be pieces of pigmented material suspended in a biocompatible medium. The pigment material may be made of a polymer or, in the alternative, made of a suture material. In any event, the mask injected into the channel is thereby positioned so that the central axis of the pinhole aperture formed by the pigment material is substantially collinear with the visual axis of the patient.

In another method for surgically implanting a mask in the eye of a patient, the mask may be placed beneath the corneal flap created during keratectomy, when the outermost 20% of the cornea is hinged open. As with the implantation methods discussed above, a mask placed beneath the corneal flap created during keratectomy should be substantially aligned with the patient's visual axis, as discussed above, for greatest effect.

In another method for surgically implanting a mask in the eye of a patient, the mask may be aligned with the patient's visual axis and placed in a pocket created in the cornea's stroma.

Further details concerning alignment apparatuses are disclosed in U.S. Provisional Application Ser. No. 60/479,129, filed Jun. 17, 2003, incorporated by reference herein in its entirety.

Figure 55:
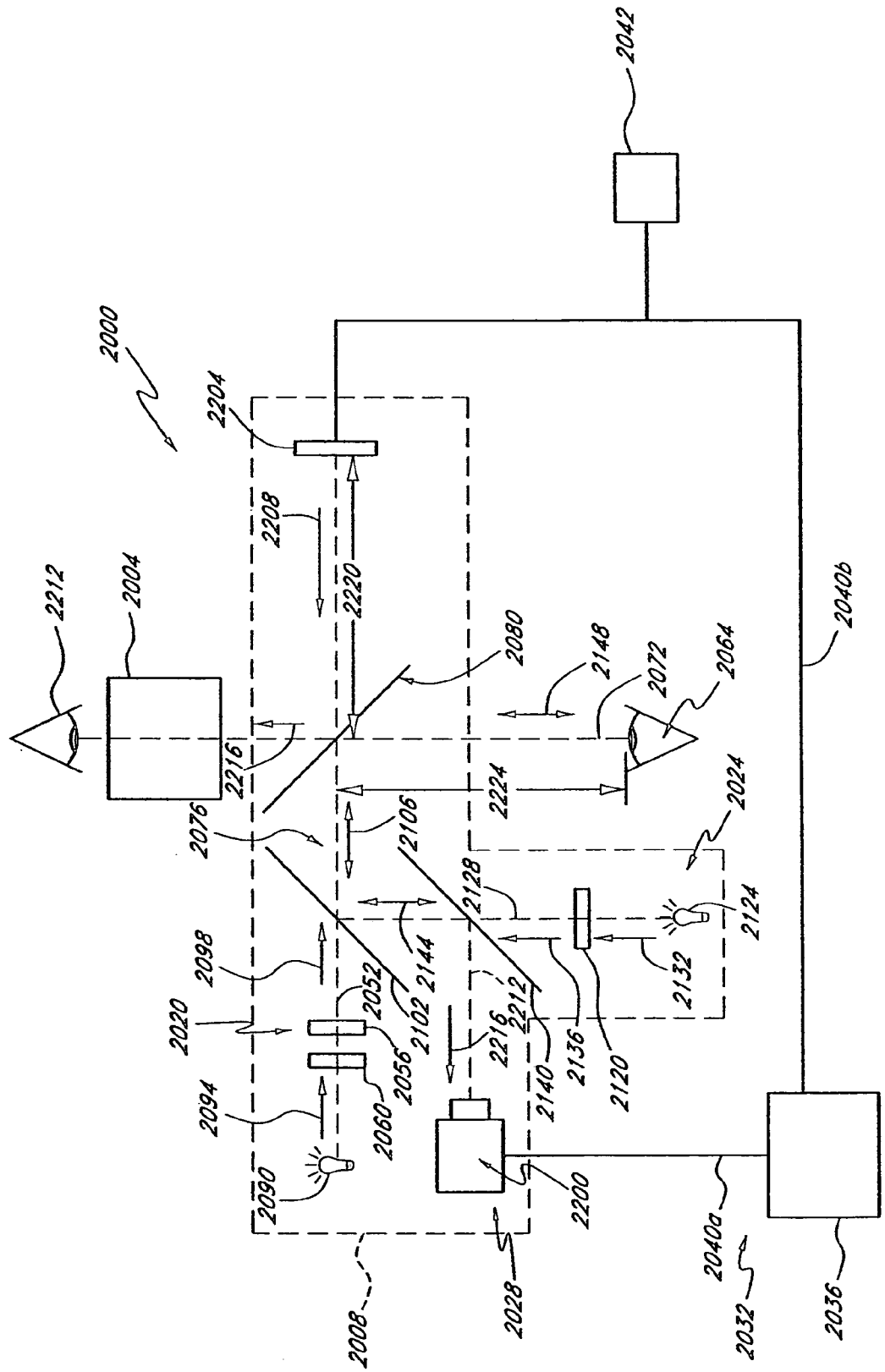
FIG. 55 is a schematic diagram of one embodiment of a surgical system configured located the visual axis of a patient's eye by aligning the visual axis with an axis of the system.

IV. Further Surgical Systems for Aligning a Pinhole Aperture with a Patient's Eye FIG. 55 shows a surgical system 2000 that employs dual target fixation in a manner similar to that discussed above in connection with FIGS. 43-51. The surgical system 2000 enables the identification of a unique feature of a patient's eye in connection with a surgical procedure. The surgical system 2000 is similar to the ophthalmic instrument 1200 except as set forth below. As discussed below, in one arrangement, the surgical system 2000 is configured to align an axis of the patient's eye, e.g., the patient's line of sight (sometimes referred to herein as the "visual axis"), with an axis of the system 2000. The axis of the system 2000 may be a viewing axis along which the patient may direct an eye. As discussed above, such alignment is particularly useful in many surgical procedures, including those that benefit from precise knowledge of the location of one or more structures or features of the eye on which the procedures is being performed.

In one embodiment, the surgical system 2000 includes a surgical viewing device 2004 and an alignment device 2008. In one embodiment, the surgical viewing device 2004 includes a surgical microscope. The surgical viewing device 2004 may be any device or combination of devices that enables a surgeon to visualize the surgical site with sufficient clarity or that enhances the surgeon's visualization of the surgical site. A surgeon also may elect to use the alignment device 2004 without a viewing device. As discussed more fully below in connection another embodiment of a surgical system shown in FIG. 56, the surgical system 2000 preferably also includes a fixture configured to conveniently mount one or more components to the surgical viewing device 2004.

In one embodiment, the alignment device 2008 includes an alignment module 2020, a marking module 2024, and an image capture module 2028. As discussed below, in another embodiment, the marking module 2024 is eliminated. Where the marking module 2024 is eliminated, one or more of its functions may be performed by the image capture module 2028. In another embodiment, the image capture module 2028 is eliminated. The alignment device 2004 preferably also has a control device 2032 that directs one or more components of the alignment device 2004. As discussed more fully below, the control device 2032 includes a computer 2036 and signal lines 2040a, 2040b, and a trigger 2042 in one embodiment.

The alignment module 2020 includes components that enable a patient to align a feature related to the patient's eye, vision, or sense of sight with an instrument axis, e.g., an axis of the alignment device 2008. In one embodiment, the alignment module 2020 includes a plurality of targets (e.g., two targets) that are located on the instrument axis. In the illustrated embodiment, the alignment module 2020 includes a first target 2056 and a second target 2060. The alignment module 2020 may be employed to align the patient's line-of-sight with an axis 2052 that extends perpendicular to the faces of the targets 2056, 2060.

Although the alignment device 2008 could be configured such that the patient is positioned relative thereto so that the eye is positioned along the axis 2052, it may be more convenient to position the patient such that an eye 2064 of the patient is not on the axis 2052. For example, as shown in FIG. 55, the patient may be positioned a distance 2068 from the axis 2052. FIG. 55 shows that the gaze of the patient's eye 2064 is directed generally along a patient viewing axis 2072.

In this arrangement, the alignment device 2008 is configured such that the patient viewing axis 2072 is at about a ninety degree angle with respect to the instrument axis 2052. In this embodiment, a path 2076 optically connecting the targets 2056, 2060 with the patient's eye 2064 extends partially along the axis 2052 and partially along the patient viewing axis 2072. The optical path 2076 defines the path along which the images of the targets 2056, 2060 are cast when the alignment device 2008 is configured such that the patient's eye 2064 is not on the axis 2052.

Positioning the patient off of the axis 2052, may be facilitated by one or more components that redirect light traveling along or parallel to the axis 2052. In one embodiment, the alignment device 2008 includes a beamsplitter 2080 located on the axis 2052 to direct along the patient viewing axis 2072 light rays coming toward the beamsplitter 2080 from the direction of the targets 2056, 2060. In this embodiment, at least a portion of the optical path 2076 is defined from the patient's eye 2064 to the beamsplitter 2080 and from the beamsplitter 2080 to the first and second targets 2056, 2060. Although the alignment device 2008 is configured to enable the patient viewing axis 2072 to be at about a ninety degree angle with respect to the axis 2052, other angles are possible and may be employed as desired. The arrangement of FIG. 55 is convenient because it enables a surgeon to be directly above and relatively close to the patient if the patient is positioned on his or her back on an operating table.

In one embodiment, the first target 2056 is on the axis 2052 and on the optical path 2076 between the second target 2060 and the patient's eye 2064. More particularly, light rays that are directed from the second target 2060 intersect the first target 2056 and are thereafter directed toward the beamsplitter 2080. As discussed more fully below, the first and second targets 2056, 2060 are configured to project a suitable pattern toward the patient's eye 2064. The patient interacts with the projected images of the first and second targets 2056, 2060 to align the line-of-sight (or other unique anatomical feature) of the patient's eye 2064 or of the patient's sense of vision with an axis of the instrument, such as the axis 2052, the viewing axis 2072, or the optical path 2076.

The first and second targets 2056, 2060 may take any suitable form. The targets 2056, 2060 may be similar to those hereinbefore described. The targets 2056, 2060 may be formed on separate reticles or as part of a single alignment target. In one embodiment, at least one of the first and second targets 2056, 2060 includes a glass reticle with a pattern formed thereon. The pattern on the first target 2056 and the pattern on the second target 2060 may be linear patterns that are combined to form a third linear pattern when the patient's line-of-sight is aligned with the axis 2052 or optical path 2076.

Figure 55A:
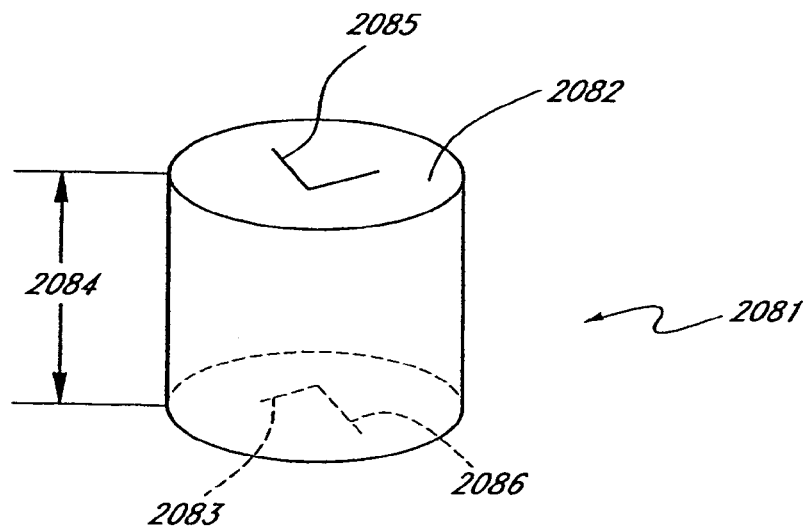
FIG. 55A is a perspective view of another embodiment of a dual target
Figure 55B:
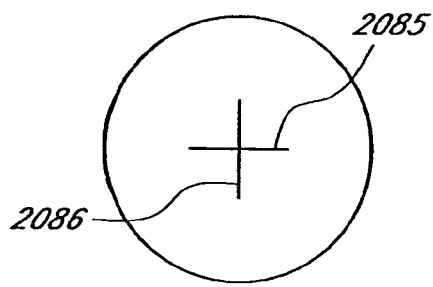
Figure 55C:
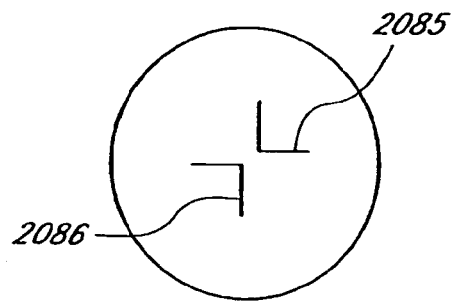

Although shown as separate elements, the first and second targets 2056, 2060 may be formed on a alignment target. FIGS. 55A-55C shows one embodiment of an alignment target 2081. The alignment target 2081 can be formed of glass or another substantially transparent medium. The alignment target 2081 includes a first surface 2082 and a second surface 2083. The first and second surfaces 2082, 2083 are separated by a distance 2084. The distance 2084 is selected to provide sufficient separation between the first and second surfaces 2082, 2083 to facilitate alignment by the patient by any of the methods described herein. In one embodiment, the alignment target 2081 includes a first pattern 2085 that may comprise a linear pattern formed on the first surface 2082 and a second pattern 2086 that may comprise a linear pattern formed on the second surface 2083. The first and second patterns 2085, 2086 are selected so that when the patient's line-of-sight is properly aligned with an axis of the alignment device 2008, the first and second patterns 2085, 2086 form a selected pattern (as in FIG. 55B) but when the patient's line-of-sight is properly aligned with an axis of the alignment device 2008, the first and second patterns 2085, 2086 do not form the selected pattern (as in FIG. 55C). In the illustrated embodiment, the first and second pattern 2085, 2086 each are generally L-shaped. When aligned, the first and second patterns 2085, 2086 form a cross. When not aligned, a gap is formed between the patterns and they appear as an L and an inverted L. This arrangement advantageously exploits vernier acuity, which is the ability of the eye to keenly detect misalignment of displaced lines. Any other combination of non-linear or linear patterns (e.g., other linear patterns that exploit vernier acuity) can be used as targets, as discussed above.

The first and second targets 2056, 2060 (or the first and second patterns 2085, 2086) may be made visible to the patient's eye 2064 in any suitable manner. For example, a target illuminator 2090 may be provided to make the targets 2056, 2060 visible to the eye 2064. In one embodiment, the target illuminator 2090 is a source of radiant energy, such as a light source. The light source can be any suitable light source, such as an incandescent light, a fluorescent light, one or more light emitting diodes, or any other source of light to illuminate the targets 2056, 2060.

As discussed more fully below, the alignment module 2020 also may include one or more optic elements, such as lenses, that relatively sharply focus the images projected from the first and second targets 2056, 2060 to present sharp images to the patient's eye 2064. In such arrangements, the focal length of the optic element or system of optical elements may be located at any suitable location, e.g., at the first or second targets 2056, 2060, between the first and second targets 2056, 2060 in front of the first target 2056, or behind the second target 2060. The focal length is the distance from a location (e.g., the location of an optic element) to the plane at which the optic element focuses the target images projected from the first and second target 2056, 2060.

FIG. 55 shows a series of arrows that indicate the projection of the images of the first and second targets 2056, 2060 to the patient's eye 2064. In particular, an arrow 2094 indicates the direction of light cast by the target illuminator 2090 along the axis 2052 toward the first and second targets 2056, 2060. The light strikes the first and second targets 2056, 2060 and is absorbed by or passed through the targets to cast an image of the targets 2056, 2060 along the axis 2052 in a direction indicated by an arrow 2098. In the embodiment of FIG. 55, the image of the first and second targets 2056, 2060 intersects a beamsplitter 2102 that forms a part of the marking module 2024 and the image capture module 2028. The beamsplitter 2102 is configured to transmit the majority of the light conveying the images of the first and second targets 2056, 2060 toward the beamsplitter 2080 as indicated by an arrow 2106. The beamsplitter 2102 will be discussed in greater detail below. The light is thereafter reflected by the beamsplitter 2080 along the patient viewing axis 2072 and toward the patient's eye 2064. As discussed more fully below, in some embodiments, the beamsplitter 2080 transmits some of the incident light beyond the beamsplitter 2080 along the axis 2050. In one embodiment, 70 percent of the light incident on the beamsplitter 2080 is reflected toward the patient's eye 2064 and 30 percent is transmitter. One skilled in the art will recognize that the beamsplitter 2080 can be configured to transmit and reflect in any suitable fraction.

While the target illuminator 2090 and the first and second targets 2056, 2060 project the images of the targets to the patient's eye 2064, the patient may interact with those images to align a feature of the patient's eye 2064 with an axis of the alignment device 2008. In the embodiment illustrated by FIG. 55, the patient aligns the line-of-sight of the eye 2064 with the patient viewing axis 2072 of the alignment device 2008.

Techniques for aligning the line of sight of the patient's eye 2064 with the instrument axis have been discussed above. In the context of the embodiment of FIG. 55, the patient is positioned such that the optical path 2076 intersects the patient's eye 2064. In one method, the patient is instructed to focus on the first target 2056. Motion is provided between the patient's eye 2064 and the optical path 2076 (and therefore between the patient's eye 2064 and the targets 2056, 2060). The relative motion between the patient's eye 2064 and the targets 2056, 2060 may be provided by the patient moving his or her head with respect to the patient viewing axis 2072. Alternatively, the patient may be enabled to move all or a portion of the surgical system 2000 while the patient remains stationary. As discussed above, when the first and second targets 2056, 2060 appear aligned (e.g., the L patterns 2085, 2086 merge to form a cross), the line-of-sight of the patient is aligned with the patient viewing axis 2072, the optical path 2076, and the axis 2052 of the alignment module 2020.

Although aligning the eye may be sufficient to provide relatively precise placement of the masks described herein, one or both of the marking module 2024 and the image capture module 2028 may be included to assist the surgeon in placing a mask after the eye 2064 has been aligned. At least one of the marking module 2024 and the image capture module 2028 may be used to correlate the line-of-sight of the patient's eye 2064, which is not otherwise visible, with a visual cue, such as a visible physical feature of the patient's eye, a marker projected onto the eye or an image of the eye, or a virtual image of a marker visible to the surgeon, or any combination of the foregoing. As is discussed in more detail below, the virtual image may be an image that is directed toward the surgeon's eye that appears from the surgeon's point of view to be on the eye 2064 at a pre-selected location.

In one embodiment, the marking module 2024 is configured to produce an image, sometimes referred to herein as a "marking image", that is visible to the surgeon and that is assists the surgeon in placing a mask or performing another surgical procedure after the line of sight of the eye 2064 has been located. The marking module 2024 of the alignment device 2008 shown includes a marking target 2120 and a marking target illuminator 2124. The marking target illuminator 2124 preferably is a source of light, such as any of those discussed above in connection with the target illuminator 2090.

FIG. 55 shows that in one embodiment, the marking target 2120 is a structure configured to produce a marking image when light is projected onto the marking target 2120. The marking target 2120 may be similar to the targets 2056, 2060. In some embodiments, the marking target 2120 is a glass reticle with a suitable geometrical pattern formed thereon. The pattern formed on the marking target 2120 may be a clear two dimensional shape that is surrounded by one or more opaque regions. For example, a clear annulus of selected width surrounded by opaque regions could be provided. In another embodiment, the marking target 2120 may be a glass reticle with an opaque two dimensional shape surrounded by substantially clear regions. As discussed below, in other embodiments, the marking target 2120 need not be made of glass and need not have a fixed pattern. The marking target 2120 may be located in any suitable location with respect to the beamsplitter 2080 or the alignment device 2008 as discussed below.

FIG. 55 shows that in one embodiment, the marking image is generated in a manner similar to the manner in which the images of the first and second targets 2056, 2060 are generated. In particular, the marking target 2124 and the marking target illuminator 2124 cooperate to produce, generate, or project the marking image along a marking image axis 2128. The marking image is conveyed by light along the axis 2128. The marking target illuminator 2124 casts light toward the marking target 2120 in a direction indicated by an arrow 2132. The marking target 2120 interacts with the light cast by the marking target illuminator 2124, e.g., by at least one of transmitting, absorbing, filtering, and attenuating at least a portion of the light. An arrow 2136 indicates the direction along which the marking image generated by the interaction of the marking target illuminator 2124 and the marking target 2120 is conveyed. The marking image preferably is conveyed along the marking axis 2128. In the illustrated embodiment, the marking target 2120 is located off of the axis 2052 and the image of the marking target initially is cast in a direction generally perpendicular to the axis 2052.

A beamsplitter 2140, to be discussed below in connection with the image capture module 2028, is positioned on the marking axis 2128 in the embodiment of FIG. 55. However, the beamsplitter 2140 is configured to be substantially transparent to light being transmitted along the marking axis 2128 from the direction of the marking target 2120. Thus, the light conveying the marking image is substantially entirely transmitted beyond the beamsplitter 2140 along the marking axis 2128 toward the axis 2052 as indicated by an arrow 2144. Thus, the beamsplitter 2140 generally does not affect the marking image. A surface of the beamsplitter 2102 that faces the marking target 2120 is reflective to light. Thus, the light conveying the marking image is reflected and thereafter is conveyed along the axis 2052 as indicated by the arrow 2106. The surface of the beamsplitter 2080 that faces the beamsplitter 2102 also is reflective to at least some light (e.g., 70 percent of the incident light, as discussed above). Thus, the light conveying the marking image is reflected and thereafter is conveyed along the patient viewing axis 2072 toward the patient's eye 2064 as indicated by the arrow 2148. Thus, a marking image projected from the marking target 2120 may be projected onto the patient's eye 2064.

As discussed more fully below, projecting the marking image onto the patient's eye 2064 may assist the surgeon in accurately placing a mask. For example, the surgeon may be assisted in that the location of line-of-sight of the patient's eye (or some other generally invisible feature of the eye 2064) is correlated with a visible feature of the eye, such as the iris or other anatomical feature. In one technique, the marking image is a substantially circular ring that has a diameter that is greater than the size of the inner periphery of the iris under surgical conditions (e.g., the prevailing light and the state of dilation of the patient's eye 2064). In another technique, the marking image is a substantially circular ring that has a diameter that is less than the size of the outer periphery of the iris under surgical conditions (e.g., light and dilation of the eye 2064). In another technique, the marking image is a substantially circular ring that has a size that is correlated to another feature of the eye 2064, e.g., the limbus of the eye.

In one embodiment of the system 2000, a marking module is provided that includes a secondary marking module. The secondary marking module is not routed through the optics of associated with the alignment device 2008. Rather, the secondary marking module is coupled with the alignment device 2008. In one embodiment, the secondary marking module includes a source of radiant energy, e.g., a laser or light source similar to any of these discussed herein. The source of radiant energy is configured to direct a plurality of spots (e.g., two, three, four, or more than four spots) onto the patient's eye 2064. The spots preferably are small, bright spots. The spots indicate positions on the eye 2064 that correlate with a feature of a mask, such as an edge of a mask, when the mask is in the correct position with respect to the line-of-sight of the eye 2064. The spots can be aligned with the projected marking target such that they hit at a selected location on the projected marking target (e.g., circumferentially spaced locations on the inner edge, on the outer edge, or on both the inner and outer edges). Thus, the marking module may give a visual cue as to the proper positioning of a mask that is correlated to the location of the line-of-sight without passing through the optics of the alignment device. The visual cue of the secondary marking module may be coordinated with the marking image of the marking module 2024 in some embodiments.

In some techniques, it may be beneficial to increase the visibility of a visual cue generated for the benefit of the surgeon (e.g., the reflection of the image of the marking target 2120) on the eye 2064. In some cases, this is due to the generally poor reflection of marking images off of the cornea. Where reflection of the marking image off of the cornea is poor, the reflection of the image may be quite dim. In addition, the cornea is an off-center aspherical structure, so the corneal reflection (purkinje images) may be offset from the location of the intersection of the visual axis and the corneal surface as viewed by the surgeon.

One technique for increasing the visibility of a visual cue involves applying a substance to the eye that can react with the projected image of the marking target 2120. For example, a dye, such as fluorescein dye, can be applied to the surface of the eye. Then the marking target illuminator 2124 may be activated to cause an image of the marking target 2120 to be projected onto the eye, as discussed above. In one embodiment, the marking target illuminator 2124 is configured to project light from all or a discrete portion of the visible spectrum of electromagnetic radiant energy, e.g., the wavelengths corresponding to blue light, to project the image of the marking target 2120 onto the eye 2064. The projected image interacts with the dye and causes the image of the marking target 2120 to be illuminated on the surface of the cornea. The presence of the dye greatly increases the visibility of the image of the marking target. For example, where the marking target 2120 is a ring, a bright ring will be visible to the surgeon because the light causes the dye to fluoresce. This technique substantially eliminates errors in placement of a mask due to the presence of the purkinje images and may generally increase the brightness of the image of the marking target 2120.

Another technique for increasing the visibility of a visual cue on the eye involves applying a visual cue enhancing device to at least a portion of the anterior surface of the eye 2064. For example, in one technique, a drape is placed over the cornea. The drape may have any suitable configuration. For example, the drape may be a relatively thin structure that will substantially conform to the anterior structure of the eye. The drape may be formed in a manner similar to the formation of a conventional contact lens. In one technique, the drape is a contact lens. The visual cue enhancing device preferably has suitable reflecting properties. In one embodiment, the visual cue enhancing device diffusely reflects the light projecting the image of the marking target 2120 onto the cornea. In one embodiment, the visual cue enhancing device is configured to interact with a discrete portion of the visible spectrum of electromagnetic radiant energy, e.g., the wavelengths thereof corresponding to blue light.

As discussed above the alignment device 2008 shown in FIG. 55 also includes an image capture module 2028. Some variations do not include the image capture module 2028. The image capture module 2028 of the surgical system 2000 is capable of capturing one or more images of the patient's eye 2064 to assist the surgeon in performing surgical procedures on the eye 2064. The image capture module 2028 preferably includes a device to capture an image, such as a camera 2200 and a display device 2204 to display an image. The display device 2204 may be a liquid crystal display. The image capture module 2028 may be controlled in part by the control device 2032 of the surgical system 2000. For example, the computer 2036 may be employed to process images captured by the camera 2200 and to convey an image to the display device 2204 where it is made visible to the surgeon. The computer 2036 may also direct the operation of or be responsive to at least one of the camera 2200, the display device 2204, the trigger 2042, and any other component of the image capture module 2028.

The camera 2200 can be any suitable camera. One type of camera that can be used is a charge-coupled device camera, referred to herein as a CCD camera. One type of CCD camera incorporates a silicon chip, the surface of which includes light-sensitive pixels. When light, e.g., a photon or light particle, hits a pixel, an electric charge is registered at the pixels that can be detected. Images of sufficient resolution can be generated with a large array of sensitive pixels. As discussed more fully below, one advantageous embodiment provides precise alignment of a selected pixel (e.g., one in the exact geometric center of the display device 2204) with the axis 2052. When such alignment is provided, the marking module may not be needed to align a mask with the line-of-sight of the eye 2064.

As discussed above, an image captured by the camera 2200 aids the surgeon attempting to align a mask, such as any of the masks described herein, with the eye 2064. In one arrangement, the image capture module 2028 is configured to capture an image of one or more physical attributes of the eye 2064, the location of which may be adequately correlated to the line-of-sight of the eye 2064. For example, the image of the patient's iris may be directed along the patient viewing axis 2072 to the beamsplitter 2080 as indicated by the arrow 2148. As mentioned above, a side of the beamsplitter 2080 that faces the beamsplitter 2080 is reflective to light transmitted from the eye 2064. Thus, at least a substantial portion of the light conveying the image of the iris of the eye 2064 is reflected by the beamsplitter 2080 and is conveyed along the axis 2052 toward the beamsplitter 2102, as indicated by the arrow 2106. As discussed above, the surface of the beamsplitter 2102 facing the beamsplitter 2080 is reflective to light. Thus, substantially all of the light conveying the image of the iris is reflected by the beamsplitter 2102 and is conveyed along the marking axis 2128 toward the beamsplitter 2140, as indicated by the arrow 2144. The surface of the beamsplitter 2140 facing the beamsplitter 2102 and the camera 2200 is reflective to light. Thus, substantially all of the light conveying the image of the iris is reflected along an image capture axis 2212 that extends between the beamsplitter 2140 and the camera 2200. The light is conveyed along an image capture axis 2212 as indicated by an arrow 2216.

The image captured by the camera 2200 is conveyed to the computer 2036 by way of a signal line 2040a. The computer 2036 processes the signal in a suitable manner and generates signals to be conveyed along a signal line 2040b to the display device 2204. Any suitable signal line and computer or other signal processing device can be used to convey signals from the camera 2200 to the display device 2204. The signal lines 2040a, 2040b need not be physical lines. For example, any suitable wireless technology may be used in combination with or in place of physical lines or wires.

The capturing of the image by the camera 2200 may be triggered in any suitable way. For example, the trigger 2042 may be configured to be manually actuated. In one embodiment, the trigger 2042 is configured to be actuated by the patient when his or her eye 2064 is aligned (e.g., when the targets 2056, 2060 are aligned, as discussed above). By enabling the patient to trigger the capturing of the image of the eye 2064 by the image capture module 2028, the likelihood of the eye 2064 moving prior to the capturing of the image is greatly reduced. In another embodiment, another person participating in the procedure may be permitted to trigger the capturing of the image, e.g., on the patient's cue. In another embodiment, the control device 2032 may be configured to automatically capture the image of the patient's eye 2064 based on a predetermined criteria.

The display device 2204 is configured to be illuminated to direct an image along the axis 2052 toward the beamsplitter 2080 as indicated by an arrow 2208. The surface of the beamsplitter 2080 that faces the display device 2204 preferably is reflective to light directed from the location of the beamsplitter 2080. Thus, the image on the display 2052 is reflected by the beamsplitter 2080 toward an eye 2212 of the surgeon as indicated by an arrow 2216. The beamsplitter 2080 preferably is transparent from the perspective of the surgeon's eye 2212. Thus, the surgeon may simultaneously view the patient's eye 2064 and the image on the display device 2204 in one embodiment. In one embodiment where both the marking module 2024 and the image capture module 2028 are present, the marking image may be projected at the same time that an image is displayed on the display device 2204. The marking image and the image on the display will appear to both be on the patient's eye. In one arrangement, they have the same configuration (e.g., size and shape) and therefore overlap. This can reinforce the image from the perspective of the surgeon, further increasing the visibility of the visual cue provided by the marking image.

The display device 2204 is located at a distance 2220 from the beamsplitter 2080. The patient is located a distance 2224 from the axis 2052. Preferably the distance 2220 is about equal to the distance 2224. Thus, both the display device 2204 and the patient's eye 2064 are at the focal length of the surgical viewing device 2004. This assures that the image generated by the display device 2204 is in focus at the same time that the patient's eye is in focus.

In one embodiment, the system 2000 is configured to track movement of the patient's eye 2064 during the procedure. In one configuration, the trigger 2042 is actuated by the patient when the eye 2064 is aligned with an axis of the alignment device 2008. Although a mask is implanted shortly thereafter, the patient's eye is not constrained and may thereafter move to some extent. In order to correct for such movement, the image capture module 2028 may be configured to respond to such movements by moving the image formed on the display device 2204. For example, a ring may be formed on the display device 2204 that is similar to those discussed above in connection with the marking target 2120. The beamsplitter 2080 enables the surgeon to see the ring visually overlaid on the patient's eye 2064. The image capture module 2028 compares the real-time position of the patient's eye 2064 with the image of the eye captured when the trigger 2042 is actuated. Differences in the real-time position and the position captured by the camera 2200 are determined. The position of the ring is moved an amount corresponding to the differences in position. As a result, from the perspective of the surgeon, movements of the ring and the eye correspond and the ring continues to indicate the correct position to place a mask.

As discussed above, several variations of the system 2000 are contemplated. A first variation is substantially identical to the embodiment shown in FIG. 55, except as set forth below. In the first variation, the video capture module 2028 is eliminated. This embodiment is similar to that set forth above in connection with FIG. 51. In the arrangement of FIG. 55, the marking module 2024 is configured to project the marking target onto the surface of the patient's eye. This variation is advantageous in that it has a relatively simple construction. Also, this variation projects the marking image onto the surface of the cornea, proximate the surgical location.

In one implementation of the first variation, the marking module 2024 is configured to display the marking image to the surgeon's eye 2212 but not to the patient's eye 2064. This may be provided by positioning the marking target 2120 approximately in the location of the display device 2204. The marking image may be generated and presented to the surgeon in any suitable manner. For example, the marking target 2120 and marking target illuminator 2124 may be repositioned so that they project the image of the marking target 2120 as indicated by the arrows 2208, 2216. The marking target 2120 and the marking target illuminator 2124 may be replaced by a unitary display, such as an LCD display. This implementation of the first variation is advantageous in that the marking image is visible to the surgeon but is not visible to the patient. The patient is freed from having to respond to or being subject to the marking image. This can increase alignment performance by increasing patient comfort and decreasing distractions, thereby enabling the patient to remain still during the procedure.

In another implementation of the first variation, a dual marking image is presented to the eye 2212 of the surgeon. In one form, this implementation has a marking module 2024 similar to that shown in FIG. 55 and discussed above, except as set forth below. A virtual image is presented to the surgeon's eye 2212. In one form, a virtual image generation surface is positioned in substantially the same location as the display device 2204. The surface may be a mirror, another reflective surface, or a non-reflective surface. In one embodiment, the display device 2204 is a white card. A first fraction of the light conveying the marking image is reflected by the beamsplitter 2080 to the patient's eye 2064. The marking image is thus formed on the patient's eye. A second fraction of the light conveying the marking image is transmitted to the virtual image generation surface. The marking image is formed on or reflected by the virtual image generation surface. The marking target thus also is visible to the surgeon's eye 2212 in the form of a virtual image of the target. The virtual image and the marking image formed on the patient's eye are both visible to the surgeon. This implementation of the first variation is advantageous in that the virtual image and the marking image of the marking target are visible to the surgeon's eye 2212 and are reinforced each other making the marking image highly visible to the surgeon.

In a second variation, the marking module 2024 is eliminated. In this embodiment, the image capture module 2028 provides a visual cue for the surgeon to assist in the placement of a mask. In particular, an image can be displayed on the display device 2204, as discussed above. The image can be generated in response to the patient actuating the trigger 2042. In one technique, the patient actuates the trigger when the targets 2056, 2060 appear aligned, as discussed above. In this variation, care should be taken to determine the position of the display device 2204 in the alignment device because the image formed on the display device 2204 is to give the surgeon a visual cue indicating the location of the line-of-sight of the patient. In one embodiment, the display device 2204 is carefully coupled with the alignment module so that the axis 2052 extends through a known portion (e.g., a known pixel) thereof. Because the precise location of the axis 2052 on the display device 2204 is known, the relationship of the image formed thereon to the line-of-sight of the patient is known.

Figure 56:
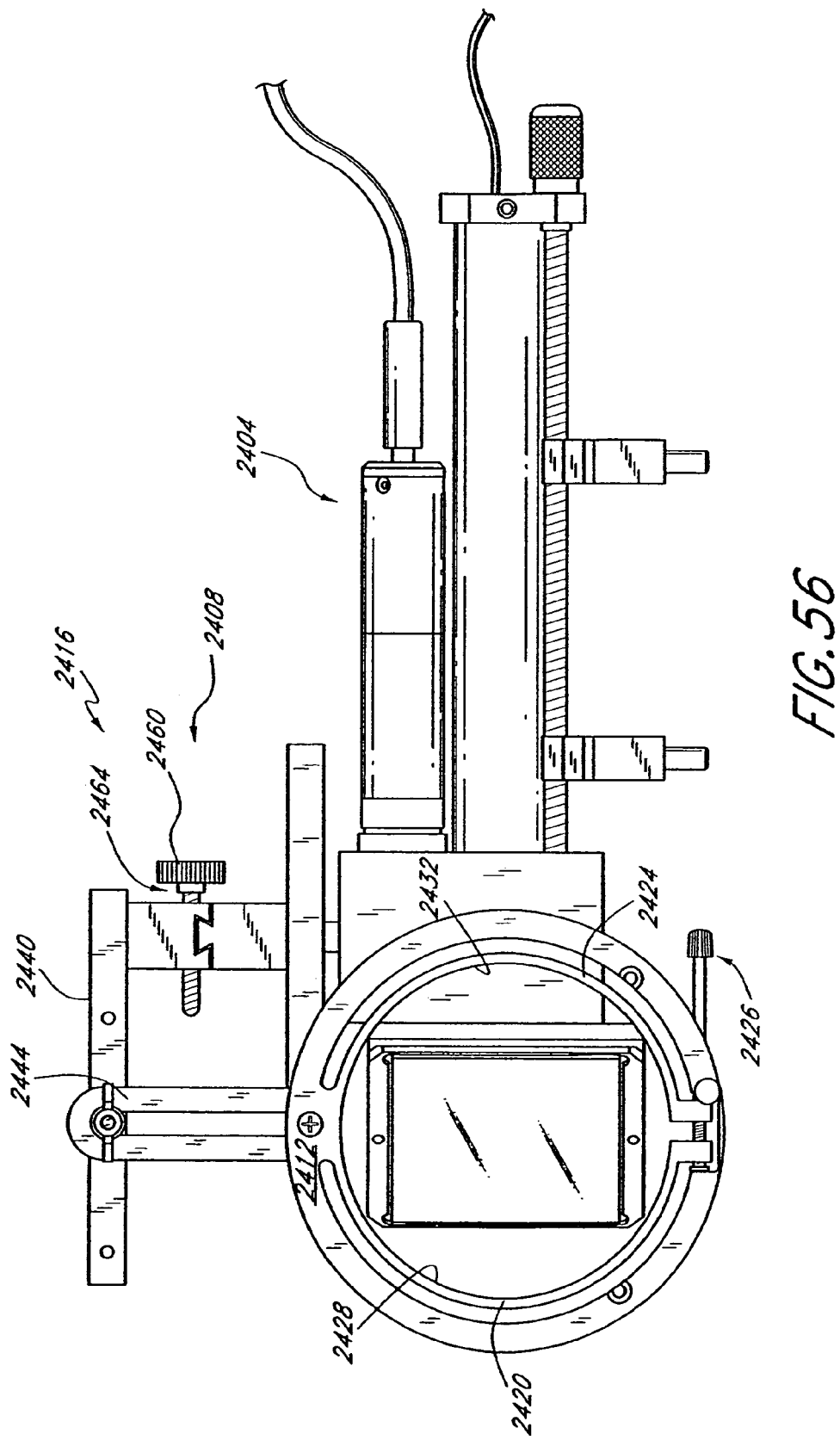
FIG. 56 is a top view of another embodiment of a surgical system that includes an alignment device and a clamp configured to couple the alignment device with a surgical viewing device.

FIG. 56 shows a portion of a surgical system 2400 that is similar to the surgical system 2000 discussed above except as set forth below. The surgical system 2400 may be modified according to any of the variations and embodiments hereinbefore described.

The portion of the surgical system 2400 is shown from the surgeon's viewpoint in FIG. 56. The surgical system 2400 includes an alignment device 2404 and a fixture 2408. The alignment device 2404 is similar to the alignment device 2008 discussed above, except as set forth below. The surgical system 2400 is shown without a surgical microscope or other viewing device, but is configured to be coupled with one by way of the fixture 2408.

The fixture 2408 may take any suitable form. In the illustrated embodiment, the fixture 2408 includes a clamp 2412, an elevation adjustment mechanism 2416, and suitable members to interconnect the clamp 2408 and the mechanism 2416. In the embodiment of FIG. 56, the clamp 2412 is a ring clamp that includes a first side portion 2420, a second side portion 2424, and a clamping mechanism 2426 to actuate the first and second side portion 2420, 2424 with respect to each other. The first side portion 2420 has a first arcuate inner surface 2428 and the second side portion 2424 has a second arcuate inner surface 2432 that faces the first arcuate inner surface 2428. The clamping mechanism 2426 is coupled with each of the first and second side portions 2420, 2424 to cause the first and second arcuate inner surfaces 2428, 2432 to move toward or away from each other. As the first and second arcuate inner surfaces 2428, 2432 move toward each other they apply a force to a structure, such as a portion of a surgical microscope, placed between the first and second arcuate inner surfaces 2428, 2432. In one embodiment, the force applied by the first and second arcuate inner surfaces 2428, 2432 is sufficient to clamp the alignment device 2404 with respect to a surgical viewing aid. In one embodiment, the clamp 2412 is configured to couple with any one of (or more than one of) the currently commercially available surgical microscopes.

The fixture 2408 preferably also is configured to suspend the alignment device 2404 at an elevation below the clamp 2412. In the illustrated embodiment, a bracket 2440 is coupled with the clamp 2412, which is an L-shaped bracket in the illustrated embodiment with a portion of the L extending downward from the clamp 2412. FIG. 56 shows the L-shaped bracket spaced laterally from the clamp 2412 by a spacer 2444. In one embodiment, the bracket 2440 is pivotably coupled with the spacer 2444 so that the alignment device 2404 can be easily rotated out of the field of view of the surgical microscope or viewing aid, which is visible through the spaced defined between the surfaces 2428, 2432.

Preferably the fixture 2408 is also configured to enable the alignment device 2404 to be positioned at a selected elevation within a range of elevations beneath the clamp 2412. The elevation of the alignment device 2404 may be easily and quickly adjusted by manipulating a suitable mechanism. For example, manual actuation may be employed by providing a knob 2460 coupled with a rack-and-pinion gear coupling 2464. Of course the rack-and-pinion gear coupling 2464 can be actuated by another manual device that is more remote, such as by a foot pedal or trigger or by an automated device.

Figure 57:
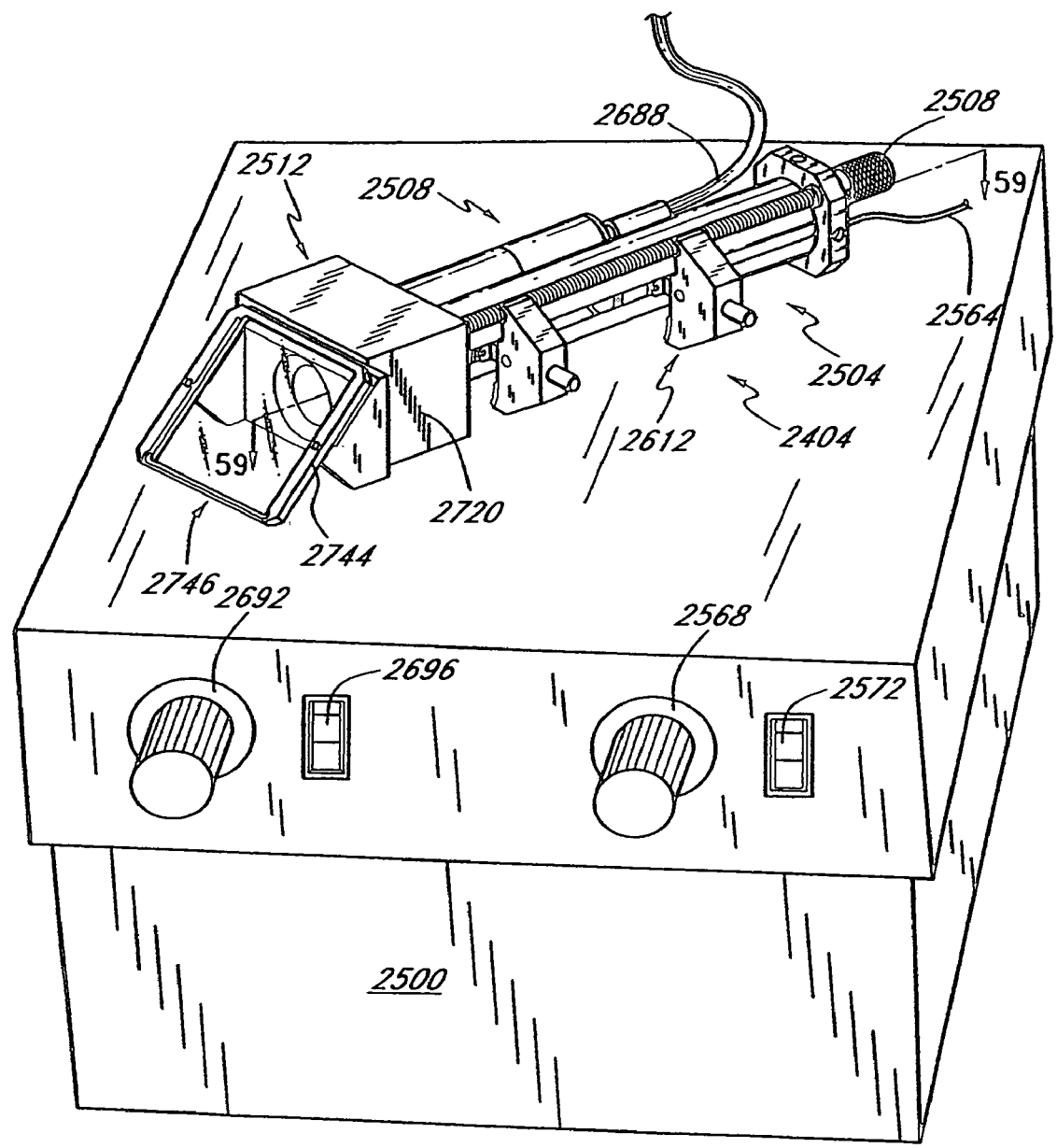
FIG. 57 is a perspective view of the alignment device shown in FIG. 56.
Figure 58:
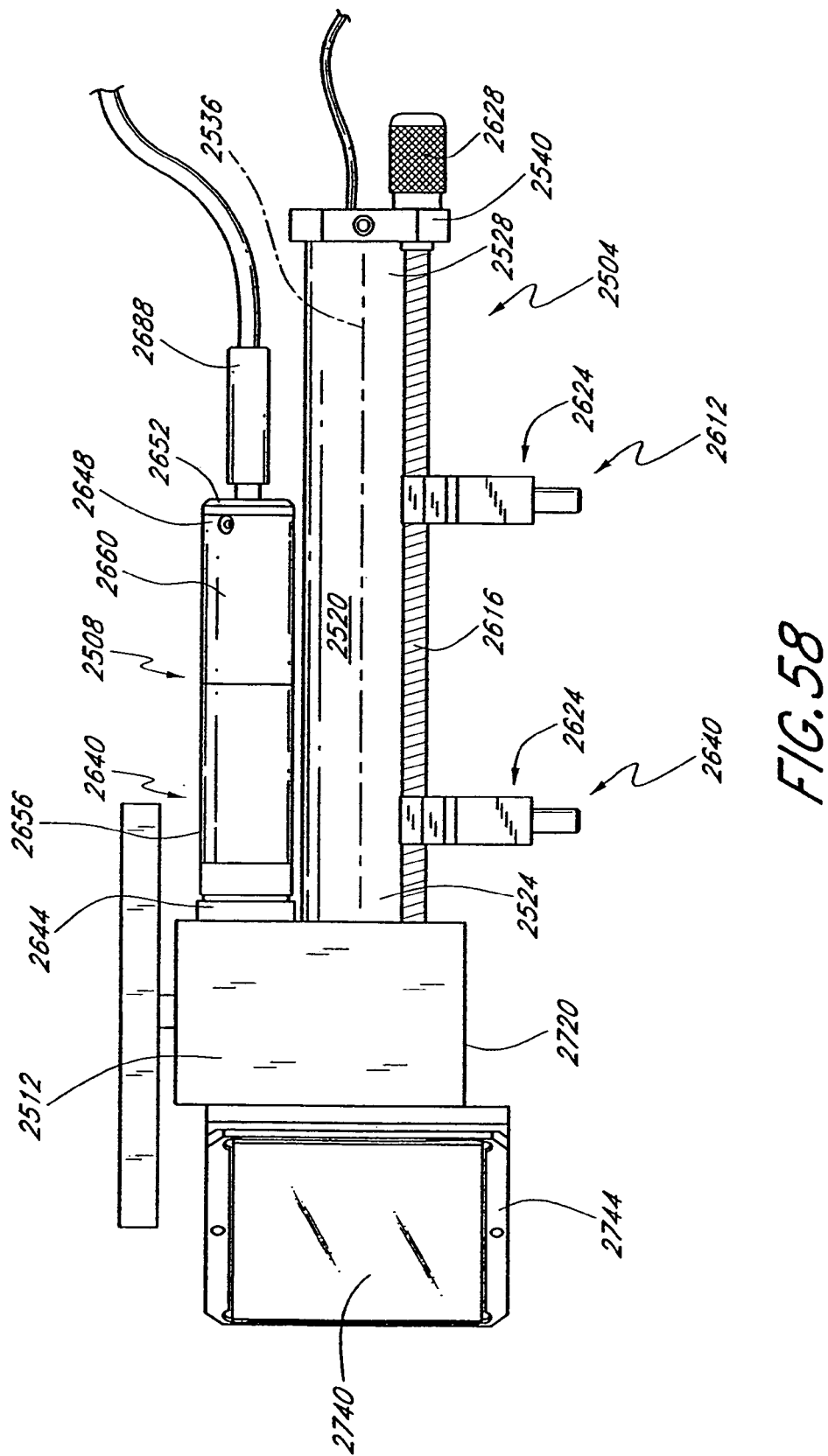
FIG. 58 is a top view of the alignment device shown in FIG. 57.
Figure 59:
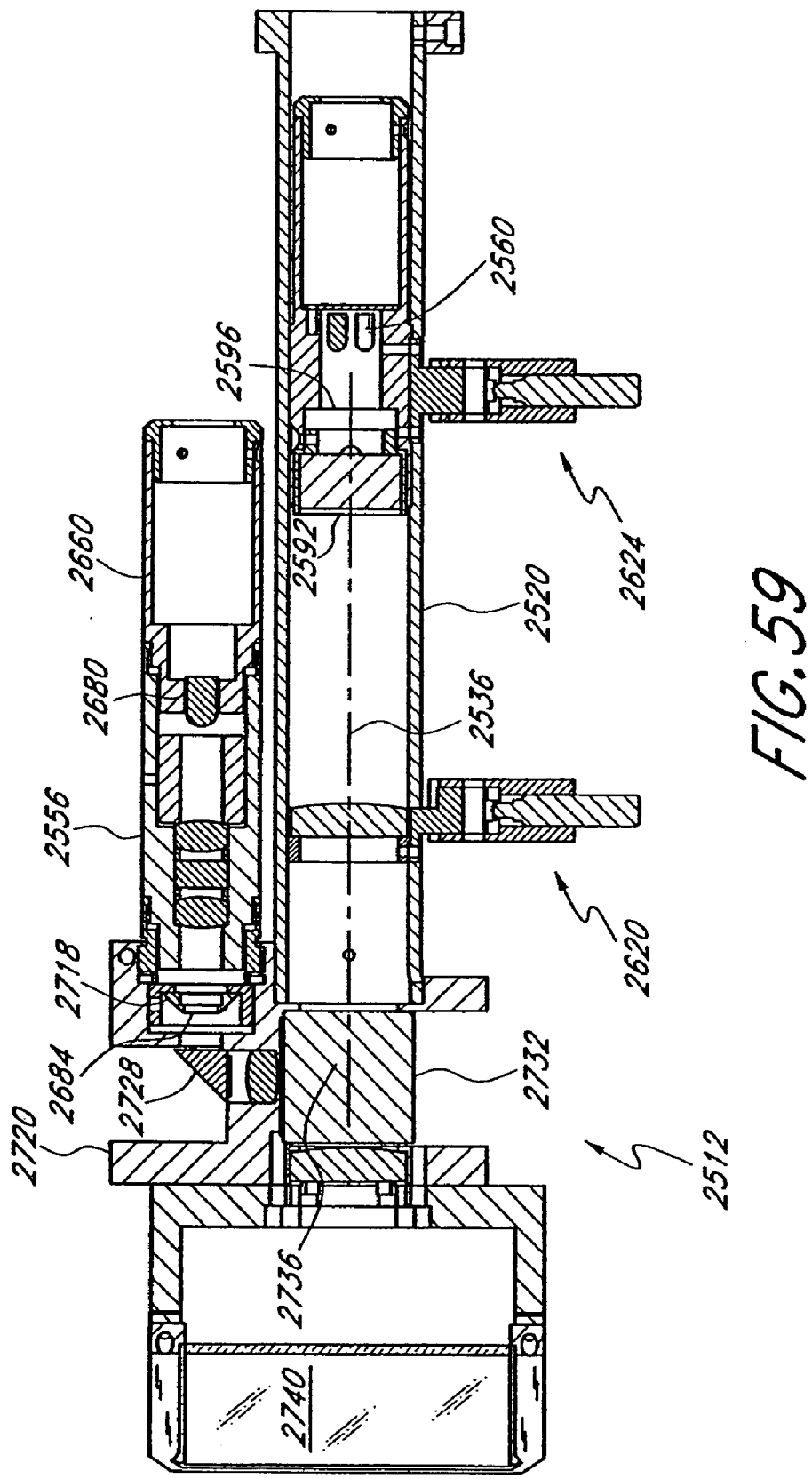
FIG. 59 is a schematic view of internal components of the alignment devices of FIG. 57.

FIGS. 57-59 show further details of the alignment device 2404. The alignment device 2404 is operatively coupled with an illuminator control device 2500 and includes an alignment module 2504, a marking module 2508, and an image routing module 2512. As discussed below, the illuminator control device 2500 controls light or energy sources associated with the alignment control device 2404. In some embodiments, the illuminator control device 2500 forms a part of a computer or other signal processing device, similar to the computer 2036 discussed above.

The alignment module 2504 is similar to the alignment module 2020 except as set forth below. The alignment module 2504 includes a housing 2520 that extends between a first end 2524 and a second end 2528. The first end 2524 of the housing 2520 is coupled with the image routing module 2512 and interacts with the image routing module 2512 in a manner described below. The housing 2520 includes a rigid body 2532 that preferably is hollow. An axis 2536 extends within the hollow portion of the housing 2520 between the first and second ends 2524, 2528. In the illustrated embodiment, the second end 2528 of the housing 2520 is enclosed by an end plate 2540.

The housing 2520 is configured to protect a variety of components that are positioned in the hollow spaced defined therein. In one embodiment, a target illuminator 2560 is positioned inside the housing 2520 near the second end 2528 thereof. A power cable 2564 (or other electrical conveyance) that extends from the end plate 2540 electrically connects the target illuminator 2560 to a power source. The target illuminator 2560 could also be triggered and powered by a wireless connection. In one arrangement, the power source forms a portion of the illuminator control device 2500 to which the power cable 2564 is connected. Power may be from any suitable power source, e.g., from a battery or electrical outlet of suitable voltage.

As discussed above, the illuminator control device 2500 enables the surgeon (or other person assisting in a procedure) to control the amount of energy supplied to the target illuminator 2560 in the alignment module 2504. In one embodiment, the illuminator control device 2500 has a brightness control so that the brightness of the target illumination 2560 can be adjusted. The brightness control may be actuated in a suitable manner, such as by a brightness control knob 2568. The brightness control may take any other suitable form to provide manual analog (e.g., continuous) adjustment of the amount of energy applied to the target illuminator 2560 or to provide manual digital (e.g., discrete) adjustment of the amount of energy applied to the target illuminator 2560. In some embodiments, the brightness control may be adjustable automatically, e.g., under computer control. The illuminator control device 2500 may also have an on-off switch 2572 configured to selectively apply and cut off power to the target illuminator 2560. The on-off switch 2572 may be operated manually, automatically, or in a partially manual and partially automatic mode. The brightness control and on-off switch could be controlled wirelessly in another embodiment.

Also located in the housing 2520 are a first target 2592, a second target 2596, and a lens 2600. As discussed above, the first and second targets 2592, 2596 are configured to present a composite image to the patient's eye such that the patient may align the line-of-sight of the eye with an axis (e.g., the axis 2536) of the alignment module 2504. The first and second targets 2592, 2596 are similar to the targets discussed above. In particular, the alignment target 2081, which includes two targets on opposite ends of a single component, may be positioned within the housing 2520.

The lens 2600 may be any suitable lens. Preferably the lens 2600 is configured to sharply focus one or both of the images of the first and second targets 2592, 2596 in a manner similar to the focus of the targets 2056, 2060, discussed above.

In one embodiment, the alignment module 2504 is configured such that the position of the first and second targets 2592, 2596 within the housing 2520 can be adjusted. The adjustability of the first and second targets 2592, 2596 may be provided with any suitable arrangement. FIGS. 57-58 shows that in one embodiment the alignment module 2504 includes a target adjustment device 2612 to provide rapid gross adjustment and fine adjustment of the positions of the targets 2592, 2596 within the housing 2520.

In one embodiment, the target adjustment device 2612 includes a support member 2616 that extends along at least a portion of the housing 2520 between the first end 2524 and the second end 2528. In one embodiment, the support member 2616 is coupled with the end plate 2540 and with the image routing module 2512. In one embodiment, the target adjustment device 2612 includes a lens fixture 2620 that is coupled with the lens 2600 and a target fixture 2624 that is coupled with the first and second targets 2592, 2596. In another embodiment, each of the first and second targets 2592, 2596 is coupled with a separate target fixture so that the targets may be individually positioned and adjusted. The lens 2600 may be adjustable as shown, or in a fixed position. Movement of the lens and the targets 2592, 2596 enable the patterns on the targets 2592, 2596 to be brought into focus from the patient's point of view.

In one arrangement, the support member 2616 is a threaded rod and each of the first and second target fixtures 2620, 2624 has a corresponding threaded through hole to receive the threaded support member 2616. Preferably an adjustment device, such as a knob 2628 is coupled with the threaded support member 2616 so that the support member 2616 may be rotated. The knob 2628 may be knurled to make it easier to grasp and rotate. Rotation of the support member 2616 causes the first and second target fixtures 2620, 2624 to translate on the support member 2616 along the outside of the housing 2520. The movement of the first and second target fixtures 2620, 2624 provides a corresponding movement of the first and second targets 2592, 2596 within the housing 2520.

In one embodiment a quick release mechanism 2640 is provided to enable the first and second target fixtures 2620, 2624 selectively to clamp and to release the support member 2616. The quick release mechanism 2640 can be a spring loaded clamp that causes the through holes formed in the first and second target fixtures 2620, 2624 to open to create a gap through which the support member 2616 can pass. When the first and second target fixtures 2620, 2624 are removed from the support member 2616, the can be quickly moved to another position on the support member 2616. After rapid repositioning, fine positioning of the first and second target fixtures 2620, 2624 may be achieved with by turning the support member 2616.

As discussed above, the alignment device 2404 also includes a marking module 2508 that is similar to the marking module 2024 described above, except as set forth below. The marking module includes a housing 2642 that is generally rigid and that defines a hollow space within the housing. The housing 2642 includes a first end 2644 that is coupled with the image routing module 2512 and a second end 2648 that is closed by an end plate 2652. In one embodiment, the housing 2642 includes a first portion 2656 and a second portion 2660. The first and second portions 2656, 2660 preferably are configured to be disengaged from each other so that components located in the hollow space defined in the housing 2642 to be accessed. Such rapid access facilitates servicing and reconfiguring of the components located in the housing 2642. The first portion 2656 extends between the first end 2644 and a midpoint of the housing 2642. The second portion 2660 extends between the first portion 2656 and the second end 2648 of the housing 2642. In one embodiment, the first portion 2656 has a male member with external threads and the second portion 2660 has a female member with internal thread such that the first and second portions 2656, 2660 may be engaged with and disengaged from each other by way of the threads.

As discussed above, the housing 2642 provides a space in which one or more components may be positioned. In the illustrated embodiment, the housing 2642 encloses a marking target illuminator 2680 and a marking target 2684.

The marking target illuminator 2680 may be a suitable source of radiant energy, e.g., a light source, such as an incandescent light, a fluorescent light, a light-emitting diode, or other source of radiant energy. As with the target illuminators discussed above, the marking target illuminator 2680 may include or be coupled with suitable optical components to process the light generated thereby in a useful manner, e.g., by providing one or more filters to modify the light, e.g., by allowing a subset of the spectrum of light energy emitted by the light source (e.g., one or more bands of the electromagnetic spectrum) to be transmitted toward the marking target 2684.

In the illustrated embodiment, the marking target illuminator 2680 is located near the end plate 2652. A power cable 2688 (or other electrical conveyance) that extends from the end plate 2652 electrically connects the marking target illuminator 2680 to a power source. In one arrangement, the power source forms a portion of the illuminator control device 2500 to which the power cable 2688 is connected. Power may be from any suitable power source, e.g., from a battery or electrical outlet of suitable voltage.

As discussed above, the illuminator control device 2500 enables the surgeon (or other person assisting in a procedure) to control the amount of energy supplied to the target illuminator 2680 in the marking module 2508. The illuminator control device 2500 has a brightness control so that the brightness of the marking target illumination 2680 can be adjusted. The brightness control may be actuated in a suitable manner, such as by a brightness control knob 2692. The brightness control may be similar to that discussed above in connection with the brightness control of the target illuminator 2560. The illuminator control device 2500 may also have an on-off switch 2696 configured to selectively apply and cut off power to the marking target illuminator 2680. The on-off switch 2696 may be operated manually, automatically, or in a partially manual and partially automatic mode. Any of the power supply, the brightness control, and the on-off switch may be implemented wirelessly in various other embodiments.

In one embodiment, the marking target 2684 is a reticle, e.g., made of glass, with an annular shape formed thereon. For example, the annular shape formed on the marking target 2684 may be a substantially clear annulus surrounded by opaque regions. In this configuration, light directed toward the marking target 2684 interacts with the marking target 2684 to produce and annular image. In another embodiment, the marking target 2684 may be a substantially clear reticle with an opaque shape, such as an opaque annular shape. The annular image is directed into the image routing device 2684, as discussed further below. The marking target 2684 may be housed in a fixture 2718 that is removable, e.g., when the first portion 2656 and the second portion 2660 of the housing 2642 are decoupled. The first portion 2656 of the housing 2642 is configured to engage the fixture 2718 to relatively precisely position the marking target 2684 with respect to an axis of the housing 2642.

FIG. 59 shows the image routing module 2512 in greater detail. The image routing module 2512 is primarily useful for routing light that conveys the target and marking images to an eye of a patient. The image routing module 2512 provides flexibility in the positioning of the various components of the alignment device 2404. For example, the image routing module 2512 enables the housing 2520 and the housing 2556 to be generally in the same plane and positioned generally parallel to each other. This provides a relatively compact arrangement for the alignment device 2404, which is advantageous in the surgical setting because, as discussed above, it is desirable for the surgeon to be as close to the surgical site as possible. In addition, the compact arrangement of the alignment device 2404 minimizes or at least reduces the extent to which the alignment device 2404 interferes with free movement of the surgeon and others assisting the surgeon.

FIGS. 58 and 59 shows that the image routing module 2512 includes a housing 2720 that is coupled with the first end 2524 and the housing 2520 and with the first end 2644 of the housing 2642. A space defined within the housing 2720 houses a first optic device 2728 and a second optic device 2732. The first optic device 2728 has a reflective surface that faces the marking target 2684 and is configured to reflect light conveying an image of the marking target 2684 toward the second optic device 2732. The first optic device 2728 may be a mirror. The second optic device 2732 has a surface 2736 that faces the first optic device 2728 and is reflective to light from the first optic device 2728. The second optic device 2732 thus reflects light that is directed toward it by the first optic device 2728.

The image routing module 2512 also may include a third optic device 2740 and a frame 2744 coupled with the housing 2720. The frame 2744 is configured to position and orient the third optic device 2740 with respect to the housing 2720. In one embodiment, the third optic device 2740 is a beamsplitter and the frame 2744 holds the third optic device 2740 at about a forty-five degree angle with respect to the axis 2520. In this position, the third optic device 2740 interacts with light reflected by the first surface 2736 of the second optic device 2732. The third optic device 2740 may operate in a manner similar to the beamsplitter 2080 of FIG. 55.

The second optic device 2732 is configured to be transparent to substantially all of the light conveying an image along the axis 2536 such that the image conveyed along the axis 2536 may be directed to the third optic device 2740 and thereafter to an eye of a surgeon, as discussed about in connection with FIG. 55.

Although the image routing device is shown with first, second, and third optic devices 2728, 2732, 2740 to route light conveying images in a particular manner, one skilled in the art will recognize that the image routing device 2512 could have more or fewer optic devices that route the image, depending on the desired geometry and compactness of the alignment device 2404.

A variation of the alignment device 2404 provides a marking module with a secondary marking module not routed through the optics of the alignment device 2404. In one embodiment, the secondary marking module includes a source of radiant energy, e.g., a laser or other light source. The source of radiant energy is configured to direct a plurality of spots (e.g., three, four, or more than four spots) onto the patient's eye. The spots indicate positions on the eye that correlate with an edge of a mask when the mask is in the correct position with respect to the line-of-sight of the eye 2064. The spots can be aligned with the projected marking target such that they hit at a selected location on the projected marking target (e.g., circumferentially spaced locations on the inner edge, on the outer edge, or on both the inner and outer edges). At least a portion of the secondary marking module is coupled with the frame 2744 in one embodiment. A laser of the secondary marking module could be attached to the frame 2744 and suspended therefrom, oriented downward toward the patient's eye. As discussed above, this arrangement provides a secondary device for marking the proper location of a mask with respect to a patient's line of sight after the line of sight has been identified.

Although various exemplary embodiments of apparatuses and methods for aligning a patient's line-of-sight with an axis of an instrument in connection with the application of a mask have been discussed hereinabove, it should be apparent to those skilled in the art that various changes and modifications can be made which will achieve at least some of the advantages of the invention without departing from, the true scope of the invention. These and other obvious modifications are intended to be covered by the appended claims.

V. Masks Configured to Reduce the Visibility of Diffraction Patterns

Many of the foregoing masks can be used to improve the depth of focus of a patient. Various additional mask embodiments are discussed below. Some of the embodiments described below include nutrient transport structures that are configured to enhance or maintain nutrient flow between adjacent tissues by facilitating transport of nutrients across the mask. The nutrient transport structures of some of the embodiments described below are configured to at least substantially prevent nutrient depletion in adjacent tissues. The nutrient transport structures can decrease negative effects due to the presence of the mask in adjacent corneal layers when the mask is implanted in the cornea, increasing the longevity of the masks. The inventors have discovered that certain arrangements of nutrient transport structures generate diffraction patterns that interfere with the vision improving effect of the masks described herein. Accordingly, certain masks are described herein that include nutrient transport structures that do not generate diffraction patterns or otherwise interfere with the vision enhancing effects of the mask embodiments.

Figure 60:
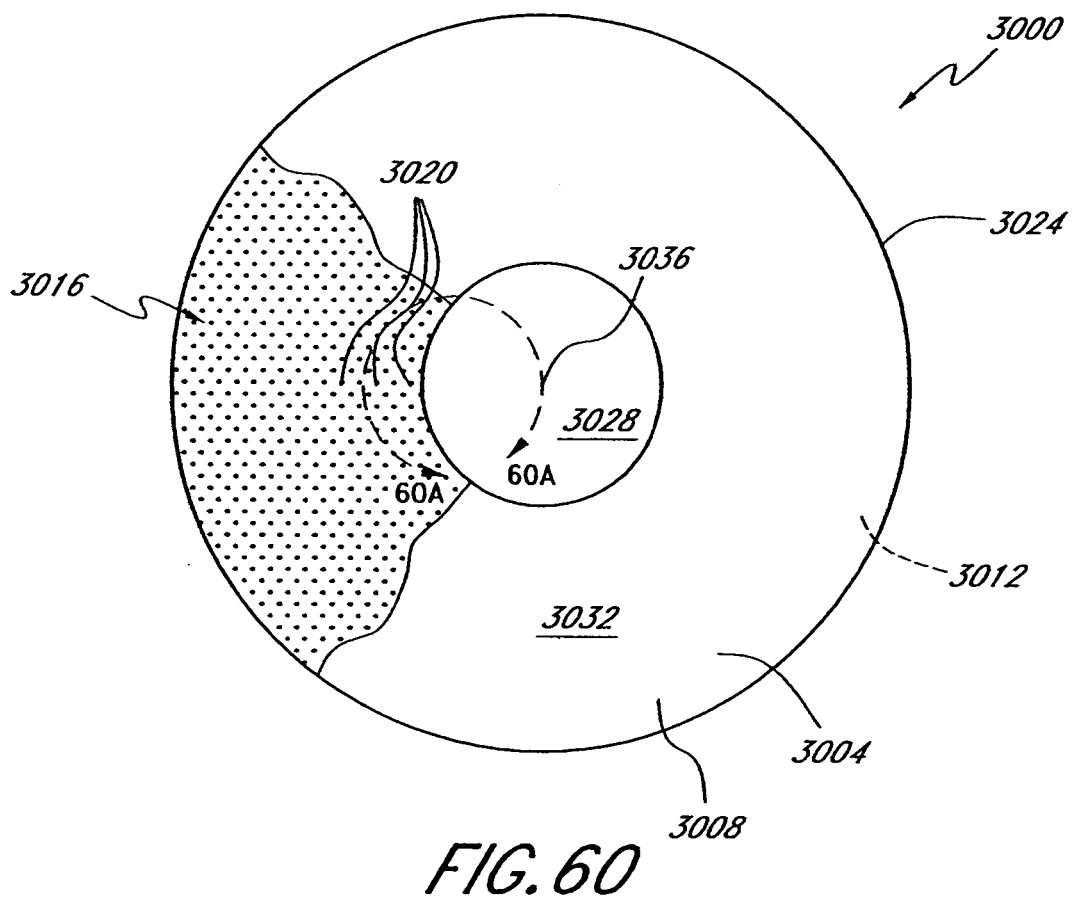
FIG. 60 is a top view of another embodiment of a mask configured to increase depth of focus.
Figure 60A:
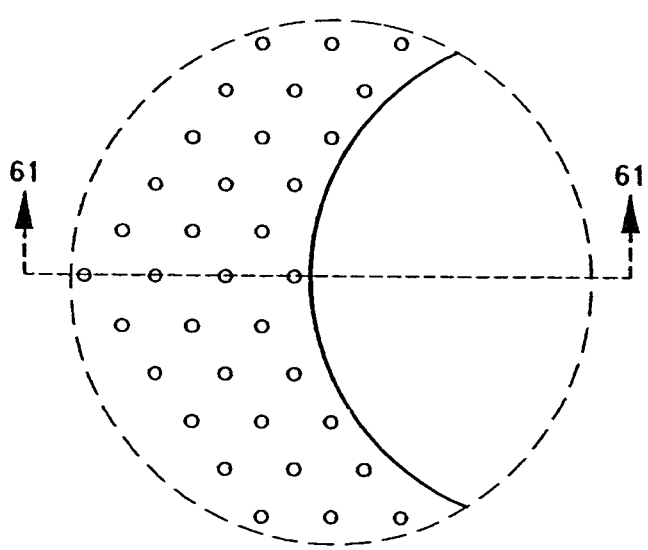
FIG. 60A is an enlarged view of a portion of the view of FIG. 60.
Figure 61A:
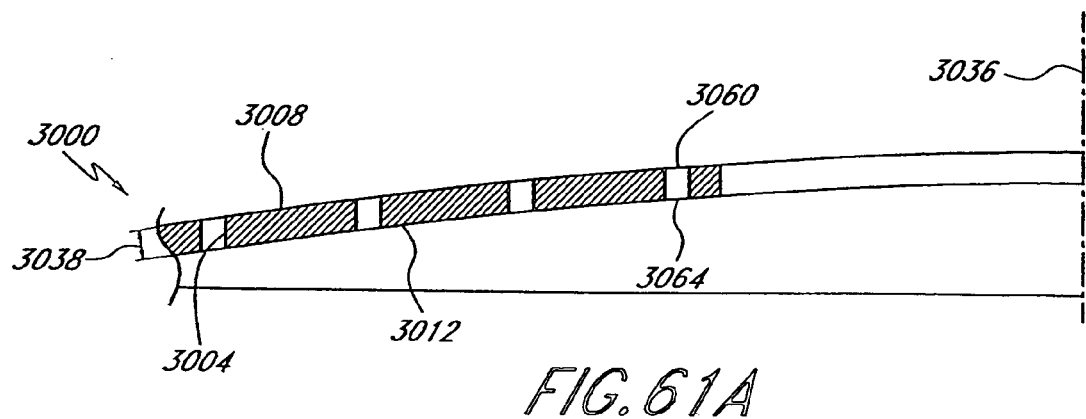
FIG. 61A is a cross-sectional view of the mask of FIG. 60A taken along the section plane 61--61.

FIGS. 60-61 show one embodiment of a mask 3000 configured to increase depth of focus of an eye of a patient suffering from presbyopia. The mask 3000 is similar to the masks hereinbefore described, except as set forth below. The mask 3000 is configured to be applied to an eye of a patient, e.g., by being implanted in the cornea of the patient. The mask 3000 may be implanted within the cornea in any suitable manner, such as those discussed above in connection with FIGS. 53A-54C.

In one embodiment, the mask 3000 includes a body 3004 that has an anterior surface 3008 and a posterior surface 3012. In one embodiment, the body 3004 is capable of substantially maintaining natural nutrient flow between the first corneal layer and the second corneal layer. In one embodiment, the material is selected to maintain at least about ninety-six percent of the natural flow of at least one nutrient (e.g., glucose) between a first corneal layer (e.g., the layer 1410) and a second corneal layer (e.g., the layer 1430). The body 3004 may be formed of any suitable material, including at least one of an open cell foam material, an expanded solid material, and a substantially opaque material. In one embodiment, the material used to form the body 3004 has relatively high water content.

In one embodiment, the mask 3000 includes and a nutrient transport structure 3016. The nutrient transport structure 3016 may comprise a plurality of holes 3020. The holes 3020 are shown on only a portion of the mask 3000, but the holes 3020 preferably are located throughout the body 3004 in one embodiment. In one embodiment, the holes 3020 are arranged in a hex pattern, which is illustrated by a plurality of locations 3020' in FIG. 62A. As discussed below, a plurality of locations may be defined and later used in the later formation of a plurality of holes 3020 on the mask 3000. The mask 3000 has an outer periphery 3024 that defines an outer edge of the body 3004. In some embodiments, the mask 3000 includes an aperture 3028 at least partially surrounded by the outer periphery 3024 and a non-transmissive portion 3032 located between the outer periphery 3024 and the aperture 3028.

Preferably the mask 3000 is symmetrical, e.g., symmetrical about a mask axis 3036. In one embodiment, the outer periphery 3024 of the mask 3000 is circular and has a diameter of less than about 6 mm in one embodiment. In another embodiment, the mask is circular and has a diameter in the range of 4 to 6 mm. In another embodiment, the mask 3000 is circular and has a diameter of less than 4 mm. The outer periphery 3024 has a diameter of about 3.8 mm in another embodiment. In some embodiments, masks that are asymmetrical or that are not symmetrical about a mask axis provide benefits, such as enabling a mask to be located or maintained in a selected position with respect to the anatomy of the eye.

The body 3004 of the mask 3000 may be configured to coupled with a particular anatomical region of the eye. The body 3004 of the mask 3000 may be configured to conform to the native anatomy of the region of the eye in which it is to be applied. For example, where the mask 3000 is to be coupled with an ocular structure that has curvature, the body 3004 may be provided with an amount of curvature along the mask axis 3036 that corresponds to the anatomical curvature. For example, one environment in which the mask 3000 may be deployed is within the cornea of the eye of a patient. The cornea has an amount of curvature that varies from person to person about a substantially constant mean value within an identifiable group, e.g., adults. When applying the mask 3000 within the cornea, at least one of the anterior and posterior surfaces 3008, 3012 of the mask 3000 may be provided with an amount of curvature corresponding to that of the layers of the cornea between which the mask 3000 is applied.

In some embodiments, the mask 3000 has a desired amount of optical power. Optical power may be provided by configuring the at least one of the anterior and posterior surfaces 3008, 3012 with curvature. In one embodiment, the anterior and posterior surfaces 3008, 3012 are provided with different amounts of curvature. In this embodiment, the mask 3000 has varying thickness from the outer periphery 3024 to the aperture 3028.

In one embodiment, one of the anterior surface 3008 and the posterior surface 3012 of the body 3004 is substantially planar. In one planar embodiment, very little or no uniform curvature can be measured across the planar surface. In another embodiment, both of the anterior and posterior surfaces 3008, 3012 are substantially planar. In one embodiment, the body 3004 of the mask 3000 has a thickness 3038 of between about 5 micron and about 10 micron. In one embodiment, the thickness 3038 of the mask 3000 is about 5 micron. In another embodiment, the thickness 3038 of the mask 3000 is about 8 micron. In another embodiment, the thickness 3038 of the mask 3000 is about 10 micron.

Thinner masks generally are more suitable for applications wherein the mask 3000 is implanted at a relatively shallow location in (e.g., close to the anterior surface of) the cornea. In thinner masks, the body 3004 may be sufficiently flexible such that it can take on the curvature of the structures with which it is coupled without negatively affecting the optical performance of the mask 3000. In one application, the mask 3000 is configured to be implanted about 5 um beneath the anterior surface of the cornea. In another application, the mask 3000 is configured to be implanted about 65 um beneath the anterior surface of the cornea. In another application, the mask 3000 is configured to be implanted about 125 um beneath the anterior surface of the cornea. Further details regarding implanting the mask 3000 in the cornea are discussed above in connection with FIGS. 53A-54C.

A substantially planar mask has several advantages over a non-planar mask. For example, a substantially planar mask can be fabricated more easily than one that has to be formed to a particular curvature. In particular, the process steps involved in inducing curvature in the mask 3000 can be eliminated. Also, a substantially planar mask may be more amenable to use on a wider distribution of the patient population (or among different sub-groups of a broader patient population) because the substantially planar mask uses the curvature of each patient's cornea to induce the appropriate amount of curvature in the body 3004.

In some embodiments, the mask 3000 is configured specifically for the manner and location of coupling with the eye. In particular, the mask 3000 may be larger if applied over the eye as a contact lens or may be smaller if applied within the eye posterior of the cornea, e.g., proximate a surface of the lens of the eye. As discussed above, the thickness 3038 of the body 3004 of the mask 3000 may be varied based on where the mask 3000 is implanted. For implantation at deeper levels within the cornea, a thicker mask may be advantageous. Thicker masks are advantageous in some applications. For example, they are generally easier to handle, and therefore are easier to fabricate and to implant. Thicker masks may benefit more from having a preformed curvature than thinner masks. A thicker mask could be configured to have little or no curvature prior to implantation if it is configured to conform to the curvature of the native anatomy when applied.

The aperture 3028 is configured to transmit substantially all incident light along the mask axis 3036. The non-transmissive portion 3032 surrounds at least a portion of the aperture 3028 and substantially prevents transmission of incident light thereon. As discussed in connection with the above masks, the aperture 3028 may be a through-hole in the body 3004 or a substantially light transmissive (e.g., transparent) portion thereof. The aperture 3028 of the mask 3000 generally is defined within the outer periphery 3024 of the mask 3000. The aperture 3028 may take any of suitable configurations, such as those described above in connection with FIGS. 6-42.

In one embodiment, the aperture 3028 is substantially circular and is substantially centered in the mask 3000. The size of the aperture 3028 may be any size that is effective to increase the depth of focus of an eye of a patient suffering from presbyopia. For example, the aperture 3028 can be circular, having a diameter of less than about 2.2 mm in one embodiment. In another embodiment, the diameter of the aperture is between about 1.8 mm and about 2.2 mm. In another embodiment, the aperture 3028 is circular and has a diameter of about 1.8 mm or less.

The non-transmissive portion 3032 is configured to prevent transmission of radiant energy through the mask 3000. For example, in one embodiment, the non-transmissive portion 3032 prevents transmission of substantially all of at least a portion of the spectrum of the incident radiant energy. In one embodiment, the non-transmissive portion 3032 is configured to prevent transmission of substantially all visible light, e.g., radiant energy in the electromagnetic spectrum that is visible to the human eye. The non-transmissve portion 3032 may substantially prevent transmission of radiant energy outside the range visible to humans in some embodiments.

As discussed above in connection with FIG. 3, preventing transmission of light through the non-transmissive portion 3032 decreases the amount of light that reaches the retina and the fovea that would not converge at the retina and fovea to form a sharp image. As discussed above in connection with FIG. 4, the size of the aperture 3028 is such that the light transmitted therethrough generally converges at the retina or fovea. Accordingly, a much sharper image is presented to the eye than would otherwise be the case without the mask 3000.

In one embodiment, the non-transmissive portion 3032 prevents transmission of about 90 percent of incident light. In another embodiment, the non-transmissve portion 3032 prevents transmission of about 92 percent of all incident light. The non-transmissive portion 3032 of the mask 3000 may be configured to be opaque to prevent the transmission of light. As used herein the term "opaque" is intended to be a broad term meaning capable of preventing the transmission of radiant energy, e.g., light energy, and also covers structures and arrangements that absorb or otherwise block all or less than all or at least a substantial portion of the light. In one embodiment, at least a portion of the body 3004 is configured to be opaque to more than 99 percent of the light incident thereon.

As discussed above, the non-transmissive portion 3032 may be configured to prevent transmission of light without absorbing the incident light. For example, the mask 3000 could be made reflective or could be made to interact with the light in a more complex manner, as discussed in U.S. Pat. No. 6,554,424, issued Apr. 29, 2003, which is hereby incorporated by reference herein in its entirety.

As discussed above, the mask 3000 also has a nutrient transport structure that in some embodiments comprises the plurality of holes 3020. The presence of the plurality of holes 3020 (or other transport structure) may affect the transmission of light through the non-transmissive portion 3032 by potentially allowing more light to pass through the mask 3000. In one embodiment, the non-transmissive portion 3032 is configured to absorb about 99 percent or more of the incident light from passing through the mask 3000 without holes 3020 being present. The presence of the plurality of holes 3020 allows more light to pass through the non-transmissive portion 3032 such that only about 92 percent of the light incident on the non-transmissive portion 3032 is prevented from passing through the non-transmissive portion 3032. The holes 3020 may reduce the benefit of the aperture 3028 on the depth of focus of the eye by allowing more light to pass through the non-transmissive portion to the retina.

Reduction in the depth of focus benefit of the aperture 3028 due to the holes 3020 is balanced by the nutrient transmission benefits of the holes 3020. In one embodiment, the transport structure 3016 (e.g., the holes 3020) is capable of substantially maintaining natural nutrient flow from a first corneal layer (i.e., one that is adjacent to the anterior surface 3008 of the mask 3000) to the second corneal layer (i.e., one that is adjacent to the posterior surface 3012 of the mask 3000). The plurality of holes 3020 are configured to enable nutrients to pass through the mask 3000 between the anterior surface 3008 and the posterior surface 3012. As discussed above, the holes 3020 of the mask 3000 shown in FIG. 60 may be located anywhere on the mask 3000. Other mask embodiments described hereinbelow locate substantially all of the nutrient transport structure in one or more regions of a mask.

The holes 3020 of FIG. 60 extends at least partially between the anterior surface 3008 and the posterior surface 3012 of the mask 3000. In one embodiment, each of the holes 3020 includes a hole entrance 3060 and a hole exit 3064. The hole entrance 3060 is located adjacent to the anterior surface 3008 of the mask 3000. The hole exit 3064 is located adjacent to the posterior surface 3012 of the mask 3000. In one embodiment, each of the holes 3020 extends the entire distance between the anterior surface 3008 and the posterior surface 3012 of the mask 3000.

The transport structure 3016 is configured to maintain the transport of one or more nutrients across the mask 3000. The transport structure 3016 of the mask 3000 provides sufficient flow of one or more nutrients across the mask 3000 to prevent depletion of nutrients at least at one of the first and second corneal layers (e.g., the layers 1410 and 1430). One nutrient of particular importance to the viability of the adjacent corneal layers is glucose. The transport structure 3016 of the mask 3000 provides sufficient flow of glucose across the mask 3000 between the first and second corneal layers to prevent glucose depletion that would harm the adjacent corneal tissue. Thus, the mask 3000 is capable of substantially maintaining nutrient flow (e.g., glucose flow) between adjacent corneal layers. In one embodiment, the nutrient transport structure 3016 is configured to prevent depletion of more than about 4 percent of glucose (or other biological substance) in adjacent tissue of at least one of the first corneal layer and the second corneal layer.

The holes 3020 may be configured to maintain the transport of nutrients across the mask 3000. In one embodiment, the holes 3020 are formed with a diameter of about 0.015 mm or more. In another embodiment, the holes have a diameter of about 0.020 mm. In another embodiment, the holes have a diameter of about 0.025 mm. In another embodiment, the holes 3020 have a diameter in the range of about 0.020 mm to about 0.029 mm. The number of holes in the plurality of holes 3020 is selected such that the sum of the surface areas of the hole entrances 3060 of all the holes 3000 comprises about 5 percent or more of surface area of the anterior surface 3008 of the mask 3000. In another embodiment, the number of holes 3020 is selected such that the sum of the surface areas of the hole exits 3064 of all the holes 3020 comprises about 5 percent or more of surface area of the posterior surface 3012 of the mask 3000. In another embodiment, the number of holes 3020 is selected such that the sum of the surface areas of the hole exits 3064 of all the holes 3020 comprises about 5 percent or more of surface area of the posterior surface 3012 of the mask 3012 and the sum of the surface areas of the hole entrances 3060 of all the holes 3020 comprises about 5 percent or more of surface area of the anterior surface 3008 of the mask 3000.

Each of the holes 3020 may have a relatively constant cross-sectional area. In one embodiment, the cross-sectional shape of each of the holes 3020 is substantially circular. Each of the holes 3020 may comprise a cylinder extending between the anterior surface 3008 and the posterior surface 3012.

The relative position of the holes 3020 is of interest in some embodiments. As discussed above, the holes 3020 of the mask 3000 are hex-packed, e.g., arranged in a hex pattern. In particular, in this embodiment, each of the holes 3020 is separated from the adjacent holes 3020 by a substantially constant distance, sometimes referred to herein as a hole pitch 3072. In one embodiment, the hole pitch 3072 is about 0.062 mm.

The embodiment of FIG. 60 advantageously enables nutrients to flow from the first corneal layer to the second corneal layer. The inventors have discovered that negative visual effects can arise due to the presence of the transport structure 3016. For example, in some cases, a hex packed arrangement of the holes 3020 can generate diffraction patterns visible to the patient. For example, patients might observe a plurality of spots, e.g., six spots, surrounding a central light with holes 3020 having a hex patterned.

The inventors have discovered a variety of techniques that produce advantageous arrangements of a transport structure such that diffraction patterns and other deleterious visual effects do not substantially inhibit other visual benefits of a mask. In one embodiment, where diffraction effects would be observable, the nutrient transport structure is arranged to spread the diffracted light out uniformly across the image to eliminate observable spots. In another embodiment, the nutrient transport structure employs a pattern that substantially eliminates diffraction patterns or pushes the patterns to the periphery of the image.

Figure 62A:
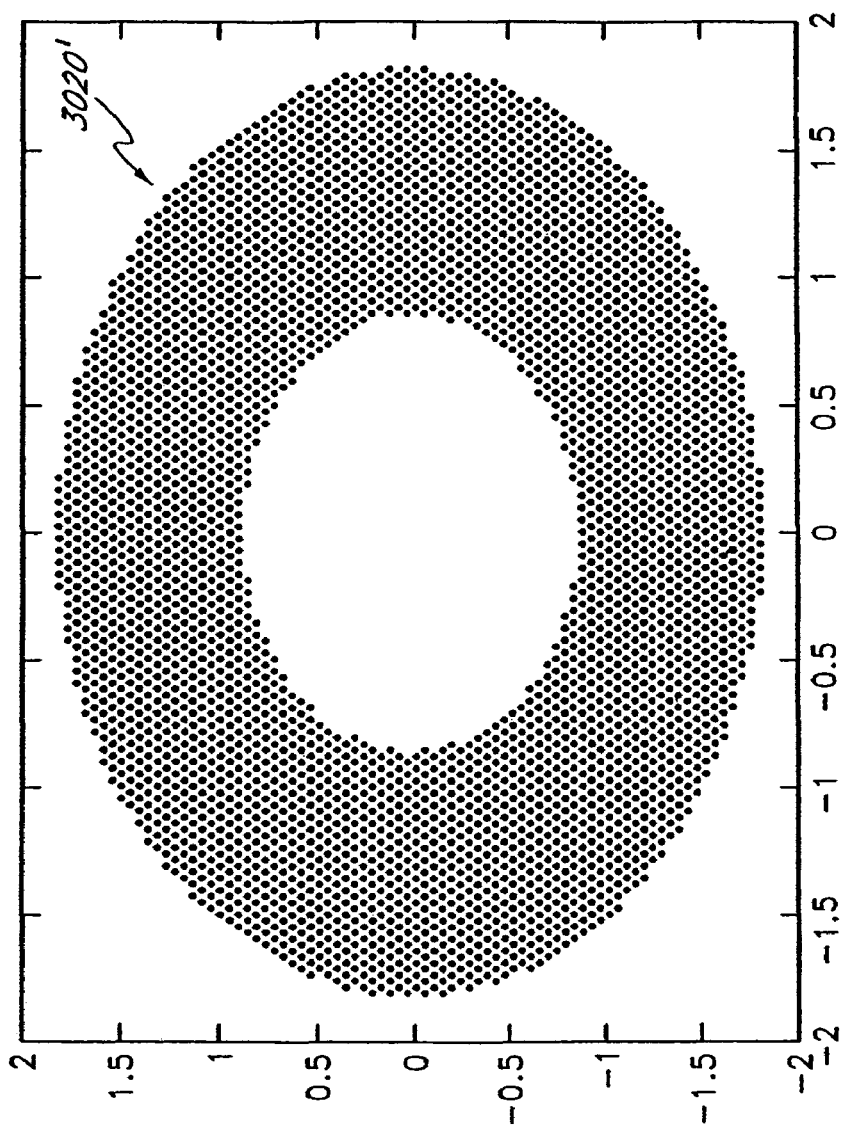
FIG. 62A is a graphical representation of one arrangement of holes of a plurality of holes that may be formed on the mask of FIG. 60.
Figure 62B:
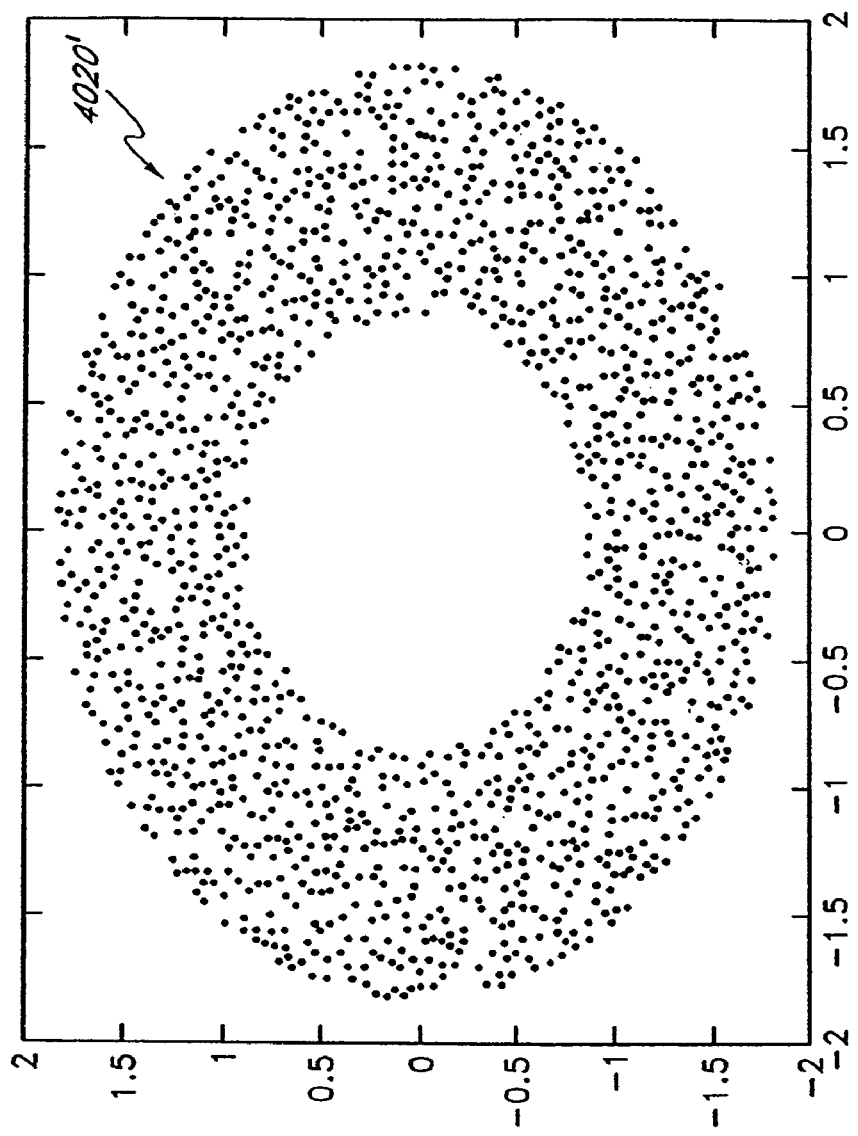
FIG. 62B is a graphical representation of another arrangement of holes holes that may be formed on the mask of FIG. 60.
Figure 62C:
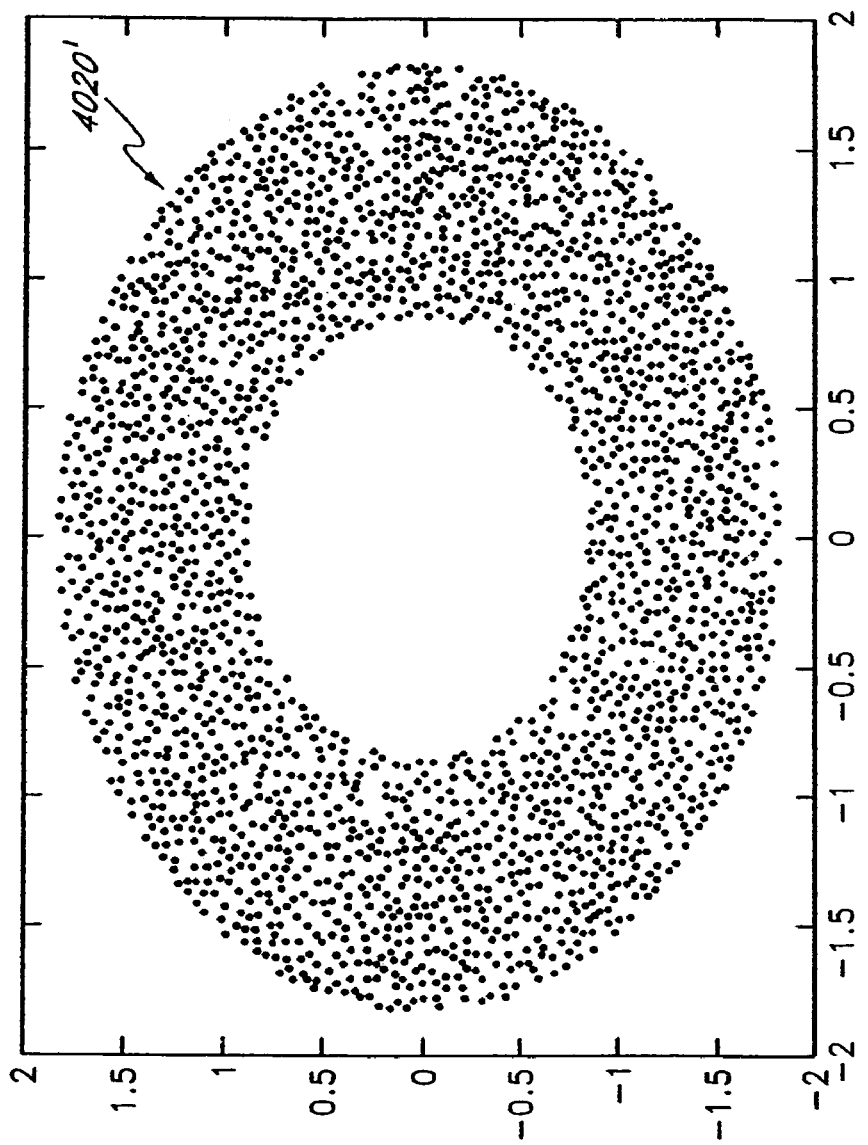
FIG. 62C is a graphical representation of another arrangement of holes of a plurality of holes that may be formed on the mask of FIG. 60.

FIG. 62B-62C show two embodiments of patterns of holes 4020 that may be applied to a mask that is otherwise substantially similar to the mask 3000. The holes 4020 of the hole patterns of FIGS. 62A-62B are spaced from each other by a random hole spacing or hole pitch. In other embodiments discussed below, holes are spaced from each other by a non-uniform amount, e.g., not a random amount. In one embodiment, the holes 4020 have a substantially uniform shape (cylindrical shafts having a substantially constant cross-sectional area). FIG. 62C illustrates a plurality of holes 4020 separated by a random spacing, wherein the density of the holes is greater than that of FIG. 62B. Generally, the higher the percentage of the mask body that has holes the more the mask will transport nutrients in a manner similar to the native tissue. One way to provide a higher percentage of hole area is to increase the density of the holes. Increase hole density can also permit smaller holes to achieve the same nutrient transport as is achieved by less dense, larger holes.

Figure 63A:
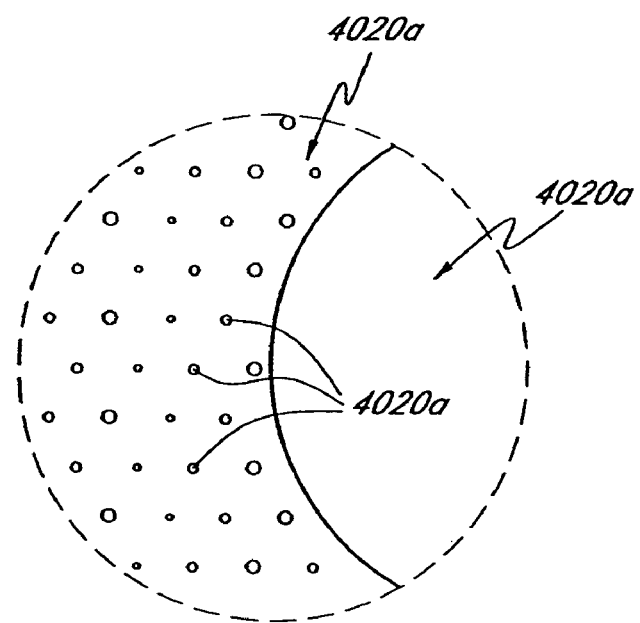
FIG. 63A is an enlarged view similar to that of FIG. 60A showing a variation of a mask having non-uniform size.

FIG. 63A shows a portion of another mask 4000a that is substantially similar to the mask 3000, except as set forth below. The mask 4000a has a plurality of holes 4020a. A substantial number of the holes 4020a have a non-uniform size. The holes 4020a may be uniform in cross-sectional shape. The cross-sectional shape of the holes 4020a is substantially circular in one embodiment. The holes 4020a may be circular in shape and have the same diameter from a hole entrance to a hole exit, but are otherwise non-uniform in at least one aspect, e.g., in size. It may be preferable to vary the size of a substantial number of the holes by a random amount. In another embodiment, the holes 4020a are non-uniform (e.g., random) in size and are separated by a non-uniform (e.g., a random) spacing.

Figure 63B:
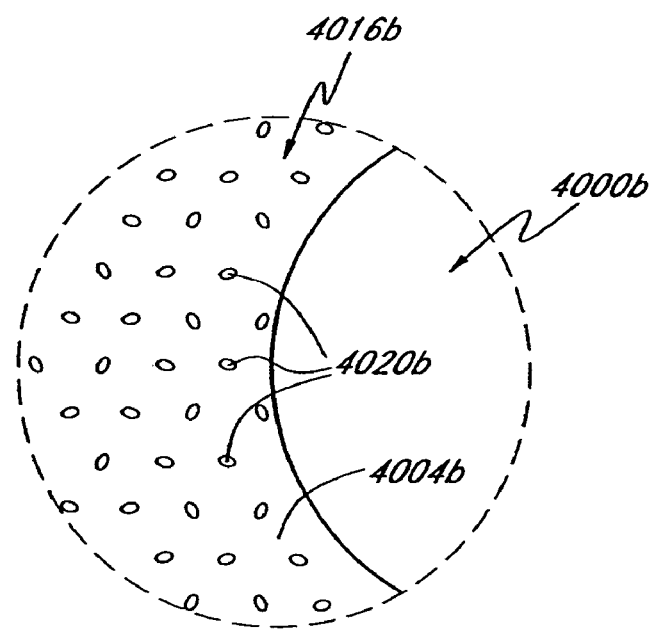
FIG. 63B is an enlarged view similar to that of FIG. 60A showing a variation of a mask having a non-uniform facet orientation.

FIG. 63B illustrates another embodiment of a mask 4000b that is substantially similar to the mask 3000, except as set forth below. The mask 4000b includes a body 4004b. The mask 4000b has a transport structure 4016b that includes a plurality of holes 4020b with a non-uniform facet orientation. In particular, each of the holes 4020b has a hole entrance 4060b that may be located at an anterior surface 4008b of the mask 4000b. A facet 4062b of the hole entrance 4060b is defined by a portion of the body 4004b of the mask 4000b surrounding the hole entrance 4060b. The facet 4062b is the shape of the hole entrance 4060b at the anterior surface 4008b. In one embodiment, most or all the facets 4062b have an elongate shape, e.g., an oblong shape, with a long axis and a short axis that is perpendicular to the long axis. The facets 4062b may be substantially uniform in shape. In one embodiment, the orientation of facets 4062b is not uniform. For example, a substantial number of the facets 4062 may have a non-uniform orientation. In one arrangement, a substantial number of the facets 4062 have a random orientation. In some embodiments, the facets 4062b are non-uniform (e.g., random) in shape and are non-uniform (e.g., random) in orientation.

Other embodiments may be provided that vary at least one aspect, including one or more of the foregoing aspects, of a plurality of holes to reduce the tendency of the holes to produce visible diffraction patterns or patterns that otherwise reduce the vision improvement that may be provided by a mask with an aperture, such as any of those described above. For example, in one embodiment, the hole size, shape, and orientation of at least a substantial number of the holes may be varied randomly or may be otherwise non-uniform uniform.

Figure 64:
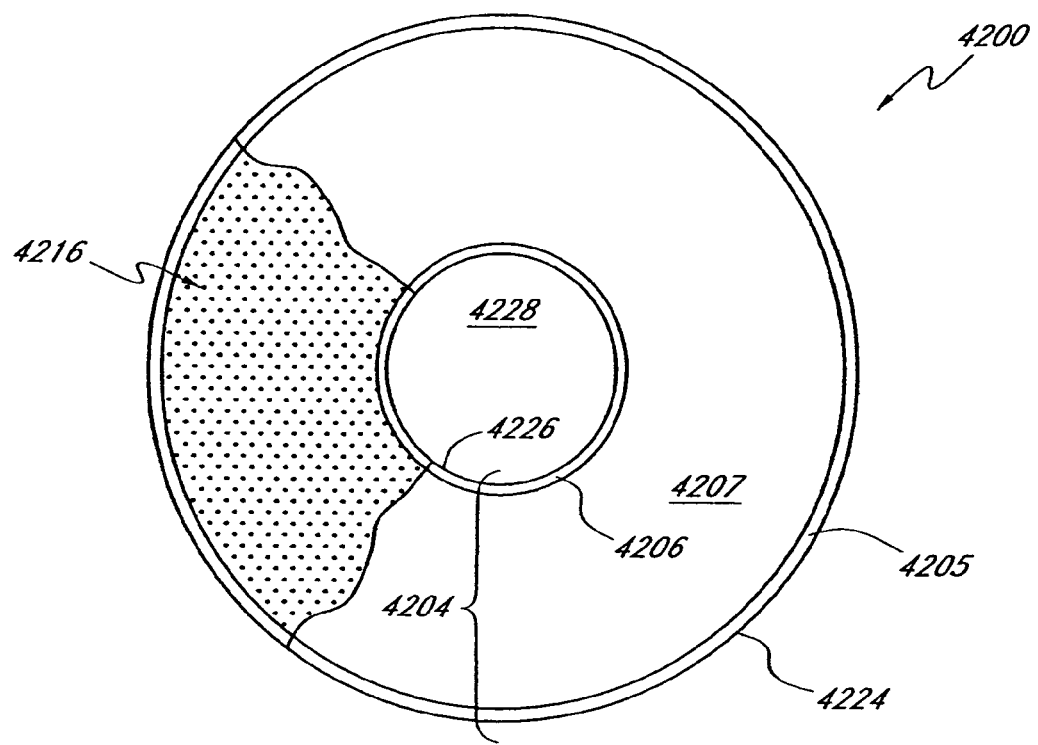
FIG. 64 is a top view of another embodiment of a mask having a hole region and a peripheral region.

FIG. 64 shows another embodiment of a mask 4200 that is substantially similar to any of the masks hereinbefore described, except as set forth below. The mask 4200 includes a body 4204. The body 4204 has an outer peripheral region 4205, an inner peripheral region 4206, and a hole region 4207. The hole region 4207 is located between the outer peripheral region 4205 and the outer peripheral region 4206. The body 4204 may also include an aperture region, where the aperture (discussed below) is not a through hole. The mask 4200 also includes a nutrient transport structure 4216. In one embodiment, the nutrient transport structure includes a plurality of holes 4220. At least a substantial portion of the holes 4220 (e.g., all of the holes) are located in the hole region 4207. As above, only a portion of the nutrient structure 4216 is shown for simplicity. But it should be understood that the hole 4220 may be located through the hole region 4207.

The outer peripheral region 4205 may extend from an outer periphery 4224 of the mask 4200 to a selected outer circumference 4226 of the mask 4200. The selected outer circumference 4225 of the mask 4200 is located a selected radial distance from the outer periphery 4224 of the mask 4200. In one embodiment, the selected outer circumference 4225 of the mask 4200 is located about 0.05 mm from the outer periphery 4224 of the mask 4200.

The inner peripheral region 4206 may extend from an inner location, e.g., an inner periphery 4226 adjacent an aperture 4228 of the mask 4200 to a selected inner circumference 4227 of the mask 4200. The selected inner circumference 4227 of the mask 4200 is located a selected radial distance from the inner periphery 4226 of the mask 4200. In one embodiment, the selected inner circumference 4227 of the mask 4200 is located about 0.05 mm from the inner periphery 4226.

The mask 4200 may be the product of a process that involves random selection of a plurality of locations and formation of holes on the mask 4200 corresponding to the locations. As discussed further below, the method can also involve determining whether the selected locations satisfy one or more criteria. For example, one criterion prohibits all, at least a majority, or at least a substantial portion of the holes from being formed at locations that correspond to the inner or outer peripheral regions 4205, 4206. Another criterion prohibits all, at least a majority, or at least a substantial portion of the holes 4220 from being formed too close to each other. For example, such a criterion could be used to assure that a wall thickness, e.g., the shortest distance between adjacent holes, is not less than a predetermined amount. In one embodiment, the wall thickness is prevented from being less than about 20 microns.

In a variation of the embodiment of FIG. 64, the outer peripheral region 4205 is eliminated and the hole region 4207 extends from the inner peripheral region 4206 to an outer periphery 4224. In another variation of the embodiment of FIG. 64, the inner peripheral region 4206 is eliminated and the hole region 4207 extends from the outer peripheral region 4205 to an inner periphery 4226.

Figure 61B:
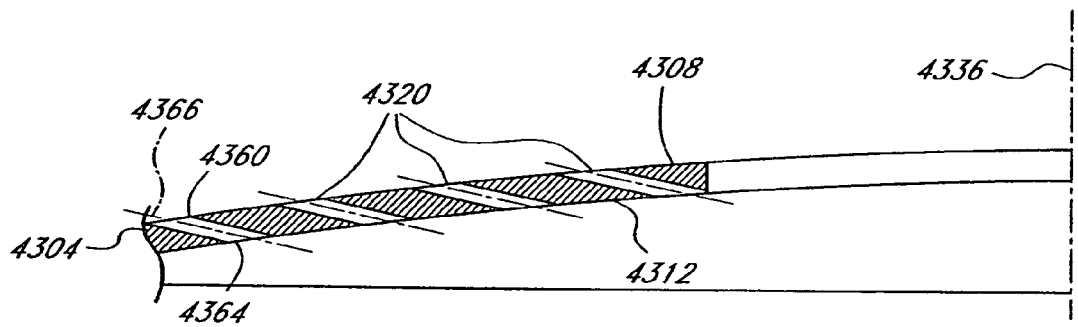
FIG. 61B is a cross-sectional view similar to FIG. 61A of another embodiment of a mask.

FIG. 61B shows a mask 4300 that is similar to the mask 3000 except as set forth below. The mask 4300 includes a body 4304 that has an anterior surface 4308 and a posterior surface 4312. The mask 4300 also includes a nutrient transport structure 4316 that, in one embodiment, includes a plurality of holes 4320. The holes 4320 are formed in the body 4304 so that nutrient transport is provided but transmission of radiant energy (e.g., light) to the retinal locations adjacent the fovea through the holes 4304 is substantially prevented. In particular, the holes 4304 are formed such that when the eye with which the mask 4300 is coupled is directed at an object to be viewed, light conveying the image of that object that enters the holes 4320 cannot exit the holes along a path ending near the fovea.

In one embodiment, each of the holes 4320 has a hole entrance 4360 and a hole exit 4364. Each of the holes 4320 extends along a transport axis 4366. The transport axis 4366 is formed to substantially prevent propagation of light from the anterior surface 4308 to the posterior surface 4312 through the holes 4320. In one embodiment, at least a substantial number of the holes 4320 have a size to the transport axis 4366 that is less than a thickness of the mask 4300. In another embodiment, at least a substantial number of the holes 4320 have a longest dimension of a perimeter at least at one of the anterior or posterior surfaces 4308, 4312 (e.g., a facet) that is less than a thickness of the mask 4300. In some embodiments, the transport axis 4366 is formed at an angle with respect to a mask axis 4336 that substantially prevents propagation of light from the anterior surface 4308 to the posterior surface 4312 through the hole 4320. In another embodiment, the transport axis 4366 of one or more holes 4320 is formed at an angle with respect to the mask axis 4336 that is large enough to prevent the projection of most of the hole entrance 4360 from overlapping the hole exit 4364.

In one embodiment, the hole 4320 is circular in cross-section and has a diameter between about 0.5 micron and about 8 micron and the transport axis 4366 is between 5 and 85 degrees. The length of each of the holes 4320 (e.g., the distance between the anterior surface 4308 and the posterior surface 4312) is between about 8 and about 92 micron. In another embodiment, the diameter of the holes 4320 is about 5 micron and the transport angle is about 40 degrees or more. As the length of the holes 4320 increases it may be desirable to include additional holes 4320. In some cases, additional holes 4320 counteract the tendency of longer holes to reduce the amount of nutrient flow through the mask 4300.

Figure 61C:
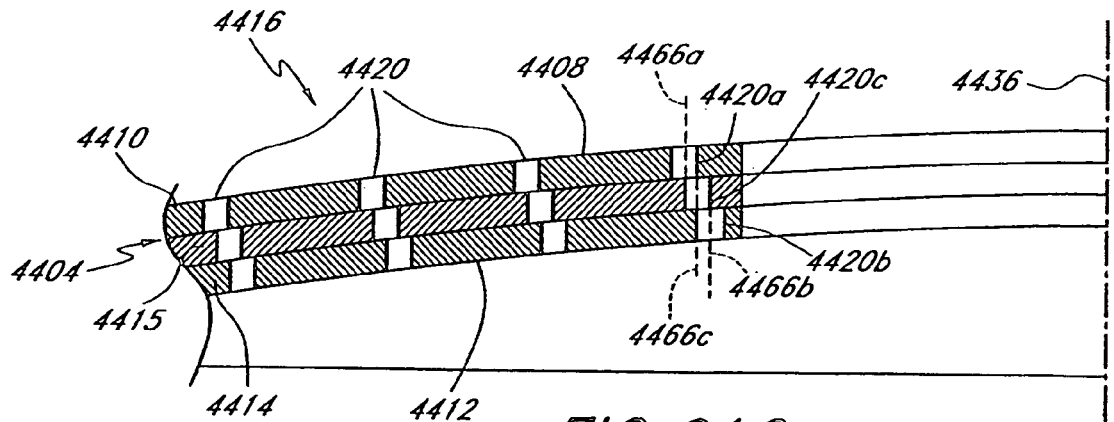
FIG. 61C is a cross-sectional view similar to FIG. 61C of another embodiment of a mask.

FIG. 61C shows another embodiment of a mask 4400 similar to the mask 3000, except as set forth below. The mask 4400 includes a body 4404 that has an anterior surface 4408, a first mask layer 4410 adjacent the anterior surface 44008, a posterior surface 4412, a second mask layer 4414 adjacent the posterior surface 4412, and a third layer 4415 located between the first mask layer 4410 and the second mask layer 4414. The mask 4400 also includes a nutrient transport structure 4416 that, in one embodiment, includes a plurality of holes 4420. The holes 4420 are formed in the body 4404 so that nutrient are transported across the mask, as discussed above, but transmission of radiant energy (e.g., light) to retinal locations adjacent the fovea through the holes 4404 is substantially prevented. In particular, the holes 4404 are formed such that when the eye with which the mask 4400 is coupled is directed at an object to be viewed, light conveying the image of that object that enters the holes 4420 cannot exit the holes along a path ending near the fovea.

In one embodiment, at least one of the holes 4420 extends along a non-linear path that substantially prevents propagation of light from the anterior surface to the posterior surface through the at least one hole. In one embodiment, the mask 4400 includes a first hole portion 4420a that extends along a first transport axis 4466a, the second mask layer 4414 includes a second hole portion 4420b extending along a second transport axis 4466b, and the third mask layer 4415 includes a third hole portion 4420c extending along a third transport axis 4466c. The first, second, and third transport axes 4466a, 4466b, 4466c preferably are not collinear. In one embodiment, the first and second transport axes 4466a, 4466b are parallel but are off-set by a first selected amount. In one embodiment, the second and third transport axes 4466b, 4466c are parallel but are off-set by a second selected amount. In the illustrated embodiment, each of the transport axes 44466a, 4466b, 4466c are off-set by one-half of the width of the hole portions 4420a, 4420b, 4420c. Thus, the inner-most edge of the hole portion 4420a is spaced from the axis 4336 by a distance that is equal to or greater than the distance of the outer-most edge of the hole portion 4420b from the axis 4336. This spacing substantially prevents light from passing through the holes 4420 from the anterior surface 4408 to the posterior surface 4412.

In one embodiment, the first and second amounts are selected to substantially prevent the transmission of light therethrough. The first and second amounts of off-set may be achieved in any suitable fashion. One technique for forming the hole portions 4420a, 4420b, 4420c with the desired off-set is to provide a layered structure. As discussed above, the mask 4400 may include the first layer 4410, the second layer 4414, and the third layer 4415. FIG. 61C shows that the mask 4400 can be formed with three layers. In another embodiment, the mask 4400 is formed of more than three layers. Providing more layers may advantageously further decrease the tendency of light to be transmitted through the holes 4420 onto the retina. This has the benefit of reducing the likelihood that a patient will observe or otherwise perceive a patter that will detract from the vision benefits of the mask 4400. A further benefit is that less light will pass through the mask 4400, thereby enhancing the depth of focus increase due to the pin-hole sized aperture formed therein.

In any of the foregoing mask embodiments, the body of the mask may be formed of a material selected to provide adequate nutrient transport and to substantially prevent negative optic effects, such as diffraction, as discussed above. In various embodiments, the masks are formed of an open cell foam material. In another embodiment, the masks are formed of an expanded solid material.

As discussed above in connection with FIGS. 62B and 62C, various random patterns of holes may advantageously be provided for nutrient transport. In some embodiment, it may be sufficient to provide regular patterns that are non-uniform in some aspect. Non-uniform aspects to the holes may be provided by any suitable technique.

In a first step of one technique, a plurality of locations 4020' is generated. The locations 4020' are a series of coordinates that may comprise a non-uniform pattern or a regular pattern. The locations 4020' may be randomly generated or may be related by a mathematical relationship (e.g., separated by a fixed spacing or by an amount that can be mathematically defined). In one embodiment, the locations are selected to be separated by a constant pitch or spacing and may be hex packed.

In a second step, a subset of the locations among the plurality of locations 4020' is modified to maintain a performance characteristic of the mask. The performance characteristic may be any performance characteristic of the mask. For example, the performance characteristic may relate to the structural integrity of the mask. Where the plurality of locations 4020' is selected at random, the process of modifying the subset of locations may make the resulting pattern of holes in the mask a "pseudo-random" pattern.

Where a hex packed pattern of locations (such as the locations 3020' of FIG. 62A) is selected in the first step, the subset of locations may be moved with respect to their initial positions as selected in the first step. In one embodiment, each of the locations in the subset of locations is moved by an amount equal to a fraction of the hole spacing. For example, each of the locations in the subset of locations may be moved by an amount equal to one-quarter of the hole spacing. Where the subset of locations is moved by a constant amount, the locations that are moved preferably are randomly or pseudo-randomly selected. In another embodiment, the subset of location is moved by a random or a pseudo-random amount.

In one technique, an outer peripheral region is defined that extends between the outer periphery of the mask and a selected radial distance of about 0.05 mm from the outer periphery. In another embodiment, an inner peripheral region is defined that extends between an aperture of the mask and a selected radial distance of about 0.05 mm from the aperture. In another embodiment, an outer peripheral region is defined that extends between the outer periphery of the mask and a selected radial distance and an inner peripheral region is defined that extends between the aperture of the mask and a selected radial distance from the aperture. In one technique, the subset of location is modified by excluding those locations that would correspond to holes formed in the inner peripheral region or the outer peripheral region. By excluding locations in at least one of the outer peripheral region and the inner peripheral region, the strength of the mask in these regions is increased. Several benefits are provided by stronger inner and outer peripheral regions. For example, the mask may be easier to handle during manufacturing or when being applied to a patient without causing damage to the mask.

In another embodiment, the subset of locations is modified by comparing the separation of the holes with minimum and or maximum limits. For example, it may be desirable to assure that no two locations are closer than a minimum value. In some embodiments this is important to assure that the wall thickness, which corresponds to the separation between adjacent holes, is no less than a minimum amount. As discussed above, the minimum value of separation is about 20 microns in one embodiment, thereby providing a wall thickness of no less than about 20 microns.

In another embodiment, the subset of locations is modified and/or the pattern of location is augmented to maintain an optical characteristic of the mask. For example, the optical characteristic may be opacity and the subset of locations may be modified to maintain the opacity of a non-transmissive portion of a mask. In another embodiment, the subset of locations may be modified by equalizing the density of holes in a first region of the body compared with the density of holes in a second region of the body. For example, the locations corresponding to the first and second regions of the non-transmissve portion of the mask may be identified. In one embodiment, the first region and the second region are arcuate regions (e.g., wedges) of substantially equal area. A first areal density of locations (e.g., locations per square inch) is calculated for the locations corresponding to the first region and a second areal density of locations is calculated for the locations corresponding to the second region. In one embodiment, at least one location is added to either the first or the second region based on the comparison of the first and second areal densities. In another embodiment, at least one location is removed based on the comparison of the first and second areal densities.

The subset of locations may be modified to maintain nutrient transport of the mask. In one embodiment, the subset of location is modified to maintain glucose transport.

In a third step, a hole is formed in a body of a mask at locations corresponding to the pattern of locations as modified, augmented, or modified and augmented. The holes are configured to substantially maintain natural nutrient flow from the first layer to the second layer without producing visible diffraction patterns.

VI. Further Methods of Treating a Patient

As discussed above in, various techniques are particularly suited for treating a patient by applying masks such as those disclosed herein to an eye. For example, in some embodiments, the surgical system 2000 of FIG. 55 employs a marking module 2024 that provides a visual cue in the form of a projected image for a surgeon during a procedure for applying a mask. In addition, some techniques for treating a patient involve positioning an implant with the aid of a marked reference point. These methods are illustrated by FIGS. 65-66B.

In one method, a patient is treated by placing an implant 5000 in a cornea 5004. A corneal flap 5008 is lifted to expose a surface in the cornea 5004 (e.g., an intracorneal surface). Any suitable tool or technique may be used to lift the corneal flap 5008 to expose a surface in the cornea 5004. For example, a blade (e.g., a microkeratome), a laser or an electrosurgical tool could be used to form a corneal flap. A reference point 5012 on the cornea 5004 is identified. The reference point 5012 thereafter is marked in one technique, as discussed further below. The implant 5000 is positioned on the intracorneal surface. In one embodiment, the flap 5008 is then closed to cover at least a portion of the implant 5000.

The surface of the cornea that is exposed is a stromal surface in one technique. The stromal surface may be on the corneal flap 5008 or on an exposed surface from which the corneal flap 5008 is removed.

The reference point 5012 may be identified in any suitable manner. For example, the alignment devices and methods described above may be used to identify the reference point 5012. In one technique, identifying the reference point 5012 involves illuminating a light spot (e.g., a spot of light formed by all or a discrete portion of radiant energy corresponding to visible light, e.g., red light). As discussed above, the identifying of a reference point may further include placing liquid (e.g., a fluorescein dye or other dye) on the intracorneal surface. Preferably, identifying the reference point 5012 involves alignment using any of the techniques described herein.

As discussed above, various techniques may be used to mark an identified reference point. In one technique the reference point is marked by applying a dye to the cornea or otherwise spreading a material with known reflective properties onto the cornea. As discussed above, the dye may be a substance that interacts with radiant energy to increase the visibility of a marking target or other visual cue. The reference point may be marked by a dye with any suitable tool. The tool is configured so that it bites into a corneal layer, e.g., an anterior layer of the epithelium, and delivers a thin ink line into the corneal layer in one embodiment. The tool may be made sharp to bite into the epithelium. In one application, the tool is configured to deliver the dye as discussed above upon being lightly pressed against the eye. This arrangement is advantageous in that it does not form a larger impression in the eye. In another technique, the reference point may be marked by making an impression (e.g., a physical depression) on a surface of the cornea with or without additional delivery of a dye. In another technique, the reference point may be marked by illuminating a light or other source of radiant energy, e.g., a marking target illuminator and projecting that light onto the cornea (e.g., by projecting a marking target).

Any of the foregoing techniques for marking a reference point may be combined with techniques that make a mark that indicates the location of an axis of the eye, e.g., the visual axis or line-of-sight of the eye. In one technique, a mark indicates the approximate intersection of the visual axis and a surface of the cornea. In another technique, a mark is made approximately radially symmetrically disposed about the intersection of the visual axis and a surface of the cornea.

As discussed above, some techniques involve making a mark on an intracorneal surface. The mark may be made by any suitable technique. In one technique a mark is made by pressing an implement against the intracorneal surface. The implement may form a depression that has a size and shape that facilitate placement of a mask. For example, in one form the implement is configured to form a circular ring (e.g., a thin line of dye, or a physical depression, or both) with a diameter that is slightly larger than the outer diameter of a mask to be implanted. The circular ring can be formed to have a diameter between about 4 mm and about 5 mm. The intracorneal surface is on the corneal flap 5008 in one technique. In another technique, the intracorneal surface is on an exposed surface of the cornea from which the flap was removed. This exposed surface is sometimes referred to as a tissue bed.

In another technique, the corneal flap 5008 is lifted and thereafter is laid on an adjacent surface 5016 of the cornea 5004. In another technique, the corneal flap 5008 is laid on a removable support 5020, such as a sponge. In one technique, the removable support has a surface 5024 that is configured to maintain the native curvature of the corneal flap 5008.

FIG. 65 shows that the marked reference point 5012 is helpful in positioning an implant on an intracorneal surface. In particular, the marked reference point 5012 enables the implant to be positioned with respect to the visual axis of the eye. In the illustrated embodiment, the implant 5000 is positioned so that a centerline of the implant, indicated as $M_{CL}$, extends through the marked reference point 5012.

FIG. 65A illustrates another technique wherein a reference 5012' is a ring or other two dimensional mark. In such a case, the implant 5000 may be placed so that an outer edge of the implant and the ring correspond, e.g., such that the ring and the implant 5000 share the same or substantially the same center. Preferably, the ring and the implant 5000 are aligned so that the centerline of the implant $M_{CL}$ is on the line of sight of the eye, as discussed above. The ring is shown in dashed lines because in the illustrated technique, it is formed on the anterior surface of the corneal flap 5008.

In one technique, the corneal flap 5008 is closed by returning the corneal flap 5008 to the cornea 5004 with the implant 5000 on the corneal flap 5008. In another technique, the corneal flap 5008 is closed by returning the corneal flap 5008 to the cornea 5004 over the implant 5000, which previously was placed on the tissue bed (the exposed intracorneal surface).

When the intracorneal surface is a stromal surface, the implant 5000 is placed on the stromal surface. At least a portion of the implant 5000 is covered. In some techniques, the implant 5000 is covered by returning a flap with the implant 5000 thereon to the cornea 5004 to cover the stromal surface. In one technique, the stromal surface is exposed by lifting an epithelial layer to expose stroma. In another technique, the stromal surface is exposed by removing an epithelial layer to expose stroma. In some techniques, an additional step of replacing the epithelial layer to at least partially cover the implant 5000 is performed.

After the flap 5008 is closed to cover at least a portion of the implant 5000, the implant 5000 may be repositioned to some extent in some applications. In one technique, pressure is applied to the implant 5000 to move the implant into alignment with the reference point 5012. The pressure may be applied to the anterior surface of the cornea 5004 proximate an edge of the implant 5000 (e.g., directly above, above and outside a projection of the outer periphery of the implant 5000, or above and inside a projection of the outer periphery of the implant 5000). This may cause the implant to move slightly away from the edge proximate which pressure is applied. In another technique, pressure is applied directly to the implant. The implant 5000 may be repositioned in this manner if the reference point 5012 was marked on the flap 5008 or if the reference point 5012 was marked on the tissue bed.

FIG. 66 shows that a patient may also be treated by a method that positions an implant 5100 in a cornea 5104, e.g., in a corneal pocket 5108. Any suitable tool or technique may be used to create or form the corneal pocket 5108. For example, a blade (e.g., a microkeratome), a laser, or an electrosurgical tool could be used to create or form a pocket in the cornea 5104. A reference point 5112 is identified on the cornea 5104. The reference point may be identified by any suitable technique, such as those discussed herein. The reference point 5112 is marked by any suitable technique, such as those discussed herein. The corneal pocket 5108 is created to expose an intracorneal surface 5116. The corneal pocket 5108 may be created at any suitable depth, for example at a depth within a range of from about 50 microns to about 300 microns from the anterior surface of the cornea 5104. The implant 5100 is positioned on the intracorneal surface 5116. The marked reference point 5112 is helpful in positioning the implant 5100 on the intracorneal surface 5116. The marked reference point 5112 enables the implant 5100 to be positioned with respect to the visual axis of the eye, as discussed above. In the illustrated embodiment, the implant 5100 is positioned so that a centerline $M_{CL}$ of the implant 5100 extends through or adjacent to the marked reference point 5112.

FIG. 66A illustrates another technique wherein a reference 5112' is a ring or other two dimensional mark. In such case, the implant 5100 may be placed so that an outer edge of the implant and the ring correspond, e.g., such that the ring and the implant 5100 share the same or substantially the same center. Preferably, the ring and the implant 5100 are aligned so that the centerline of the implant $M_{CL}$ is on the line of sight of the eye, as discussed above. The ring is shown in solid lines because in the illustrated embodiment, it is formed on the anterior surface of the cornea 5104 above the pocket 5108.

After the implant 5100 is positioned in the pocket 5108, the implant 5100 may be repositioned to some extent in some applications. In one technique, pressure is applied to the implant 5100 to move the implant into alignment with the reference point 5112. The pressure may be applied to the anterior surface of the cornea 5104 proximate an edge of the implant 5100 (e.g., directly above, above and outside a projection of the outer periphery of the implant 5100, or above and inside a projection of the outer periphery of the implant 5100). This may cause the implant 5100 to move slightly away from the edge at which pressure is applied. In another technique, pressure is applied directly to the implant 5100.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. An apparatus for aligning a mask with a visual axis of an eye of a patient, the apparatus comprising:
   a first target positioned on an instrument axis at a first distance relative to a first location;
   a second target positioned on the instrument axis at a second distance relative to the first location; and
   a marker configured to indicate the location of the instrument axis;
   wherein the mask comprises an aperture having a mask axis that can be positioned substantially collinear with the instrument axis, further wherein the mask comprises an annulus configured to be substantially opaque to visible light and to extend between the aperture and an outer periphery of the mask, the annulus having an inner peripheral region between a central region and the aperture and an outer peripheral region between the central region and the outer periphery of the mask, the inner peripheral, central and outer peripheral regions each having a nutrient transport structure for conveying nutrients between anterior and posterior surfaces of the mask, the nutrient transport structure providing an amount of open area per unit area in the central region that is greater than an amount of open area per unit area in at least one of the outer peripheral region and the inner peripheral region.

2. The apparatus of claim 1, wherein the marker comprises an image capture device and a display device, the display device being configured to reproduce an image of the eye taken by the image capture device.

3. The apparatus of claim 2, wherein the patient actuates a trigger when the patient's eye is aligned with the instrument axis.

4. The apparatus of claim 3, wherein the image capture device further compares a real-time position of the patient's eye with the image of the eye captured when the patient actuates the trigger.

5. The apparatus of claim 2, wherein the apparatus is configured to track movements of the patient's eye during a procedure.

6. The apparatus of claim 5, wherein the apparatus comprises a display device and is configured to display a reference and to move the reference in a manner corresponding to movements of the eye such that a real-time position of the visual axis may be tracked.

7. The apparatus of claim 6, wherein the reference comprises a ring that can be overlaid upon on image of the patient's eye such that the position of the ring and the position of the eye may be simultaneously visible to a user.

8. The apparatus of claim 1, wherein the marker comprises a light source and a marking target, the light source configured to project an image of the marking target onto the eye.

9. The apparatus of claim 1, further comprising a fixture for locating the eye at the first location.

10. The apparatus of claim 1, further comprising a beamsplitter positioned on the instrument axis to intercept light from the marker and direct the light toward a fixture for positioning the patient relative to the apparatus.

11. The apparatus of claim 1, further comprising a mirror configured to be moved into position on the instrument axis to intercept light from the marker and direct the light toward a fixture for positioning the patient relative to the apparatus.

12. The apparatus of claim 1, further comprising a lens optically coupled with the first and second targets, the second distance being equal to the focal length of the lens, whereby the second target is imaged at approximately infinity.

13. The apparatus of claim 1, wherein the first distance is less than the second distance.

14. The apparatus of claim 1, wherein the amount of open area per unit area in the central region is greater than the amount of open area per unit area in the outer peripheral region.

15. The apparatus of claim 1, wherein the amount of open area per unit area in the central region is greater than the amount of open area per unit area in the inner peripheral region.

16. The apparatus of claim 1, wherein the nutrient transport structure has larger nutrient flow paths in the center region than in at least one of the outer peripheral region and the inner peripheral region.

17. An apparatus for aligning an implant with a visual axis of an eye of a patient, the apparatus comprising:
   an instrument having an instrument axis and an aperture through which the patient may look along the instrument axis; and
   wherein the implant comprises an aperture having an implant axis that can be positioned substantially collinear with the instrument axis, the implant further comprising a annulus configured to be substantially opaque to visible light and to extend between the aperture and an outer periphery of the implant, the annulus having an inner peripheral region between a central region and the aperture and an outer peripheral region between the central region and the outer periphery of the implant, the inner peripheral, central and outer peripheral regions each having a nutrient transport structure for conveying nutrients between anterior and posterior surfaces of the implant, the nutrient transport structure providing a concentration of open area in the central region that is greater than a concentration of open area in at least one of the outer peripheral region and the inner peripheral region.

18. An apparatus for aligning a corneal implant with a visual axis of an eye of a patient, the apparatus comprising:
   an instrument having an instrument axis and an aperture through which the patient may look along the instrument axis; and
   wherein the corneal implant comprises an aperture having a corneal implant axis that can be positioned substantially collinear with the instrument axis, the corneal implant further comprising a annulus configured to be substantially opaque to visible light and to extend between the aperture and an outer periphery of the corneal implant, the annulus having an inner peripheral region between a central region and the aperture and an outer peripheral region between the central region and the outer periphery of the corneal implant, the inner peripheral, central and outer peripheral regions each having a nutrient transport structure for conveying nutrients between anterior and posterior surfaces of the corneal implant, the nutrient transport structure providing a concentration of open area in the central region that is greater than a concentration of open area in at least one of the outer peripheral region and the inner peripheral region.

* * * * *

UNITED STATES PATENT AND TRADEMARK OFFICE
CERTIFICATE OF CORRECTION

| | |
|---|---|
| PATENT NO. | : 8,079,706 B2 |
| APPLICATION NO. | : 11/418390 |
| DATED | : December 20, 2011 |
| INVENTOR(S) | : Thomas Silvestrini et al. |

It is certified that error appears in the above-identified patent and that said Letters Patent is hereby corrected as shown below:

Title Page 5

In column 1 at line 31, under Other Publications, change "Opthal." to --Ophthal.--.

In column 1 at line 32, under Other Publications, change "Opthal." to --Ophthal.--.

In column 1 at line 48, under Other Publications, change "Stenipeic." to --Stenopeic--.

In column 1 at line 63, under Other Publications, change "Opthalmology" to --Ophthalmology--.

In column 1 at line 68, under Other Publications, change "Opthal." to --Ophthal.--.

In column 2 at line 1, under Other Publications, change "deth." to --depth.--.

In column 2 at line 9, under Other Publications, change "Opthal." to --Ophthal.--.

In column 2 at line 24, under Other Publications, change "Stromectomy" to --Strumectomy--.

In column 2 at line 27, under Other Publications, change "Intracornel" to --Intracorneal--.

In column 2 at line 64, under Other Publications, change "intracorneallens" to --intracorneal lens--.

Title Page 6

In column 1 at line 17, under Other Publications, change "Opthalmic" to --Ophthalmic--.

In column 2 at line 11, under Other Publications, change "Opthalmology," to --Ophthalmology,--.

In column 4 at line 20, change "is" to --is a--.

In column 5 at line 1, change "another an" to --another--.

In column 5 at line 49, after "target" insert --fixation target--.

In column 5 at line 51, after "the" insert --first target--.

In column 5 at line 53, after "the" insert --second target--.

In column 5 at line 63, change "devices" to --device--.

Signed and Sealed this
Twenty-sixth Day of June, 2012

David J. Kappos
*Director of the United States Patent and Trademark Office*

CERTIFICATE OF CORRECTION (continued)
U.S. Pat. No. 8,079,706 B2

In column 6 at line 5, change "61C" to --61A--. (2nd occurrence)

In column 6 at line 11, after "holes" insert --of a plurality of--.

In column 8 at line 16, change "center" to --center,--.

In column 10 at line 34, change "62" to --64--.

In column 12 at line 42-58, delete "FIG. 1, indicating a first axis . . . lens 14 (see FIGS. 2-3)." and insert the same on Col. 12, line 41, after "shown in" as a continuation of the paragraph.

In column 13 at line 56, change "f A" to --f. A--.

In column 14 at line 5, change "45B" to --45B,--.

In column 14 at line 27, change "10204d" to --1020d--.

In column 16 at line 20, change "213" to --1213--.

In column 16 at line 55, change "10 a" to --10 of a--.

In column 17 at line 37, change "420" to --1420--.

In column 19 at line 28, change "connection" to --connection with--.

In column 19 at line 61, change "2068" to --2224--.

In column 21 at line 56, change "2050" to --2052--.

In column 22 at line 66, change "2124" to --2120--.

In column 23 at line 57, after "optics" delete "of".

In column 25 at line 38, change "2080" to --2102--.

In column 32 at line 33, change "2520" to --2536--.

In column 33 at line 60, change "and a" to --a--.

In column 35 at line 63, change "transmissve" to --transmissive--.

In column 36 at line 10, change "transmissve" to --transmissive--.

In column 39 at line 4, change "non-uniform uniform" to --non-uniform--.

In column 39 at line 11, change "outer" to --inner--.

In column 39 at line 19, change "hole" to --holes--.

In column 39 at line 23, change "4226" to --4225--.

In column 40 at line 1, change "4304" to --4320--.

In column 40 at line 2, change "4304" to --4320--.

In column 40 at line 42, change "44008" to --4408--.

In column 40 at line 51, change "4404" to --4420--.

In column 40 at line 52, change "4404" to --4420--.

In column 40 at line 59, after "surface" (1st occurrence) insert --4408--.

In column 40 at line 59, after "surface" (2nd occurrence) insert --4412--.

In column 41 at line 6, change "44466a" to --4466a--.

In column 41 at line 8, change "4336" to --4436--.

CERTIFICATE OF CORRECTION (continued)
U.S. Pat. No. 8,079,706 B2

In column 41 at line 10, change "4336" to --4436--.

In column 41 at line 27, change "patter" to --pattern--.

In column 42 at lines 30-31, change "and or" to --and/or--.

In column 42 at line 50, change "transmissve" to --transmissive--.